US010920290B2

(12) United States Patent
Salzman et al.

(10) Patent No.: US 10,920,290 B2
(45) Date of Patent: Feb. 16, 2021

(54) **ENGINEERED BACTERIAL STRAIN THAT REDUCES ANTIBIOTIC-RESISTANT *ENTEROCOCCUS* COLONIZATION IN THE GI TRACT**

(71) Applicant: THE MEDICAL COLLEGE OF WISCONSIN, INC., Milwaukee, WI (US)

(72) Inventors: Nita Salzman, Milwaukee, WI (US); Christopher Kristich, Milwaukee, WI (US); Sushma Kommieni, Milwaukee, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 43 days.

(21) Appl. No.: 16/485,736

(22) PCT Filed: Feb. 14, 2018

(86) PCT No.: PCT/US2018/018099
§ 371 (c)(1),
(2) Date: Aug. 13, 2019

(87) PCT Pub. No.: WO2018/152148
PCT Pub. Date: Aug. 23, 2018

(65) Prior Publication Data

US 2020/0056251 A1 Feb. 20, 2020

Related U.S. Application Data

(60) Provisional application No. 62/459,281, filed on Feb. 15, 2017, provisional application No. 62/529,713, filed on Jul. 7, 2017.

(51) Int. Cl.
*C12N 1/20* (2006.01)
*C12R 1/46* (2006.01)
*A61P 31/04* (2006.01)
*C12N 9/52* (2006.01)
*C12N 15/52* (2006.01)

(52) U.S. Cl.
CPC ................ *C12R 1/46* (2013.01); *A61P 31/04* (2018.01); *C12N 1/20* (2013.01); *C12N 9/52* (2013.01); *C12N 15/52* (2013.01)

(58) Field of Classification Search
CPC ........................................................ C12R 1/46
See application file for complete search history.

(56) References Cited

U.S. PATENT DOCUMENTS

| | | | |
|---|---|---|---|
| 5,032,512 | A | 7/1991 | Witholt |
| 5,728,380 | A | 3/1998 | Allen |
| 9,381,244 | B2 | 7/2016 | Noelle |
| 2007/0098744 | A1 | 5/2007 | Knorr |
| 2008/0219960 | A1 | 9/2008 | Nierop Groot |
| 2013/0236419 | A1 | 9/2013 | Schneewind |

FOREIGN PATENT DOCUMENTS

EP 0508701 A2 10/1992

OTHER PUBLICATIONS

European Patent Application No. 18754865.6—European Supplementary Search Report, dated Oct. 16, 2020.

Lopetuso, et al. Bacteriocins and Bacteriophages: Therapeutic Weapons for Gastrointestinal Diseases? J. Molecular Sciences. 2019. 20(1): 183.

Arthur TD, et al: On bacteriocin delivery systems and potential applications. Future Microbiol 2014, 9(2):235-248.

Benyacoub J, et al: Supplementation of food with Enterococcus faecium (SF68) stimulates immune functions in young dogs. J Nutr 2003, 133(4):1158-1162.

Broaders E, et al: Mobile genetic elements of the human gastrointestinal tract: potential for spread of antibiotic resistance genes. Gut microbes 2013, 4(4):271-280.

Cotter PD, et al: Bacteriocins—a viable alternative to antibiotics? Nat Rev Microbiol 2013, 11(2):95-105.

Dobson, Alleson, et al. "Bacteriocin production: a probiotic trait?." Appl. Environ. Microbiol. 78.1 (2012): 1-6.

Fisher K, et al: The ecology, epidemiology and virulence of Enterococcus. Microbiology 2009, 155(Pt 6):1749-1757.

Gibson DG, et al: Enzymatic assembly of DNA molecules up to several hundred kilobases. Nat Methods 2009, 6(5):343-U341.

Guiton, Pascale S., et al. "Contribution of autolysin and sortase A during Enterococcus faecalis DNA-dependent biofilm development." Infection and immunity 77.9 (2009): 3626-3638.

Hammami R, et al: Anti-infective properties of bacteriocins: an update. Cellular and molecular life sciences : CMLS 2013, 70(16):2947-2967.

Hegstad K, et al: Mobile genetic elements and their contribution to the emergence of antimicrobial resistant Enterococcus faecalis and Enterococcus faecium. Clinical microbiology and infection : the official publication of the European Society of Clinical Microbiology and Infectious Diseases 2010, 16(6):541-554.

International Searching Authority, International Search Report and Written Opinion for application PCT/US2018/18099, dated Feb. 14, 2018, 11 pages.

(Continued)

*Primary Examiner* — Albert M Navarro
*Assistant Examiner* — Mark Navarro
(74) *Attorney, Agent, or Firm* — Quarles & Brady LLP

(57) ABSTRACT

The present disclosure provides engineered modified strains of *Enterococcus faecalis* (EF) that is able to produce bacteriocin but is inefficient at establishing long-term colonization of the GI track in an animal. Compositions comprising the modified strain and methods of use are also disclosed.

33 Claims, 14 Drawing Sheets

Specification includes a Sequence Listing.

(56) References Cited

OTHER PUBLICATIONS

Jack RW, et al: Bacteriocins of gram-positive bacteria. Microbiol Rev 1995, 59(2):171-200.
Kemp, Kelvin D., et al. "Relative contributions of Enterococcus faecalis OG1RF sortase-encoding genes, srtA and bps (srtC), to biofilm formation and a murine model of urinary tract infection." Infection and immunity 75.11 (2007): 5399-5404.
Kommineni S, et al: Harnessing bacteriocin biology as targeted therapy in the GI tract. Gut microbes 7.6 (2016): 512-517.
Kommineni, Sushma, et al. "Bacteriocin production augments niche competition by enterococci in the mammalian gastrointestinal tract." Nature 526.7575 (2015): 719.
Kommineni, Sushma, et al. Bacteriocin production augments niche competition by enterococci in the mammalian GI Tract. Poster at Gordon Research Conference, May 3, 2015.
Kristich CJ, et al: A eukaryotic-type Ser/Thr kinase in Enterococcus faecalis mediates antimicrobial resistance and intestinal persistence. Proc Natl Acad Sci U S A 2007, 104(9):3508-3513.
Kristich CJ, et al: Development of a method for markerless genetic exchange in Enterococcus faecalis and its use in construction of a srtA mutant. Applied and environmental microbiology 2005, 71(10):5837-5849.
Kristich CJ, et al: Genetic basis for vancomycin-enhanced cephalosporin susceptibility in vancomycin-resistant enterococci revealed using counterselection with dominant-negative thymidylate synthase. Antimicrobial agents and chemotherapy 2014, 58(3):1556-1564.
Lindenstrauss AG, et al: Transcriptome analysis of Enterococcus faecalis toward its adaption to surviving in the mouse intestinal tract. Archives of microbiology 2014, 196(6):423-433.
Maricic N, et al: Using the overlay assay to qualitatively measure bacterial production of and sensitivity to pneumococcal bacteriocins. J Vis Exp 2014(91):e51876.
McBride SM, et al: Genetic diversity among Enterococcus faecalis. PloS one 2007, 2(7):e582.
Paulsen IT, et al: Role of mobile DNA in the evolution of vancomycinresistant Enterococcus faecalis. Science 2003, 299(5615):2071-2074.
Perez RH, et al: Novel bacteriocins from lactic acid bacteria (LAB): various structures and applications. Microbial cell factories 2014, 13 Suppl 1:S3.
Pieniz S, et al: Probiotic potential, antimicrobial and antioxidant activities of Enterococcus durans strain LAB18s. Food Control 2014, 37:251-256.
Richards MJ, et al: Nosocomial infections in combined medical-surgical intensive care units in the United States. Infect Control Hosp Epidemiol 2000, 21(8):510-515.
Shepard BD, et al: Antibiotic-resistant enterococci: the mechanisms and dynamics of drug introduction and resistance. Microbes and Infection / Institut Pasteur 2002, 4(2):215-224.
Tomita, H., et al. Cloning and genetic and sequence analyses of the bacteriocin 21 determinant encoded on the Enterococcus faecalis pheromone-responsive conjugative plasmid pPD1. Journal of bacteriology 179, 7843-7855 , 1997.
Vesic D, et al: A Rex family transcriptional repressor influences H2O2 accumulation by Enterococcus faecalis. Journal of bacteriology 2013, 195(8):1815-1824.
Zheng J, et al: Diversity and dynamics of bacteriocins from human microbiome. Environmental microbiology 2015, 17(6):2133-2143.

Lawn of OG1RF (susceptible strain)

| Recipient | Donor | Transconjugants after 24 hours |
|---|---|---|
| OG1SP | OG1RF pPD1 | *25/25 |
| OG1SP | Δ*srtA* pPD1 | *3/50 |
| OG1SP | Δ*srtA* pPD1::Δ*bacAB*, bacABCDE+ | **0/50 |
| OG1SP | Δ*srtA* pPD1::Δ*bacAB* | **0/25 |

Fig. 7

Deletion of *bacAB* in pPD1

Partial pPD1 Δ*bacAB*::*ermC* (SEQ ID NO:1, contains part of pPD1 backbone and including the *ermC gene* insert, full pD1 sequence found in SEQ ID NO:10)

Sequence of *ermC* insert in red (replaces *bacAB*) (SEQ ID NO:2, underlined and bold)

SEQ ID NO:3 (fragment of backbone PD1 (full pPD1 found in SEQ ID NO10):, non-bold, non-underline)

ttccagagaatcggatggtattaattttaaagaacaatcagtattctgaaaaacaaataaatgttctcgatcagt
tacaaaagttagattttaagattgaggaattagaaagtaccttacagatagaagatgagaggttcaatctggaag
aatatcaagaagccatgattgatgaaaattatctttatgatatagatatcgtagaagaaaacaaagaagtagttc
aagcgtataaccaggatagaatgaaagataagtcaaatgaaaatgaacaatttgaaggaattagtcatgatattg
attgctaagaagtatctagtgactttttcttgattgaaactcaagatagatatgttattgcttgcatcaaaata
aactacatgggtataatagcaatgaaatgcatttccggacagatctcgacccgtgctataattatactaattta
taaggaggaaaaaatatgggcatttttagtatttttgtaatcagcacagttcattatcaaccaaacaaaaaataa
gtggttataatgaatcgttaataagcaaaattcatataaccaaattaaagagggttataatgaacgagaaaaata
taaaacacagtcaaaactttattacttcaaaacataatatagataaaataatgacaaatataagattaaatgaac
atgataatatctttgaaatcggctcaggaaaaggccattttacccttgaattagtaaagaggtgtaatttcgtaa
ctgccattgaaatagaccataaattatgcaaaactacagaaaataaacttgttgatcacgataatttccaagttt
taaacaaggatatattgcagtttaaatttcctaaaaaccaatcctataaaatatatggtaatatacettataaca
taagtacggatataatacgcaaaattgtttttgatagtatagctaatgagatttatttaatcgtggaatacgggt
ttgctaaaagattattaaatacaaaacgctcattggcattactttaatggcagaagttgatatttctatattaa
gtatggttccaagagaatattttcatcctaaacctaaagtgaatagctcacttatcagattaagtagaaaaaaat
caagaatatcacacaaagataaacaaaagtataattatttcgttatgaaatgggttaacaaagaatacaagaaaa
tatttacaaaaaatcaatttaacaattccttaaaacatgcaggaattgacgatttaaacaatattagctttgaac
aattcttatctcttttcaatagctataaattatttaataagtaatgttgtacatgcgattagatatcattaattt
tgagaaatatttgaaaatttccttctatatatcaatatttatttttttctgggagtgttagcagggattataat
aggtcctcatataaataaattggactattttggtcaggaagtttcattttatagtgttagtgttaataatttaaa
ggtctctttttatttcctcactataggaatggtaacagggggatttatgcatttttatttatgggtataaatgg
ttatataattggtaagttgattcaatatttatacattaacaatgaactaaatgttttgtataaaggtcttcttcc
acatttttttatagagcttttaggattggcaacatttagtatgataagtaccattccaatatttgttattttggt
tttttttaaaacgcctacacatgtagttcctattaaaaaaatcataaagttaagtgtgttttttactgtacttgg
aatagttttaataataattggaggatatatagaatctaatataagctatgtagatatacgatagaagttgagata
gaaaactaatctcaaaggaagatatccgcctatttccaaacgttatacgaaagaatttaaacaaaccattgatca
cgaatcaaaaaatgctgaattaaagatatactcattaaaggaagagtgggcactattttaaatttatacaaccaag
gtaaaaattttcgtgaattatctttataataatatgtcggttacttaaaatttttgaaattcacaataaacatat
aattaacagtgtgataatttatttgtctacaagtcaattgggataggcaactctagttgcataaaatatctctca
caaaaagtgtttcatgtattactgaatctgatccatataagttcttaagaaaggaagataagtttgtacaagttt
actttgaaaaaatacatcggtattacttcactatttttttgttttcaaatattctaattgctgaagagtttatt
tttgtagaaaaaaacttgagtttttccctaaattagggataattgtgcttgtttttttatgagtgctcccgct
tttgttgttgttactttaattttgacttgtttagttgcatttcttattagtttaattaacaaattttacagtttc
aaaagagtatacttatcgactttatttgtaaatagtattcagttattcgtaaatttagctttatttagtgtattt
ttacattacaatttaaatttgcgattgctaagtataatgagttttatgattaatattttttttagtagttatctat
cgcaatttattaattaaatttgcgaatgtaaacagtagggctgcgaatgtattatcaattttcgggattgcttta
tctgtaatttatttggtggtaggagtaaagtaatgaaaaaaataacaattaacaacttgagtttttattatgaat
ccaaagatattatggtgtttgacaggttatctttagaatttt

Fig. 8 pSK29 -- Plasmid for expression of BacA-E (in pAM401 vector) (SEQ ID NO:4)

Sequence in black: pAM401 vector (SEQ ID NO:5)
Sequence in Red: *bacA-E* nucleotide sequence (SEQ ID NO:6)-bold and underlined AGTTTCTTTTTCCGTGTGAATATCAAAATCAATAAAGAAGGTATTGATTTGTCTTAAATTGTTTTCAGAATGTCCTTTAGTGTA
TGAACGGTTTTCGTCTGCATACGTACCATAACGATAAACGTTTGGTGTCCAATGCGTAAATGTATCTTGATTTTCGTGAATCGC
TTCTTCGGAAGTCAGAACAACGCCACGTCCGCCAATCATGCTTTTTTTTGAGCGATACGCAAAAATAGCCCCTTTACTTTTACT
GGCTTGGTAGTGATTGAGCGAATTTTACTATTTTTAAATTTGTACTTTAACAAGCCGTCATGAAGCACAGTTTCTACAACAAAA
GGGATATTCATTCAGCTGTTCTCCTTTCTTACGAAAATTAATTAGTTAGAAGCTACGATCAAAGTTGAATCACAACAAAAAAGG
CAATCAACTAAGTTTTTCTTAATTGATTGCCTGGTATCTTCTTAAAGACTTGAAATCCCCTCAAAAACCCGATATAATGGGTTT
ACAGATATTTAAGTATCTGATTAATAAAGTAATTAAATACTTTACCAAATTTTGGGTCTCGACTTCTTTAATTGATTGGTGGTA
ATCAATTAAGGCTCGCAGTTAAAATTTCTCAGGCTTTAACTGGTCGTGGCTCTTTTTTTGTATTCTTTATTCAGTTCGTTGTTT
CGTTATATCTAGTATATCGCTTTTTAAAAAAATAAGCAATGATTTCGTGCATTATTCACACGAAATCATTGCTTTTTTCTTCTT
CCATTTCTAACTCCAATGTTACTTGTTCTGTTTCTGGTTCTGGTTCTGTTGGCTCATTTGGGATTAAATCCACTACTAGCGTTG
AGTTAGTTCCGTCTCTAATAGCCGGTTAAGTAATAGCCGGTTAAGTGGTCAAACTTTGGGAAAATCTCAACCCGCATTAAGTTT
TGATGCCATGACAATCGTTGGAAATTTGAACAAAACTAATGCTAAAAGCTATCTGACTTTATGAGTGTAGAGCCACAAATACG
ACTTTGGGATATACTTCAAACAAAGTTTAAAGCTAAGGCACTTCAAGAAAAAGTTTATATCGAATATGACAAAGTAAAAGCAGA
TACTTGGGATAGACGTAATATGCGTGTTGAATTTAATCCCAATAAACTCACACATGAAGAAATGATTTGGTTAAAACAAAATAT
TATCGACTACATGGAAGATGACGGTTTTACAAGATTAGACTTAGCTTTTGATTTTGAAGATGATTTGAGCGATTACTATGCAAT
GACTGATAAAGCAGTTAAGAAAACTGTTTTTTATGGTCGTAATGGCAAGCCAGAAACAAAATATTTTGGTGTCCGTGATAGTGA
TAGATTTATTAGAATTTATAATAAAAAACAAGAACGTAAAGATAACGCAGATGTTGAAGTTGTGTTTGAACATTTATGGCGTGT
AGAAGTTGAATTAAAAAGAGATATGGTTGATTACTGGAATGATTGTTTTAATGATTTACACATCTTTGAAACCTGCGTGGGCTA
CTTTAGAAAAAATTAATGAGCAAGCTATGGTTTATACTTTGTTGCATGAAGAAAGTATGTGGGGAAAGCTAAGTAAGAATACTA
AGACTAAATTTAAAAAATTGATTAGAGAAATATCTCCAATTGATTTAACGGAATTAATGAAATCGACTTTAAAAGCGAACGAAA
AACAATTGCAAAAGCAGATTGATTTTTGGCAACGTGAATTTAGGTTTTGGAAGTAAAATAAGTTTTATTTGATAAAAATTGCTA
ATTCAGTATAATTAATATTTACGAGGTGACATAACGTATGAAAAAATCAGAGGATTATTCCTCCTAAATATAAAAATTTAAAAT
TTAGGAGGAAGTTATATATGACTTTTAATATTATTGAATTAGAAAATTGGGATAGAAAAGAATATTTTGAACACTATTTTAATC
AGCAAACTACTTATAGCATTACTAAAGAAATTGATATTACTTTGTTTAAAGATATGATAAAAAAGAAAGGATATGAAATTTATC
CCTCTTTAATTTATGCAATTATGGAAGTTGTAAATAAAAATAAAGTGTTTAGAACAGGAATTAATAGTGAGAATAAATTAGGTT
ATTGGGATAAGTTAAATCCTTTGTATACAGTTTTTAATAAGCAAACTGAAAAATTTACTAACATTTGGACTGAATCTGATAAAA
ACTTCATTTCTTTTTATAATAATTATAAAAATGACTTGCTTGAATATAAAGATAAAGAAGAAATGTTTCCTAAAAAACCGATAC
CTGAAAACACCATACCGATTTCAATGATTCCTTGGATTGATTTTAGTTCATTTAATTTAAATATTGGTAACAATAGCAGCTTTT
TATTGCCTATTATTACGATAGGTAAATTTTATAGTGAGAATAATAAAATTTATATACCAGTTGCTCTGCAACTTCATCATTCTG
TATGTGATGGTTACCATGCTTCACTATTTATGAATGAATTTCAAGATATAATTCATAGGGTAGATGATTGGATTTAGTTTTTAG
ATTTTGAAAGTGAATTTAATTTTATACACGTAAGTGATCATAAAATTTATGAACGTATAACAACCACATTTTTTGGTTGCTTGT
GGTTTTGATTTTGAATTTGGTTTTGAACTTATGGACTGATTTATTCAGTCCATTTTTTGTGCTTGCACAAAAACTAGCCTCGCA
GAGCACACGCATTAATGACTTATGAAACGTAGTAAATAAGTCTAGTGTGTTATACTTTACTTGGAAGATGCACCGAATAAAAAA
TATTGAAGAACAACTAGCAAAAGATTTTAAAGAGTTATTTTATTTTAAGTCTTTATAACATGAGTGAAGCGAATTTTTAAATTT
CGATAGAAATTTTTACATCAAAAAGCCCCCTGTCAAAATTGACGAAGGGGGTTTTTTGGCGCACGCTTTTCGTTAGAAATATAC
AAGATTGAAAATCGTGTATAAGTGCGCCCTTTGTTTTGAACTTAGCACGTTACATCAATTTTTTAAAATGATGTATAAGTGCGC
CCTTTTAAATTTTGAGTGATTATATTTTTTGAGTTAGAAAAAGGGATTGGGAAAATTTCCCAAAATAATTTAAAAAATAAGCAA
AAATTTTCGATAGAGAATGTGCTATTTTTTGTCAAAGGTGTATACCTTGACTGTGCTTGCTGTTACATTAAGTTTATTTTTAAG
TTATTAAAAAAGAAATAGCTTTTAAAGTTTGGCTCGCTGTCGCTTTATAAAGCTGATTGACTTTTGATTGCAAACTACTTAAAG
AAAACAAACTCGGACTATTCGTTTTCTTCTCTTTGGTTTGAACATCAGCAATTATCCCCTCTTGATTGCCTATTTTAGCTTGTT
TAGAAGAAACAAAAGCTAAAAGCTCCTCTTGGGTTTTAAAACGCTGTGTGGGGCTTAGAACGCCCTTAAACGACCCTTGGTTTA
CTTTTATACTAGCTTCCACCTCGAAAAAAGGTTCTTTTTTAAAATTCTCTATGGCTTCCTGGCGCTGAAAAAATAAGGTATAAG
GTGGGCGTTTGAACACGTCCTAGTGAAAATGTACCTTGTACGCCCCTTCTGTTGTAAATTTAACGTATACAAAGGGCTTGCGTT
CATGCCGATCAACCAATCGGCAATTTGGCGTGTTTGCGCTTCTTGATAAAAGGGATAGTAATTCATTCCAGGTTGCAAATTTTG
AAAACCGCTTCGGATTACATCTTTTTCTAAGCTATTGATCCATAGTCTTTTAAATGTTTTATCTTTTGAAAAGGCATTTGCTTT
ATGGATAATCGACCAGGCGATATTTTCACCTTCTCTGTCGCTATCTGTTGCAACAATAATTGTATTTGCCTTTTTGAGAAGTTC
TGCAACAATTTTAAACTGCTTTCCCTTATCTTTTGCAACTTCAAAATCGTATCGATCAGGAAAAATCGGCAAAGATTCAAGTTT
CCAATTTTGCCACTTTTCGTCATAATGACCTGGTTCTGCTAATTCCACTAAATGCCCAAAACCAAAGGTGATAAACGTTTCATC
TGTAAATAGTGGGTCTTTGATCTCAAAATAACCGTCTTTTTTGGTGCTTTGTTTTAAAGCACTTGCGTAGGCTAATGCCTGGCT
TGGTTTTTCAGCTAAAATAACCGTACTCATTAACTATCCCTCTTTTCATTGTTTTTTCTTTGATCGACTGTCACGTTATATCTT

Fig. 8 (continued)

GCTCGATACCTTCTAAACGTTCGGCGATTGATTCCAGTTTGTTCTTCAACTTCTTTATCGGATAAACCATTCAAAAACAAATCG
AAAGCCGAGATGCGCCGCGTGCGGCTGCTGGAGATGGCGGACGCGATGGATATGTTCTGCCAAGGGTTGGTTTGCGCATTCACA
GTTCTCCGCAAGAATTGATTGGCTCCAATTCTTGGAGTGGTGAATCCGTTAGCGAGGTGCCGCCGGCTTCCATTCAGGTCGAGG
TGGCCCGGCTCCATGCACCGCGACGCAACGCGGGGAGGCAGACAAGGTATAGGGCGGCGCCTACAATCCATGCCAACCCGTTCC
ATGTGCTCGCCGAGGCGGCATAAATCGCCGTGACGATCAGCGGTCCAGTGATCGAAGTTAGGCTGGTAAGAGCCGCGAGCGATC
CTTGAAGCTGTCCCTGATGGTCGTCATCTACCTGCCTGGACAGCATGGCCTGCAACGCGGGCATCCCGATGCCGCCGGAAGCGA
GAAGAATCATAATGGGGAAGGCCATCCAGCCTCGCGTCGCGAACGCCAGCAAGACGTAGCCCAGCGCGTCGGCCGCCATGCCGG
CGATAATGGCCTGCTTCTCGCCGAAACGTTTGGTGGCGGGACCAGTGACGAAGGCTTGAGCGAGGGCGTGCAAGATTCCGAATA
CCGCAAGCGACAGGCCGATCATCGTCGCGCTCCAGCGAAAGCGGTCCTCGCCGAAAATGACCCAGAGCGCTGCCGGCACCTGTC
CTACGAGTTGCATGATAAAGAAGACAGTCATAAGTGCGGCGACGATAGTCATGCCCCGCGCCCCACCGGAAGGAGCTGACTGGGT
TGAAGGCTCTCAAGGGCATCGGTCGACGCTCTCCCTTATGCGACTCCTGCATTAGGAAGCAGCCCAGTAGTAGGTTGAGGCCGT
TGAGCACCGCCGCCGCAAGGAATGGTGCATGCAAGGAGATGGCGCCCAACAGTCCCCCGGCCACGGGGCCTGCCACCATACCCA
CGCCGAAACAAGCGCTCATGAGCCCGAAGTGGCGAGCCCGATCTTCCCCATCGGTGATGTCGGCGATATAGGCGCCAGCAACCG
CACCTGTGGCGCCGGTGATGCCGGCCACGATGCGTCCGGCGTAGAGTTCCAGAGAATCGGATGGTATTAATTTTAAAGAACAAT
CAGTATTCTGAAAAAACAAATAAATGTTCTCGATCAGTTACAAAAGTTAGATTTTAAGATTGAGGAATTAGAAAGTACCTTACAG
ATAGAAGATGAGAGGTTCAATCTGGAAGAATATCAAGAAGCCATGATTGATGAAAATTATCTTTATGATATAGATATCGTAG

AGAAAACAAAGAAGTAGTTCAAGCGTATAACCAGGATAGAATGAAAGATAAGTCAAATGAAAATGAACAATTTGAAGGAATTAG
TCATGATATTGATTGCTAAGAAGTATCTAGTGACTTTTTTCTTGATTGAAACTCAAGATAGATATGTTATTGCTTGCATCAAAA
TAAACTACATGGGTATAATAGCAATGAAATGCATTTCAAAAATATTTTGAGGAGGAGTATCATGGTTAAAGAAAATAAATTTTC
TAAGATTTTTATTTTAATGGCTTTGAGTTTTTTGGGGTTAGCCTTGTTTAGTGCAAGTCTTCAGTTTTTGCCGATTGCACATAT
GGCTAAAGAGTTCGGTATACCAGCAGCAGTTGCAGGAACTGTACTTAATGTAGTTGAAGCTGGTGGATGGGTCACTACTATTGT
ATCAAATCTTACTGCTGTAGGTAGCGGAGGTCTTTCCTTACTCGCTGCAGCAGGAAGAGAGTCAATTAAAGCATACCTTAAGAA
AGAAATTAAGAAAAAAAGGAAAAAGAGCAGTTATTGCTTGGTAATTTAACAATATGATAAAAAAACAGGATATTTTCTAGAGATA
TTCTGTTTTTTAATTAAAAAAAGGGGGGCGCTCATGAATCTCTTTGGAATTCTAATGAAGTTAAGAATAAATCAAGAGAGTAGT
TTGGTTAAAAGAGTACTTTCCTACTTTAACTTAAAACTATCGTTAAAGCTCTATTTATTTATTAATATATTCTTTGAATTTTCA
TTGGCATTTGTTGTTAGTTTGGGATTAAGACTAACTTTAATAAAATCAGATATAAATGTAAATTTATTTTTTATAATATTTTTT
ATTTTAGGAATTGTTCAAGGAGCATCAAATTGTTATAGAACGCACGTCTTTCCTTTTGAAGAATTAAGGAAATTAGCAACAATA
TCTTCTAGAAAAGATAAGCTTTATTATGATTGTTACAGACTTATTCTATATTTTTATGTTTTCATCTTCAATACTATATGGATTA
TTGAGTTTAATATATATAAGAGTAGTAATGCTTTATTTTTCAAAAAATTAGTCTATCTGTATTTTTTTTATTTATATACATTTGT
TCATTTTATTGTAGTAATAGGATTTTTGGACAGTATATCTATAATAAAATAGTTAAGGCTATTGGATTAACACGATTAATCCTT
TATAGCATTGGAGCCCGCTTTATTTACTTATTTTGGTTTTTTTATAGTATCATTCGTATTTAGTAACATAGTATATTTTATAAAA
AAATATTTTGTTAACATAGAAAGTGTAAATAATAAAGTAATATGGGAGTCGTTTTCTAAGGATATAGGAATGTTTTATGTAAAT
AGCGCCAGTAAATTTTATGAGAGTCATGTATATTCATTTACTTATATAGATGTTTTTTTAGTATCGGCTATGTTATTAATTTTG
GCAATATTACTATTAGCTATGGAACCAAAACTCTACCCTTTAAAAACAAAAATGCTGCCAAAAACTAAAATAGACTTATGCAAT
TTATATGTATTTTTTTTGAATAAAGCATTAAAAAAAAATATTTTTTTTAAATGCAGCTTGTTAAAGTTAGCTAATACAAGATGG
ATTATTGCTAATAATTTCTTTCAAAATATAATTTTGACATATGAATCATTCTTTTACATTGGAGTAATGCTTTCAATAATACTA
TTGAATTCACAAAATAGAATGTTGCAAATACAACTATTATTTCTTTTAAATATACTTGTAATTGGAAATCAGACATTTGAAATA
AGAGAAGAAATGTACCCTTATCTATCTTTTGGATCAGAAAGGAATCAATTTACGCTTCTAAGATCGTCTCCGAATGGTTTGAAT
AAAGTTTTAATTCGAAACTAACGATATACAGGTTATTTTTATTAATTCCTTTACTTATATTAATTATCATAAATATTGTAGTT
TCTGTATACATTATGATTCCGGTAATTTTTGCTATCTTTTTGTTTATAACATTTTCTATGTCTGTGTATGTTTTCCCTATGATT
CAAATGTATATGATTCCTTTAGCTACTAAACTAGATTACACTAATGATACAGAAATTGGAAGTGCTAAAGATGAAAAAATTGTT
TTAGAGAAATTTCAAACAGTTCCAAGATACTTTTTTAATATCGTTCCTTTAGTGCTTACATTTATCTTTCCAATTGTAGGGGAA
AGTTATTCATTAATAATATTTTTCGGAGAGTTAGTATATTTCTCTTTAGCAACAATAATATTTGTGTTTTTCAGTAAAAAAATT
ATTAGGAAAGGAATTTTTGTTGTACATGCGATTAGATATCATTAATTTTGAGAAATATTTGAAAATTTCCTTCTATATATCAAT
ATTTATTTTTTTTCTGGGAGTGTTAGCAGGGATTATAATAGGTCCTCATATAAATAAATTGGACTATTTTGGTCAGGAAGTTTC
ATTTTATAGTGTTAGTGTTAATAATTTAAAGGTCTCTTTTTATTTCCTCACTATAGGAATGGTAACAGGGGGGATTTATGCATT
TTTATTTATGGGTATAAATGGTTATATAATTGGTAAGTTGATTCAATATTTATACATTAACAATGAACTAAATGTTTTGTATAA
AGGTCTTCTTCCACATTTTTTTATAGAGCTTTTAGGATTGGCAACATTTAGTATGATAAGTACCATTCCAATATTTGTTATTTT
GGTTTTTTTTAAAACGCCTACACATGTAGTTCCTATTAAAAAAATCATAAAGTTAAGTGTGTTTTTTACTGTACTTGGAATAGT
TTTAATAATAATTGGAGGATATATAGAATCTAATATAAGCTATGTAGATATACGATAGAAGTTGAGATAGAAAACTAATCTCAA
AGGAAGATATCCGCCTATTTCCAAACGTTATACGAAAGAATTTAAACAAACCATTGATCACGAATCAAAAATGCTGAATTAAAG
ATATACTCATTAAAGGAAGAGTGGGCACTATTTTAAATTTATACAACCAAGGTAAAAATTTTCGTGAATTATCTTTATAATAAT
ATGTCGGTTACTTAAAATTTTTGAAATTCACAATAAACATATAATTAACAGTGTGATAATTTATTTGTCTACAAGTCAATTGGG
ATAGGCAACTCTAGTTGCATAAAATATCTCTCACAAAAAGTGTTTCATGTATTACTGAATCTGATCCATATAAGTTCTTAAGAA
AGGAAGATAAGTTTGTACAAGTTTACTTTGAAAAAATACATCGGTATTACTTCACTATTTTTTTTTGTTTTCAAATATTCTAATT
GCTGAAGAGTTTATTTTTGTAGAAAAAAACTTGAGTTTTTTCCCTAAATTAGGGATAATTGTGCTTGTTTTTTTTATGAGTGCT
CCCGCTTTTGTTGTTGTTACTTTAATTTTGACTTGTTTAGTTGCATTTCTTATTAGTTTAATTAACAAATTTTACAGTTTCAAA
AGAGTATACTTATCGACTTTATTTGTAAATAGTATTCAGTTATTCGTAAATTTAGCTTTATTTAGTGTATTTTTACATTACAAT
TTAAATTTGCGATTGCTAAGTATAATGAGTTTTATGATTAATATTTTTTTAGTAGTTATCTATCGCAATTTATTAATTAAATTT
GCGAATGTAAACAGTAGGGCTGCGAATGTATTATCAATTTTCGGGATTGCTTTATCTGTAATTTATTTGGTGGTAGGAGTAAAG
TAATGAAAAAAATAACAATTAACAACTTGAGTTTTTATTATGAATCCAAAGATATTATGGTGTTTGACAGGTTATCTTTAGAAT
TTTCTTCTGAAAAAAGTTATGCACTAGTTGGTTCTAATGGTGTAGGAAAAACAACATTGTTAAATATTTTATCAGGTATATATC
AACCCACAGGGGGAACAATAGAATATGACAGCACTTTGTATACAGAAAAAGTAACTAAAGAAAAAGTAGCTTTTATACCATATA

Fig. 8 (continued)

AAACTAAGCTATATCCTTATCTTGATGTTTTTGATCATATAAAGCTAATAGCAGAATTATGGGGAATTAAAACAGACTATTTAG
AATATAAAAGAAAAGTACTAGAATATTGTAGCCGTCTAAACTTGGACTATTATAATAAGAAAGTAGAGTCTTACTCTACAGGTA
TGGAGTATAAACTATACATTTCTTTAATGTTGGCAAGAGATGTTTCTCTTGTATTATTAGATGAACCTTTTACAATGTTAGATA
AAAAAAGTCGATATTTAGCTATGGACTTAATCAAAGAGAAAAAAATAATAACAATATTTTCTTCACATCAGAAAGATATTGTAG
AATATTTGTCAAATGATATTATTAATCTTGACAAACTGAAGGGAGTAAACTTGGAAAATTATGAAAAGAATTGATTACATTATT
ATTATAGTCTCACTATTAGCAACAATAGTCGCAATATTTTTAATAGGGATAGATTCTATGTTAGGCACAGGACGGGTGTGGTCG
CCATGATCGCGTAGTCGATAGTGGCTCCAAGTAGCGAAGCGAGCAGGACTGGGCGGCGGCCAAAGCGGTCGGACAGTGCTCCGA
GAACGGGTGCGCATAGAAATTGCATCAACGCATATAGCGCTAGCAGCACGCCATAGTGACTGGCGATGCTGTCGGAATGGACGA
TATCCCGCAAGAGGCCCGGCAGTACCGGCATAACCAAGCCTATGCCTACAGCATCCAGGGTGACGGTGCCGAGGATGACGATGA
GCGCATTGTTAGATTTCATACACGGTGCCTGACTGCGTTAGCAATTTAACTGTGATAAACTACCGCATTAAAGCTTATCGATGA
TAAGCTGTCAAACATGAGAATTACAACTTATATCGTATGGGGCTGACTTCAGGTGCTACATTTGAAGAGATAAATTGCACTGAA
ATCTAGAAATATTTTATCTGATTAATAAGATGATCTTCTTGAGATCGTTTTGGTCTGCGCGTAATCTCTTGCTCTGAAAACGAA
AAAACCGCCTTGCAGGGCGGTTTTTCGAAGGTTCTCTGAGCTACCAACTCTTTGAACCGAGGTAACTGGCTTGGAGGAGCGCAG
TCACCAAAACTTGTCCTTTCAGTTTAGCCTTAACCGGCGCATGACTTCAAGACTAACTCCTCTAAATCAATTACCAGTGGCTGC
TGCCAGTGGTGCTTTTGCATGTCTTTCCGGGTTGGACTCAAGACGATAGTTACCGGATAAGGCGCAGCGGTCGGACTGAACGGG
GGGTTCGTGCATACAGTCCAGCTTGGAGCGAACTGCCTACCCGGAACTGAGTGTCAGGCGTGGAATGAGACAAACGCGGCCATA
ACAGCGGAATGACACCGGTAAACCGAAAGGCAGGAACAGGAGAGCGCACGAGGGAGCCGCCAGGGGGAAACGCCTGGTATCTTT
ATAGTCCTGTCGGGTTTCGCCACCACTGATTTGAGCGTCAGATTTCGTGATGCTTGTCAGGGGGGCGGAGCCTATGGAAAAACG
GCTTTGCCGCGGCCCTCTCACTTCCCTGTTAAGTATCTTCCTGGCATCTTCCAGGAAATCTCCGCCCCGTTCGTAAGCCATTTC
CGCTCGCCGCAGTCGAACGACCGAGCGTAGCGAGTCAGTGAGCGAGGAAGCGGAATATATCCTGTATCACATATTCTGCTGACG
CACCGGTGCAGCCTTTTTTCTCCTGCCACATGAAGCACTTCACTGACACCCTCATCAGTGCCAACATAGTAAGCCAGTATACAC
TCCGCTAGCGCTGATGTCCGGCGGTGCTTTTGCCGTTACGCACCACCCCGTCAGTAGCTGAACAGGAGGGACAGCTGATAGAAA
CAGAAGCCACTGGAGCACCTCAAAAACACCATCATACACTAAATCAGTAAGTTGGCAGCATCACCCGACGCACTTTGCGCCGAA
TAAATACCTGTGACGGAAGATCACTTCGCAGAATAAATAAATCCTGGTGTCCCTGTTGATACCGGGAAGCCCTGGGCCAACTTT
TGGCGAAAATGAGACGTTGATCGGCACGTAAGAGGTTCCAACTTTCACCATAATGAAATAAGATCACTACCGGGCGTATTTTTT
GAGTTATCGAGATTTTCAGGAGCTAAGGAAGCTAAAATGGAGAAAAAAATCACTGGATATACCACCGTTGATATATCCCAATGG
CATCGTAAAGAACATTTTGAGGCATTTCAGTCAGTTGCTCAATGTACCTATAACCAGACCGTTCAGCTGGATATTACGGCCTTT
TTAAAGACCGTAAAGAAAAATAAGCACAAGTTTTATCCGGCCTTTATTCACATTCTTGCCCGCCTGATGAATGCTCATCCGGAA
TTCCGTATGGCAATGAAAGACGGTGAGCTGGTGATATGGGATAGTGTTCACCCTTGTTACACCGTTTTCCATGAGCAAACTGAA
ACGTTTTCATCGCTCTGGAGTGAATACCACGACGATTTCCGGCAGTTTCTACACATATATTCGCAAGATGTGGCGTGTTACGGT
GAAAACCTGGCCTATTTCCCTAAAGGGTTTATTGAGAATATGTTTTTCGTCTCAGCCAATCCCTGGGTGAGTTTCACCAGTTTT
GATTTAAACGTGGCCAATATGGACAACTTCTTCGCCCCCGTTTTCACCATGGGCAAATATTATACGCAAGGCGACAAGGTGCTG
ATGCCGCTGGCGATTCAGGTTCATCATGCCGTCTGTGATGGCTTCCATGTCGGCAGAATGCTTAATGAATTACAACAGTACTGC
GATGAGTGGCAGGGCGGGGCGTAATTTTTTTAAGGCAGTTATTGGTGCCCTTAAACGCCTGGTGCTACGCCTGAATAAGTGATA
ATAAGCGGATGAATGGCAGAAATTCGAAAGCAAATTCGACCCGGTCGTCGGTTCAGGGCAGGGTCGTTAAATAGCCGCTTATGT
CTATTGCTGGTTTACCGGTTTATTGACTACCGGAAGCAGTGTGACCGTGTGCTTCTCAAATGCCTGAGGCCAGTTTGCTCAGGC
TCTCCCCGTGGAGGTAATAATTGACGATATGATCATTTATTCTGCCTCCCAGAGCCTGATAAAAACGGTTAGCGCTTCGTTAAT
ACAGATGTAGGTGTTCCACAGGGTAGCCAGCAGCATCCTGCGATGCAGATCCGGAACATAATGGTGCAGGGCGCTTGTTTCGGC
GTGGGTATGGTGGCAGGCCCCGTGGCCGGGGGACTGTTGGGCGCTGCCGGCACCTGTCCTACGAGTTGCATGATAAAGAAGACA
GTCATAAGTGCGGCGACGATAGTCATGCCCCGCGCCCACCGGAAGGAGCTACCGGACAGCGGTGCGGACTGTTGTAACTCAGAA
TAAGAAATGAGGCCGCTCATGGCGTTGACTCTCAGTCATAGTATCGTGGTATCACCGGTTGGTTCCACTCTCTGTTGCGGGCAA
CTTCAGCAGCACGTAGGGGACTTCCGCGTTTCCAGACTTTACGAAACACGGAAACCGAAGACCATTCATGTTGTTGCTCAGGTC
GCAGACGTTTTGCAGCAGCAGTCGCTTCACGTTCGCTCGCGTATCGGTGATTCATTCTGCTAACCAGTAAGGCAACCCCGCCAG
CCTAGCCGGGTCCTCAACGACAGGAGCACGATCATGCGCACCCGTGGCCAGGACCCAACGCTGCCCGACTTTAAACGTGGATCA
TTTTCTTTAAATTTATGCTGACGACCTTTGAATTTGCCTTTTTTCTTAGCAATTTCGATTCCTTGTGCCTGACGTTCCTTAATT
TTTTTTCGTTCTGATTCTGCTTGATACTTGTACAATTCAATGACAAGGCTATTAATCAAACGCCTTAAATTTTCATCTTCAATA
CCATTCATTGAGGGTAAATTTAAGACTTCCAGGGTTGCCCCCTTAATTTGAATTTGATTCATCAATTCTGTTAATTCTTTATTA
TTTCGTCCTAATCGATCTAATTCAGTAACAATAACAATATCCCCTTCACGAATATAGTTAAGCATAGCTTGTAATTGTGGGCGT
TCGACCGATTGACCGCTTAATTTGTCTGAAAAGACCTTAGAAACGCCCTGTAACGCTTGTAATTGCCGATCTAAGTTCTGTTCT
TTGCTACTGACACGTGCATAACCAATTTTAGCCATTTTCAACCAACCTCTAAAATTCTCTCGGTTGCAATAACCAATCAGCAAT
ATCTACTTTTTCAATTTCAAATTGCTTATCAGAAATTGTCTTTTCGTAAGCGATAAAATCTTGCGCATATTGTTGCTCATTAAA
AATAGCCACCACTTCGTCATTTTCTAAAACTCGATAAATAAATTTTTTCATTTACTCCTCCTATTATGCCCAACTTAAATGAC
CTATTCACCAAGTCAATTATACTGCTAAAATCATATTAGGACAAATAGGTATACTCTATTGACCTATAAATGATAGCAACTTAA
AAGATCAAGTGTTCGCTTCGCTCTCACTGCCCCTCGACGTTTTAGTAGCCTTTCCCTCACTTCGTTCAGTCCAAGCCAACTAAA
AGTTTTCGGGCTACTCTCTCCTTCTCCCCCTAATAATTAATTAAAATCTTACTCTGTATATTTCTGCTAATCATTCACTAAACA
GCAAAGAAAAACAAACACGTATCATAGATATAAATGTAATGGCATAGTGCGGGTTTTATTTTCAGCCTGTATCGTAGCTAAACA
AATCGAGTTGTGGGTCCGTTTTGGGGCGTTCTGCCAATTTGTTTAGAGTTTCTTGAATAAATGTACGTTCTAAATTAAACGAAG
CTGTCAGCGCCTTTATATAGCTTTCTCGTTCTTCTTTTTTTAATTTAATGATCGATAGCAACAATGATTTAACACTAGCAAGTT
GAATGCCACCATTTCTTCCTGGTTTAATCTTAAAGAAAATTTCCTGATTCGCCTTCAGTACCTTCAGCAATTTATCTAATGTCC
GTTCAGGAATGCCTAGCACTTCTCTAATCTCTTTTTTGGTCGTCGCTAAATAAGGCTTGTATACATCGCTTTTTTCGCTAATAT
AAGCCATTAAATCTTCTTTCCATTCTGACAAATGAACACGTTGACGTTCGCTTCTTTTTTTCTTGAATTTAACCACCCTTGAC
GGACAAATAAATCTTTACTGGTTAAATCACTTGATACCCAAGCTTTGCAAAGAATGGTAATGTATTCCCTATTAGCCCCTTGAT
AGTTTTCTGAATAGGCACTTCTAACAATTTTGATTACTTCTTTTTCTTCTAAGGGTTGATCTAATCGATTATTAAACTCAAACA

Fig. 8 (continued)

TATTATATTCGCACGTTTCGATTGAATAGCCTGAACTAAAGTAGGCTAAAGAGAGGGTAAACATAACGCTATTGCGCCCTACTA
AACCCTTTTCTCCTGAAAATTTCGTTTCGTGCAATAAGAGATTAAACCAGGGTTCATCTACTTGTTTTTTGCCTTCTGTACCGC
TTAAAACCGTTAGACTTGAACGAGTAAAGCCCTTATTATCTGTTTGTTTGAAAGACCAATCTTGCCATTCTTTGAAAGAATAAC
GGTAATTGGGATCAAAAAATTCTACATTGTCCGTTCTTGGTATACGAGCAATCCCAAAATGATTGCACGTTAGATCAACTGGCA
AAGACTTTCCAAAATATTCTCGGATATTTTGCGAGATTATTTTGGCTGCTTTGACAGATTTAAATTCTGATTTTGAAGTCACAT
AGACTGGCGTTTCTAAAACAAAATATGCTTGATAACCTTTATCAGATTTGATAATTAACGTAGGCATAAAACCTAAATCAATAG
CTGTTGTTAAAATATCGCTTGCTGAAAT

Fig. 9

Sortase A deletion

*E. faecalis* OG1RF *srtA* open reading frame (SEQ ID NO:7)(the sequence deleted in Δ*srtA* is indicated in red, bold and underlined (SEQ ID NO:8):,
SEQ ID NO:9 is the OGIRFΔsrtA (black sequence, non-underline, non-bold)

ATGCGCCCAAAAGAGAAAAAAAGAGGAAAAAATTGGTTAATCAACAGTTTATTAGTTTTACTATTTATCATTGGC
TTGGCCTTAATTTTTAACAATCAGATACGCAGTTGGGTGGTTCAACAAAATAGCCGCTCGTACGCCGTTAGCAAG
TTGAAACCAGCCGATGTGAAGAAAAATATGGCTCGTGAAACAACGTTTGACTTTGATTCAGTTGAGTCCTTGAGC
ACAGAAGCGGTGATGAAAGCCCAATTTGAAAACAAAAACTTACCTGTGATTGGTGCCATTGCGATACCAAGTGTC
GAAATTAATTTGCCCATTTTTAAAGGATTGTCAAATGTCGCTTTATTAACTGGTGCCGGGACCATGAAAGAAGAT
CAAGTCATGGGGAAAAACAATTATGCCTTGGCTAGTCATCGAACGGAAGATGGCGTTTCCTTATTTTCACCTTTA
GAAAGAACCAAAAAAGACGAACTCATTTATATCACTGATTTATCTACTGTTTATACATACAAAATAACTTCTGTA
GAAAAAATCGAACCAACCCGTGTTGAGTTAATTGATGACGTTCCTGGTCAAAATATGATTACCTTAATTACCTGT
GGCGATTTACAAGCAACGACGCGAATTGCTGTTCAAGGAACATTAGCAGCAACGACGCCTATTAAAGACGCCAAC
GACGATATGTTAAAGGCTTTCCAATTGGAGCAAAAAACCTTAGCCGATTGGGTGGCTTAA

ENGINEERED BACTERIAL STRAIN THAT REDUCES ANTIBIOTIC-RESISTANT *ENTEROCOCCUS* COLONIZATION IN THE GI TRACT

CROSS-REFERENCE TO RELATED APPLICATIONS

This application represents the national stage entry of PCT International Application No. PCT/US2018/018099 filed on Feb. 14, 2018 and claims priority to U.S. Provisional Application Nos. 62/459,281 and 62/529,713 filed on Feb. 15, 2017 and Jul. 7, 2017. respectively, the contents of which are incorporated by reference in their entireties.

GOVERNMENT FUNDING STATEMENT

This invention was made with government support under NIH GM099526 and NIH AI097619 awarded by National Institute of Health. The government has certain rights in the invention.

BACKGROUND OF THE INVENTION

Bacteriocins, ribosomally synthesized antimicrobial peptides of bacterial origin, have generated interest because of their application in medical and food-based products[1-3]. Bacteriocins produced by Gram-positive lactic acid bacteria (LAB) are of particular interest due to their application as probiotics, potential treatments against infectious agents and in packaged food preservation[3,4].

The full potential of bacteriocin use in clinical settings has not been fully explored, although recent advances in delivery methods have shown some progress[5]. Antimicrobial activity of bacteriocins towards diverse bacterial species varies and can be bactericidal or bacteriostatic at different concentrations[2,6,7]. In a complex ecosystem, such as the gastrointestinal (GI) tract, bacteriocin production helps the producing strain to occupy a niche by inhibiting its competitors[8,9].

*Enterococcus faecalis* (EF), a member of the LAB, is a Gram-positive, facultative anaerobe that is a normal resident of the intestinal tract of many animals and in humans[10]. *Enterococcal* probiotics are used to treat irritable bowel syndrome, diarrhea, high cholesterol and to aid immune regulation[11]. *Enterococcal* interactions with the GI microbiota and mucosal immune system are thought to mediate their beneficial effects[12].

Despite its commensal behavior, under certain circumstances, EF can invade the host thus displaying pathogenic potential[13,14]. Enterococci are among the three most common causes of nosocomial infections, and due to their high levels of antibiotic resistance, enterococcal infections can be difficult to treat[13,14]. Although enterococci constitute a minor fraction of the GI microbiota under normal circumstances, antibiotic treatment of the host can lead to massive overgrowth of intestinal EF and subsequent dissemination to extraintestinal sites to cause systemic EF infection[15-17].

Due to the inherent antibiotic resistance of EF, and its robust ability to acquire new drug resistance through gene transfer, new approaches are needed to prevent and treat these antibiotic-resistant nosocomial infections[16,17]. Our previous work on Bacteriocin-21 (Bac-21)-producing *Enterococcus faecalis* (EF-Bac+) in the mouse GI tract showed that the antibacterial activity of Bac-21 is primarily directed towards closely related species of enterococci, sparing the majority of the diverse population of the microbial community in the GI tract (unlike conventional antibiotics)[9,18]. This selective antimicrobial activity optimally positions EF-Bac+ as a precise tool to eliminate drug-resistant enterococci from the intestinal tract without collateral damage to the microbiota, thereby preventing the expansion, spread, and subsequent infections caused by drug-resistant enterococci.

However, one potential caveat to this approach is that the bacteriocin delivery strain itself will take up residence in the intestinal tract and may eventually acquire additional antibiotic resistance traits through a horizontal genetic exchange, re-creating the original problem[18]. A second potential caveat to this approach is that EF-Bac+ can conjugate (transmit) the bacteriocin-containing plasmid to other strains of EF in the GI tract[16].

Needed in the art is a way to overcome these challenges. In the specification below, Applicants disclose engineering an EF bacteriocin delivery strain to prevent stable colonization of the intestine and bacteriocin conjugation while retaining effective bacteriocin delivery abilities.

DESCRIPTION OF THE FIGURES

FIG. 7 shows the sequence of the partial pPD1 ΔbacAB:: ermC vector. SEQ ID NO:1 contains part of the pPD1 backbone and includes the ermC gene insert. The ermC insert is SEQ ID NO:2. The partial pPD1 backbone sequence is SEQ ID NO:3 (taken from the full pPD1 sequence found in SEQ ID NO:10).

FIG. 8 shows the sequence of the pSK29 plasmid for expression of BacA-E in the pAM401 vector (SEQ ID NO:4). The pAM401 vector backbone is SEQ ID NO:5 and the bacA-E nucleotide sequence is SEQ ID NO:6.

FIG. 9 shows the sortase A deletion in the open reading frame of *E. faecalis* srtA gene. *E. faecalis* OG1RF srtA open reading frame is SEQ ID NO:7. The portion deleted in the ΔsrtA mutant is SEQ ID NO:8.

DESCRIPTION OF THE INVENTION

In General

Figure 1A:
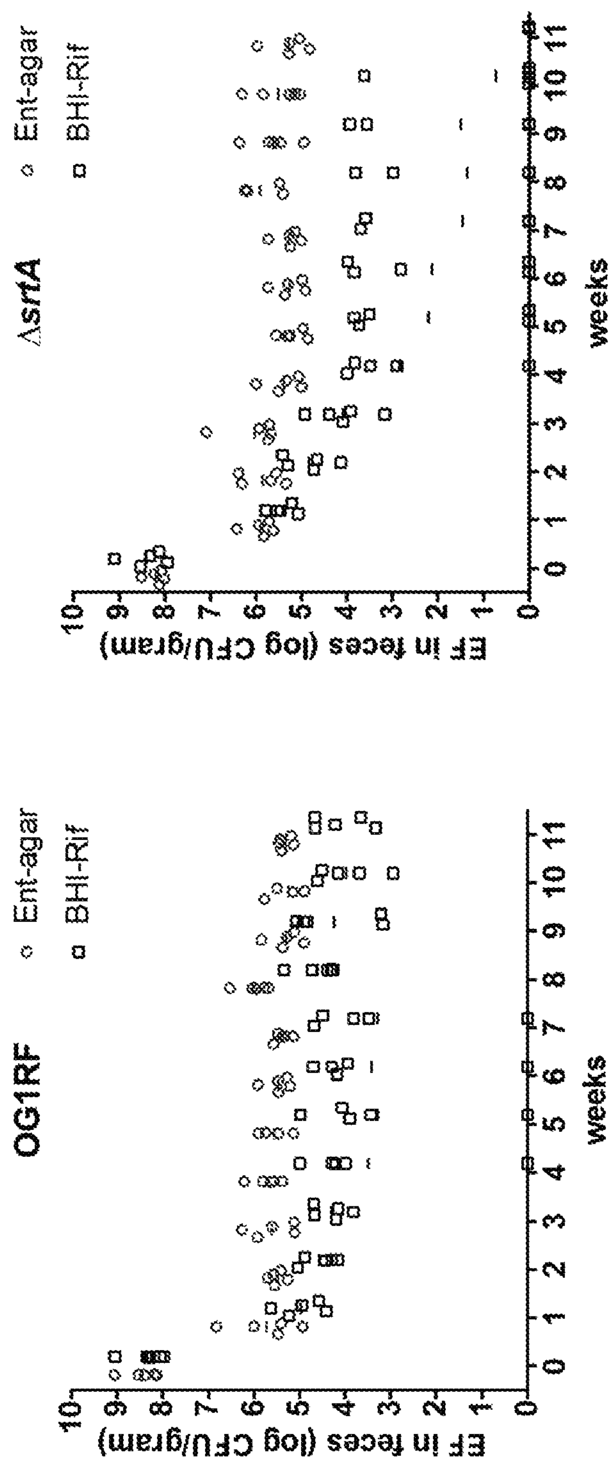
FIG. 1A is a graph evaluating mice colonized with EF. Mice (N=5 per group) were given rifampicin resistant EF (OG1RF; WT or ΔsrtA) for 14 days, at which time all mice were given sterile water (Week 0). After withdrawal of EF from drinking water, fecal samples were collected and abundance of enterococci was determined by enumeration on m-*Enterococcus* selective agar (Ent agar), and BHI agar with rifampicin (Rif). The results shown are representative of two independent experiments. Horizontal lines indicate geometric mean. Each symbol represents an individual animal. The limit of detection is 100 CFU per g feces.

Previous studies have focused on clinical isolates of *enterococcus* whose virulence properties are acquired by horizontal gene transfer[16,17,19]. However, these studies failed to identify specific fitness determinants essential for EF colonization of the host GI tract, which precedes infection. Because EF is a natural commensal of the GI tract, it is likely that the fundamental adaptation and survival traits required for GI colonization are encoded in the core genome of EF.

In the present invention, we disclose a member of the EF core genome that is important for stable GI colonization and exploit this knowledge to develop an improved EF-Bac+ delivery strain that is capable of eliminating drug-resistant enterococci from the mammalian GI tract but is itself impaired in bacteriocin conjugation and long-term GI colonization. These findings represent an important step towards implementation of our therapeutic strategy for the elimination of drug-resistant enterococci from the GI tract and prevention of enterococcal infections.

The Examples below show that we introduced a specific mutation into the gene cluster that encodes Bac21 bacteriocin on the pPD1 EF plasmid (full length pPD1 plasmid found in SEQ ID NO:10). When introduced into EF, the engineered pPD1 plasmid (partial sequence of pPD1 surrounding inserted gene found in SEQ ID NO:1 (inserted gene found in SEQ ID NO:2)) is not able to produce bacteriocin 21 or be transferred by conjugation to other EF by conjugation. An unexpected key finding was that when the mutant pPD1 plasmid (partial sequence of mutated plasmid, SEQ ID NO:1) is introduced into EF along with a second plasmid (SEQ ID NO:4) carrying a coding segment of bac21 operon proximal to bacA promoter, in this case the bacA-E gene cluster (SEQ ID NO:6), the host strain of EF retains the ability to produce the bacteriocin. In the modified bacteria of the present invention, transfer of bacteriocin production to other bacteria via conjugation does not occur at detectable frequencies, which is another advantage of our system.

The Present Invention

In brief, the present invention typically requires a first plasmid encoding Bacteriocin 21 (Bac-21), preferably the pPD1 plasmid (SEQ ID NO:10, GenBank: KT290268, which is mutated to include SEQ ID NO:2 (partial sequence of pPD1 containing the insertion seen in SEQ ID NO:1) that is transferred to a target bacterial cell by pheromone inducible conjugation. The first plasmid will typically have a mutation in the bacAB sequence (e.g. insertion of ermC gene (SEQ ID NO:2) into pPD1 (SEQ ID NO:10 (GenBank: KT290268), to produce pPD1 ΔbacAM::ermC (partial sequence of PD1 including the mutation (insertion of SEQ ID NO:2) can be found in SEQ ID NO:1)). The target bacterial cell also comprises a second plasmid that encodes a segment proximal to the bacA promoter, typically bacABCDE (e.g., pSK29 (SEQ ID NO:4), made by insertion of bacABCDE (bacA-E, SEQ ID NO:6) into pAM401 vector (SEQ ID NO:5)). The target bacterial cell is an *Enterococcal* strain, preferably *Enterococcus faecalis* or *Enterococcus faecium*, comprising a deletion of the Sortase A gene (e.g., SEQ ID NO:9 (ΔsrtA), made by deletion of SEQ ID NO:8 from the *E. faecalis* OGIRF srtA open reading frame (SEQ ID NO:7)).

In a preferred embodiment, the strain is EF ΔsrtA+pPD1::ΔbacAB bacABCDE+. In an embodiment, the EF strain comprises ΔbacAB pPD1 (partial sequence of the mutated pPD1 plasmid found in SEQ ID NO:1), pSK29 (SEQ ID NO:4) and deletion of the srtA gene (SEQ ID NO:9).

In the present invention, the pPD1 plasmid has been engineered (mutated) in such a way that when present in a cell along with a second plasmid carrying a proximal segment, such as the bacA-E gene cluster, the host EF strain has the ability to produce the bacteriocin. However, the strain is impaired in bacteriocin conjugation and long-term GI colonization. Therefore, in one embodiment, the present invention is a bacteriocin-producing strain that is inefficient at establishing long-term colonization of the GI tract, but remains capable of delivering bacteriocin efficiently to decolonize antibiotic-resistant enterococci.

The strain will preferably have a minimized potential for transfer of bacteriocin-production traits to other bacteria via conjugation. By "minimized potential", we refer to slight or no evidence for the transfer of bac operon using current methods for detection. Selection by culture techniques followed by probing for plasmid specific genes using polymerase chain reaction are the current standard methods.

Methods of Creating a Modified EF Strain

One would first choose an EF strain to modify. Preferably, one would choose *Enterococcus faecalis* or *Enterococcus faecium*. The preferred strain used for this study does not carry mobile genetic elements and is not resistant to commonly used antibiotics. However, this invention also includes other mutants and derivatives of *E. faecalis* or other *Enterococcal* strains that exhibit similar or greater efficacy in delivering Bac-21 but maintain poor colonization ability.

One would then introduce a plasmid encoding the Bac21 operon. The plasmid will typically comprise a mutation in the bacAB sequence, as described below. This mutation may be made before or after the plasmid is introduced into the target bacterial strain. A typical Bac21-encoding plasmid is pPD1 (See Tomita, H., Fujimoto, S., Tanimoto, K. & Ike, Y. Cloning and genetic and sequence analyses of the bacteriocin 21 determinant encoded on the *Enterococcus faecalis* pheromone-responsive conjugative plasmid pPD1. *Journal of bacteriology* 179, 7843-7855, 1997).

In one embodiment, the engineered EF bacteria of the present invention is created by first creating an in-frame deletion in bacAB in the target bacteria in the pPD1 backbone resulting in a pPD1 mutant plasmid (partial sequence of mutated pPD1 found in SEQ ID NO:1), which is unable to produce BAC21.

One then introduces a second plasmid construct (for example, pAM401 (SEQ ID NO:5, described below) carrying a segment proximal to the bacA promoter into the EF strain harboring the mutant pPD1. Preferably, the plasmid encodes bacABCDE (e.g., SEQ ID NO:4 including the bacA-E nucleotide sequence (SEQ ID NO:6). The pAM401 plasmid that carries bacABCDE is chloramphenicol resistant and can be referred to as the "complementing plasmid" (e.g., SEQ ID NO:4). The resulting strain that has a bacAB deletion in the pPD1 backbone (SEQ ID NO:10, partial sequence of mutated pPD1 can be found in SEQ ID NO:1) and also harbors pAM401::bacABCDE (SEQ ID NO:4) is called the "complementing strain." This strain is now able to produce BAC21.

By "a segment proximal to the bacA operon," Applicants mean a segment adjacent to the bacA promoter that includes the coding region that is required for Bac21 production but not limited to bacA and bacB genes only. Segment bacA-E is proximal to bacA promoter compared to bacF-I. We found that complementing just the bacAB segment is ineffective in restoring BAC21 production. Applicants note that the first and second plasmid may be introduced into the target host in any order.

As disclosed below, Applicants successfully colonized the GI tract of mice with the complementing strain carrying the first and the second plasmids. The modified EF strain not only out-competed other strains of EF in the mouse GI tract but also eliminated an antibiotic (vancomycin) resistant strain from the GI tract, with minimal perturbation of the composition of the overall GI microbial community. Applicants tested the strains of *enterococcus* in the GI tract for any evidence of conjugation (transfer of the bacteriocin operon or pPD1::ΔbacAB plasmid) from the complementing strain to other enterococci. No conjugation was detected. Similar experiments were performed in vitro and no conjugation was detected.

The modified strains can be cultured industrially to provide commercial quantities of the modified strain by growth under typical bacterial fermentation conditions. The modified strains may be used in compositions in the form of intact viable cells or in a viable lyophilized form.

Method of Use

We envision that this product would be used in a prophylactic manner, to eliminate GI colonization by drug-resistant (e.g., antibiotic-resistant) enterococci in patients at risk of acquiring healthcare-associated enterococcal infections. In such a scenario, live organisms of the therapeutic strain would be delivered to patients orally, potentially via suspension in a beverage or food product or in the form of lyophilized organisms formulated in a pill. One could follow prior art methods to determine a correct dosage. For example, one may consult U.S. Pat. No. 5,728,380; EP0508701, or US20070098744, the contents of which are incorporated by reference.

Other routes of administration are also contemplated that allow for the product to reach the gut lumen, e.g., but not limited to, rectally, G-tube, NG-tube, direct administration to the intestinal track (gut lumen), etc.

In one embodiment, the patient is preferably a human patient.

In addition, veterinary use of the present modified strains, products and compositions are contemplated. By veterinary use, we mean use in a non-human animal, including domesticated animals, livestock and wild animals in captivity.

Non-human animals include, but are not limited to domesticated animals, livestock and also wild animals kept in captivity (e.g., housed in zoos or sanctuaries). Domesticated animals includes, without limitation, cats, dogs, rabbits, guinea pigs, ferrets, hamsters, mice, gerbils, horses, cows, goats, sheep, donkeys, pigs, and the like. Livestock includes animals raised for production of food products, including, but not limited to, poultry, pigs, cows, buffalo, sheep, goat, and the like. Wild animals contemplated include animals that are found in the wild or housed at zoos, sanctuaries or wild-life habitats.

In a preferred embodiment, the non-human animals are birds, for example, domesticated birds, pet birds and poultry. Suitable domesticated or pet birds include, but are not limited to, for example, parakeets, cockatiels, lovebirds, pigeons, parrotlets, caiques, small conures, lories, lorikeets, canaries, parrots, crows, doves, toucans, macaws, cockatoos, and the like.

In a more preferred embodiment, the birds are poultry. Suitable poultry able to be treated by the modified strains and methods described herein include, but are not limited to, chickens, turkeys, pheasants, ducks, geese, partridge, quail and the like.

It is specifically contemplated that the methods described herein are able to reduce or eliminate enterococcal colonization (specifically antibiotic-resistant enterococcal colonization) of the GI track of poultry to be slaughtered and consumed. The ability to reduce or eliminate enterococcal colonization reduces the likelihood of the poultry to result in disease in humans.

In addition, non-human animals, including livestock, particularly chickens, are commonly colonized by enterococci, including enterococcal species that cause disease in humans (i.e., *E. faecalis* and *E. faecium*) as well as enterococcal species that cause disease in the animals themselves (i.e., *E. cecorum*). This therapeutic strategy may be used to reduce or eliminate enterococcal colonization of animals to reduce the enterococcal burden in the animal GI tract and minimize the potential for: (i) transmission of antibiotic-resistant, animal-derived enterococci (or antibiotic-resistance genes harbored by these enterococci) to humans via contamination of uncooked food products; and (ii) disease of the animal host resulting from spread of pathogenic enterococci.

A method of treating enterococci infections in a human patient in need thereof is contemplated in some embodiments. The method comprises administering to the human patient a therapeutically effective amount of the modified enterococcal strain or a composition comprising the modified strain.

Methods of treating enterococci infections in a non-human animal are also contemplated herein. The methods comprise administering to the non-human animal a therapeutically effective amount of the modified enterococcal strain or compositions described herein. In a preferred embodiment, the non-human animal is a poultry, more specifically a chicken, turkey, pheasant, quail, duck or the like. In a preferred embodiment, the non-human animal is a chicken.

The term "treat", "treating", and "treatment" of bacterial infections, including enterococcal infections, encompasses, but is not limited to, reducing, inhibiting, alleviating, improving, delaying or limiting at least one symptom of the infection, for example, may be characterized by one or more of the following: (a) reducing, slowing or inhibiting growth of drug-resistant bacteria (e.g., antibiotic-resistant enterococcal infections) within the GI track (intestine) of the animal, (b) reducing or preventing bacterial colonization of the GI track of the animal by a pathogenic or drug-resistant strain of bacteria (e.g., antibiotic-resistant enterococci), (c) reducing or eliminating enterococcal colonization of the GI track of the animal, (d) reducing the enterococcal burden in the GI track of the animal, (e) reducing or inhibiting the transmission of antibiotic-resistant, animal derived enterococci from livestock to humans, and (f) reducing or eliminating one or more symptoms of infection or GI colonization associated with drug-resistant bacteria in the animal.

The term "effective amount" or "therapeutically effective amount" as used herein refer to an amount sufficient to effect beneficial or desirable biological, therapeutic and/or clinical results. In one embodiment, the "effective amount" is an amount sufficient to reduce, inhibit, or eliminate the colonization of enterococci bacteria, e.g., antibiotic-resistant enterococci, within the GI track of an animal. An effective amount refers to the quantity of the modified strain (complementary strain) sufficient to yield a desired therapeutic response without undue adverse side effects such as toxicity, irritation, or allergic response. The specific "effective amount" will, obviously, vary with such factors as the particular condition being treated, the physical condition of the subject, the type of animal being treated, the duration of the treatment, the nature of concurrent therapy (if any), and the specific formulations employed and the structure of the compounds or its derivatives.

Those skilled in the treatment of bacterial infections, in particular enterococcal infections, will easily determine the therapeutically effective amount of the modified stain or complementary strain to be used. It may be appropriate to administer the therapeutically effective dose in the form of two or more sub-doses at appropriate intervals throughout the day.

The exact dosage and frequency of administration depends on the particular composition, the particular condition being treated, the severity of the condition being treated, the age, weight and general physical condition of the particular animal as well as the other medication, the animal may be taking, as is well known to those skilled in the art.

Suitable embodiments of the present invention provide for daily, weekly or monthly doses of the modified strain or composition described herein. In some embodiments, the strain or compositions are administered in effective daily dosages. Furthermore, in some embodiments, the effective daily amount may be lowered or increased depending on the response of the treated animal and/or depending on the evaluation of the physician or veterinarian prescribing the compounds of the instant invention. The effective daily amount ranges mentioned hereinabove are therefore only guidelines.

In some embodiments, methods of inhibiting the GI colonization by antibiotic-resistant enterococci in human patient in need thereof are contemplated. The method comprises administering to the patient a therapeutically effective amount of the modified enterococcal strain or compositions comprising the modified enterococcal strain.

In some embodiments, the modified strain and compositions are used to prophylactically to inhibit the colonization of the GI track of an animal (human or non-human) by pathogenic or drug-resistant (antibiotic-resistant) bacteria (e.g., antibiotic-resistant enterococci). The term "prophylactically" refers to the ability to inhibit the colonization of the GI track with pathogenic or drug-resistant bacteria or to prevent or inhibit the overgrowth of pathogenic or drug-resistant bacteria within the GI track of the animal.

Another embodiment contemplates methods of altering the microbial composition of the GI track of a human or non-human animal or patient, the method comprising administering to the human or non-human animal or patient a therapeutically effective amount of the modified enterococcal strain or the compositions described herein in order to alter the microbial composition of the GI track. "Altering the microbial composition of the GI track" refers to the ability to alter the composition and make-up of the microbes inhabiting the GI track. In a preferred embodiment, the GI track is altered to have one or more of the following characteristics: (a) increase in the amount of beneficial bacteria within the GI track, (b) increase in the ratio of beneficial bacteria to drug-resistant bacteria (e.g., greater that 2:1 ratio), (c) reduce or decrease the amount of drug-resistant (e.g., antibiotic-resistant) bacteria within the GI track. In some preferred embodiments, the non-human animal is a poultry, for example, but not limited to, a chicken.

Further embodiments describe methods of preventing GI track colonization of antibiotic resistant enterococci in a human patient comprising administering to the patient a therapeutically effective amount of the modified enterococcal strain or composition described herein to prevent GI track colonization.

Some embodiments describe a method of treating enterococci infections in a non-human animal comprising administering to the non-human animal a therapeutically effective amount of the modified enterococcal strain or compositions described herein in order to treat the enterococci infection. In some embodiments, the preferred non-human animal is a poultry, in some embodiments, a chicken.

In some embodiments, methods of preventing GI track colonization of antibiotic resistant enterococci in a non-human animal are contemplated. Preventing GI track colonization encompasses the ability to prevent the overgrowth of antibiotic resistant enterococci in the GI track, as demonstrated by a reduced number or a reduced ratio of antibiotic resistant enterococci to non-harmful bacteria within the GI track. The method comprises administering an effective amount of the modified strain or compositions described herein in order to prevent GI track colonization.

The methods of administration described herein may be done in a single dose or over multiple dosages over a number of days, weeks or months depending on the treatment necessary. In some embodiments, the methods are performed daily. Daily administration includes single administration or multiple administrations within the day to provide the effective amount. In other embodiments, administration is performed weekly or monthly.

In another embodiment, the disclosure provides a method of reducing contamination of livestock food products with antibiotic-resistant enterococci. The method comprises administering to the livestock before slaughter an effective amount of the modified enterococcal strain or the composition described herein in an amount effective to reduce the amount of antibiotic-resistant enterococci in the GI track of the livestock. The reduction of antibiotic-resistant enterococci in the GI track of livestock, in turn reduces the contamination of livestock food products when the livestock is slaughtered and prepared for consumption. In some embodiments, the complementary strain (modified strain) or composition described herein is administered at least once prior to slaughter of the livestock. In other embodiments, the complementary strain (modified strain) or composition described herein may be administered over multiple days or weeks prior to slaughter. In one embodiment, the livestock are administered the complementary strain (modified strain) or composition described herein for at least two days prior to slaughter, alternatively for at least three days prior to slaughter, alternatively for at least four days prior to slaughter, alternatively for at least five days prior to slaughter, alternatively for at least six days prior to slaughter, alternatively for at least seven days prior to slaughter, alternatively for at least 2 weeks prior to slaughter, alternatively for at least 3 weeks prior to slaughter, alternatively for at least 4 weeks prior to slaughter. One skilled in the art will be able to determine the correct administration in order to reduce the contamination of livestock food product by reducing or eliminating the enterococci colonization in the GI track of the livestock animal.

In a preferred embodiment, the disclosure provides a method of reducing contamination of poultry food products with enterococci, more specifically antibiotic-resistant enterococci. The method comprises administering to the poultry before slaughter an effective amount of the modified enterococcal strain or the composition described herein in an amount effective to reduce or eliminate the amount of antibiotic-resistant enterococci in the GI track of the poultry. The reduction of antibiotic-resistant enterococci in the GI track of the poultry, in turn reduces the contamination of poultry food products when the poultry is slaughtered and prepared for consumption. In a preferred embodiment, the poultry is a chicken.

Compositions

The modified strains disclosed herein can be formulated into compositions, include feed compositions. Feed compositions include feed compositions for human consumption or non-human animal consumption. Food compositions for human consumption are any compositions formulated for ingestion by a human being. Suitable non-human compositions include, for example livestock feed, pet food, pet food compositions, animal food, animal food compositions, which are intended for ingestion by a non-human animal.

Another embodiment of the present invention is feed compositions and methods of producing feed composition for non-human animals (e.g., livestock or domesticated animals). The feed composition comprising the modified enterococcal strain (e.g., complementing strain carrying the first and second plasmids) may be formulated using at least one animal feed product. The feed composition is made by mixing a sufficient amount of the modified enterococcal stain with feed product or water. In some embodiments, the resulting mixture is granulated and/or dried to obtain a powder, pellets, granules, gels or other solid forms of feed. In other embodiments, the feed composition is provided in a gel or water composition. In some embodiments, the modified strain is lyophilized before being added to the feed product to provide solid forms of the feed composition. This feed composition may be a solid formulation or liquid formulation that may further comprise one or more compatible carriers or diluents. In a preferred embodiment, the feed composition is suitable for poultry (e.g., poultry feed). In some embodiments, the feed is chicken feed.

In some embodiments, the modified strain is formulated into compositions comprising a pharmaceutically acceptable carrier. Suitable carriers are carriers that do not affect the viability of the modified strain within the composition. Suitable formulations of the composition may be used for veterinary use and administration, or for human use and administration.

In some embodiments, the modified strains are formulated into compositions as dietary supplements for human or non-human animal consumption or in treatment formulations. In some embodiments, the dietary supplements are contemplated to be ingested in addition to the normal diet of the animal.

Suitable examples of compositions for use as a dietary supplement, include, but are not limited to, for example, a gravy, drinking water, beverage, liquid concentrate, yogurt, powder, granule, paste, suspension, chew, morsel, treat, snack, pellet, pill, capsule, tablet, or any other delivery form. The dietary supplements can be specially formulated for consumption by a particular animal. In one detailed embodiment, the dietary supplement can comprise a high concentration of complementary strain such that the supplement can be administered to the animal in small amounts, or in the alternative, can be diluted before administration to an animal. The dietary supplement may require admixing with water or a suitable diluent prior to administration to the animal.

The composition may be refrigerated or frozen. The modified strains may be pre-blended with the other components of the composition to provide the beneficial or effective amounts needed, may be coated onto a food composition, dietary supplement, or food product formulated for human or non-human consumption, or may be added to the composition prior to offering it to the human or non-human animal, for example, using a powder or a mix.

Food compositions may be formulated in one embodiment in to contain the modified strains in the range of about $10^2$ to about $10^{11}$ colony forming units (CFU) per gram of the composition. Dietary supplements may be formulated to contain several fold higher concentrations of the modified strain, to be amenable for administration to an animal in the form of a tablet, capsule, liquid concentrate, or other similar dosage form, or to be diluted before administration, such as by dilution in water or diluent, spraying or sprinkling onto a food, and other similar modes of administration.

In another embodiment, the composition comprising the modified enterococcal stain may be formulated for administration with the animal feedstuff as a concentrated feed additive or a premix may be prepared with the normal animal feed.

Aspects of the present disclosure that are described with respect to methods can be utilized in the context of the compositions or kits discussed in this disclosure. Similarly, aspects of the present disclosure that are described with respect to the compositions can be utilized in the context of the methods and kits, and aspects of the present disclosure that are described with respect to kits can be utilized in the context of the methods and compositions.

This disclosure provides kits. The kits can be suitable for use in the methods described herein. In one embodiment, the kit comprises the modified strain and instructions for use. The instructions may provide recommended modes of administration to the human or non-human animal, including, but not limited to, specifying dosage, quantity and frequency of administration.

In some embodiments, the present disclosure provides a kit for mixing the modified stain of enterococci with non-human animal feed to make animal feed composition for animal consumption. The kit may include instructions on the ration of modified strain to animal food product and methods of mixing suitable for administration.

It should be apparent to those skilled in the art that many additional modifications beside those already described are possible without departing from the inventive concepts. In interpreting this disclosure, all terms should be interpreted in the broadest possible manner consistent with the context. Variations of the term “comprising” should be interpreted as referring to elements, components, or steps in a non-exclusive manner, so the referenced elements, components, or steps may be combined with other elements, components, or steps that are not expressly referenced. Embodiments referenced as “comprising” certain elements are also contemplated as “consisting essentially of” and “consisting of” those elements. The term “consisting essentially of” and “consisting of” should be interpreted in line with the MPEP and relevant Federal Circuit’s interpretation. The transitional phrase “consisting essentially of” limits the scope of a claim to the specified materials or steps “and those that do not materially affect the basic and novel characteristic(s)” of the claimed invention. “Consisting of” is a closed term that excludes any element, step or ingredient not specified in the claim.

The following non-limiting examples are included for purposes of illustration only, and are not intended to limit the scope of the range of techniques and protocols in which the compositions and methods of the present invention may find utility, as will be appreciated by one of skill in the art and can be readily implemented. The present invention has been described in terms of one or more preferred embodiments, and it should be appreciated that many equivalents, alternatives, variations, and modifications, aside from those expressly stated, are possible and within the scope of the invention.

EXAMPLES

Materials and Methods

Bacterial Strains Growth Media and Reagents.

The strains used in this study are listed in Table 1. Brain-heart infusion medium (BHI) and m-*Enterococcus* agar (Ent-agar) (Difco) were prepared as described by the manufacturer (Becton Dickinson). Antibiotics were purchased from Sigma and used at the following concentrations: rifampicin, 200 g ml-1; spectinomycin, 500 g ml-1; chloramphenicol, 15 g ml-1. *E. faecalis* was cultured in BHI media at 37° C. All restriction enzymes were purchased from New England BioLabs. Phusion High-Fidelity DNA Polymerase (Thermo Scientific) was used for all PCRs performed for strain and plasmid construction. Oligonucleotides were synthesized by Fisher Scientific.

TABLE 1

| | Description | Reference or source |
|---|---|---|
| Strains | | |
| OG1sp | Spontaneous mutant of OG1; $Sp^r$ | 9 |
| OG1RF | Spontaneous mutant of OG1; $Rif^r$, $Fa^r$ | 9 |
| JL277 | 1,231,501 rpoB H486Y; $Rif^r$ derivative | 9 |
| IB1 ($V583_r$) | V583 spontaneous $Rif^r$ derivative, $Van^r$ | 9 |
| IB10($\Delta srtA_r$) | OG1RF ΔsrtA | unpublished |
| IB16 ($\Delta srtA_s$) | OG1SP ΔsrtA | unpublished |
| CK119 | OG1RF ΔireK | 26 |
| SK7 | OG1RF ΔdhAK (inframe Deletion in OG1RF_11146 to OG1RF_11149) | unpublished |
| IB10 pPD1 | OG1RF ΔsrtApPD1 | This study |
| SK16 pSK33 | OG1RF ΔsrtA pPD1:: ΔbacAB | This study |
| SK17 pSK33 | OG1SP ΔsrtA pPD1:: ΔbacAB | This study |
| SK16 pSK33 pSK29 | OG1RF ΔsrtA pPD1:: ΔbacAB pAM401::bacABCDE+ | This study |

TABLE 1-continued

| | Description | Reference or source |
|---|---|---|
| SK17 pSK33 pSK29 | OG1SP ΔsrtA pPD1:: ΔbacAB pAM401::bacABCDE+ | This study |
| Plasmids | | |
| pPD1 | Bac-21, pheromone-inducible conjugative plasmid | 9 |
| pSK33 | ΔbacAB::ermC in pPD1 | 9 |
| pSK29 | bacABCDE in pAM401 | 9 |
| pCJK218 | *E. faecalis* allelic exchange vector (Cmr); pheS* counterselection | 20 |
| pCJK245 | *E. faecalis* allelic exchange vector (Cmr); thyA* counterselection | 21 |

Animals.

The committee for animal care and use at the Medical College of Wisconsin approved all animal-related procedures and experiments. Five-week-old male C57Bl/6 mice were obtained from Jackson Laboratories (West-RB08 barrier). Upon arrival, mice were allowed to adapt to the new environment for at least one week before the start of any experiment. Animals were housed under specific-pathogen-free conditions in the Medical College of Wisconsin vivarium. Experimental sample sizes were determined by appropriate husbandry considerations as determined by the Medical College of Wisconsin vivarium and experiments were repeated as described. No blinding was performed, and no scheme of randomization was applied when allocating mice for the experiments.

Generation of ΔsrtA and ΔdhaK Mutants.

In-frame deletion mutants in *E. faecalis* were constructed using markerless allelic exchange as previously described[20,21]. Mutant alleles were constructed and introduced into pCJK218 or pCJK245 using Gibson assembly[22]. To ensure unperturbed expression of neighboring genes, 5' and 3' end codons of the gene were retained in each deletion allele.

Generation of ΔsrtA+pPD1 and ΔsrtA+pPD1::ΔbacAB bacABCDE+.

pPD1 was introduced into the EF ΔsrtA mutant (IB10; $\Delta srtA_R$ and IB16; $\Delta srtA_s$) via conjugation using a donor strain; WT+pPD1 (OG1SP+pPD1 or OG1RF+pPD1 respectively). The resulting transconjugants are ΔsrtA+pPD1. To construct ΔsrtA+pPD1::ΔbacAB bacABCDE+, markerless allelic exchange was used to introduce in-frame deletion of srtA in OG1RF+pPD1::ΔbacAB bacABCDE+ or OG1SP+pPD1::ΔbacAB bacABCDE+ strains, as previously described[21]. PCR analysis and bacteriocin assay confirmed the resulting strains.

Bacteriocin Assays.

As previously described[23], bacteriocin-producing or bacteriocin-sensitive indicator strains are spotted on BHI agar and incubated at 37° C. for 30 minutes to dry the spots. 50 μl of an overnight culture of the indicator strain (OG1RF or OG1sp) grown in BHI broth was added to 5 ml of molten BHI soft agar to overlay evenly onto the BHI agar containing spots of test strains. Zones of inhibition of the susceptible strain around the test strain spots were monitored after overnight incubation at 37° C.

Mouse Colonization Studies.

As previously described[9], overnight cultures of *E. faecalis* with appropriate antibiotics were washed with sterile water and added to autoclaved water to a final concentration of $5\times10^8$ CFU ml-1. Persistence of *E. faecalis* in drinking water was determined daily and remained between $10^7$ and $10^8$ CFU ml-1 over three days. Drinking water was changed every 3-4 days to maintain the appropriate inoculum and mice were allowed to drink ad libitum. After two weeks, the inoculated drinking water was replaced with sterile water for the duration of the experiment. For the sequential colonization experiment, mice were first colonized with an initial strain by feeding the bacteria through drinking water for two weeks. Three days after the initial strain was withdrawn from drinking water, the challenger strain was introduced in the drinking water for two weeks, after which animals were returned to regular sterile water (day 0).

Bacterial Culture and Quantification of EF from Mouse Feces and Intestines.

Indigenous enterococcal levels in all experimental animals were determined by culturing feces on m-*Enterococcus* agar (Ent-agar) to determine baseline colonization levels prior to introducing the experimental strain. Abundance of the experimental strain in feces and homogenized tissue samples were enumerated as previously described on BHI agar plates with appropriate antibiotics[9]. To enumerate indigenous enterococci or total enterococci, fecal and tissue homogenates were plated in serial dilution on m-*Enterococcus* agar (Difco).

In-Vitro Conjugation Assay.

Donor (rifampicin resistant strains) and recipient (spectinomycin resistant WT; OG1SP) strains were grown separately in BHI media at 37° C. for 16 hours. The cell cultures were diluted 1:5 in fresh media to use for subsequent inoculation. Donor and recipient cell cultures were mixed at 1:9 ratios. Samples for serial dilution were taken 24 h after the start of the experiment Evidence of conjugation was observed by screening transconjugants via colony PCR. To determine transconjugants, colonies were selected and used as PCR templates for identification of the bacA or bacD gene using gene-specific primers as previously described[9]. PCR products were identified using agarose gel electrophoresis.

Results and Discussion

Our previous work provided proof-of-concept that EF can deliver bacteriocin to specifically eliminate multidrug-resistant enterococci from the GI tract[9,18]. However, one potential caveat to this approach is that the bacteriocin delivery strain itself will take up residence in the intestinal tract and may eventually acquire additional antibiotic resistance traits through horizontal genetic exchange, re-creating the original problem. To overcome this obstacle, we sought to engineer a bacteriocin-producing strain that is inefficient at establishing long-term colonization of the GI tract, but remains capable of delivering bacteriocin efficiently to decolonize antibiotic-resistant enterococci. An additional consideration was to minimize the potential for transfer of bacteriocin-production traits to other bacteria via conjugation.

We began by examining several factors encoded in the core EF genome that we hypothesized, based on our unpublished studies and previously published work, to be important for colonization and persistence of EF in the GI tract. These included Sortase A (SrtA, OG1RF_12327), IreK (OG1RF_12384), and the DhaK pathway (OG1RF_11146-11149). SrtA is a key membrane-anchored transpeptidase that mediates attachment of proteins to the cell-surface. Several studies on sortase[24,25] and associated cell-wall proteins (unpublished data) provided evidence for their roles in bacterial physiology in response to the extracellular environment. Moreover, SrtA is important for the establishment of enterococcal urinary tract infections[25]. Collectively, these observations suggest that SrtA might also play a role in interactions with components of the intestinal milieu during GI colonization. IreK is a transmembrane kinase required for intrinsic enterococcal resistance to antimicrobial stresses that affect the cell envelope, including stresses likely to be encountered in the GI tract such as lysozyme and cholate[26]. A preliminary study indicated that IreK contributed to short-term persistence in the mouse GI tract[26], and recently a role for IreK in stable GI colonization has been described (Banla et al, (2017) Infect. Immun. 86(1). pii: e00381-17. doi: 10.1128/IAI.00381-17). The DhaK pathway mediates glycerol utilization by EF and is upregulated in the intestinal environment[27] (unpublished data), suggesting that adaptation of metabolism is required for GI colonization. Individual mutants of EF (ΔsrtA, ΔireK, or ΔdhaK) lacking these factors exhibited a reduced ability to colonize the GI tract compared to the wild-type (WT) (FIG. 1), documenting a role for each as an enterococcal GI colonization factor.

Figures 2A, 2B:
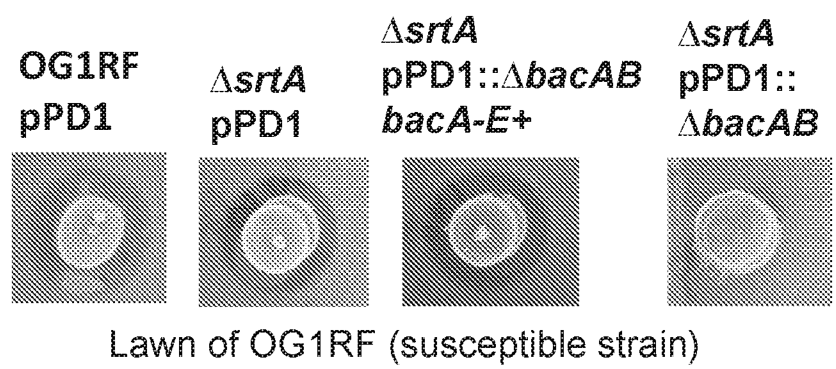
FIG. 2A is a bacteriocin assay by the soft agar method, with WT+pPD1 (OG1RF pPD1), Δ srtA+pPD1, ΔsrtA+pPD1::ΔbacAB bacA-E+ and ΔsrtA+pPD1::ΔbacAB. Susceptible *E. faecalis* (WT; OG1RF) in soft agar was overlaid on spotted test strains. Zone of clearance around the test strains indicates the bacteriocin activity against the susceptible strain.
FIG. 2B is the summary of the conjugation assay. Four independent cultures of rifampicin resistant WT+pPD1, ΔsrtA+pPD1, ΔsrtA+pPD1::ΔbacAB, bacABCDE+, and ΔsrtA+pPD1::ΔbacAB were mixed with spectinomycin resistant WT (OG1SP) in BHI broth at a ratio of 1:9. Samples for serial dilution were taken 24 h after the start of the experiment Evidence of conjugation was observed by screening transconjugants via colony PCR. Numerator represents the number of transconjugants observed after screening indicated number (Denominator) of spectinomycin resistant clones. Data are representative of two biologically independent experiments. * indicates colony PCR probed for bacA gene; ** indicates colony PCR probed for bacD gene.

An EF strain defective in GI colonization must retain the ability to produce Bac21 to be therapeutically effective. To assess this capacity, we focused on the ΔsrtA mutant First, we constructed a ΔsrtA mutant carrying two plasmids that, when present together, enable Bac-21 production by the host EF strain[9]. EF ΔsrtA+pPD1::ΔbacAB bacABCDE+(therapeutic strain) was effective at inhibiting growth of susceptible EF both in liquid culture (data not shown) and on solid media in vitro (FIG. 2A), similar to WT+pPD1 (OG1RF+pPD1) and ΔsrtA+pPD1, confirming that the ΔsrtA mutation does not impact the ability of the EF strain to produce Bac-21. The benefit of using two separate plasmids to encode the bacteriocin is threefold: first, the ΔbacAB mutant of pPD1 exhibits reduced ability to transfer by conjugation[9]; second, because the bacteriocin production operon is separated into 2 independent loci the chances of transferring Bac-21 production capability to other EF strains is reduced (as it would require simultaneous transfer of both loci); and third, growth in the intestine leads to spontaneous loss of one of the plasmids (FIG. 3), leaving an EF strain carrying only pPD1::ΔbacAB, which we have previously shown to exhibit a defect in intestinal persistence[9].

To confirm that conjugation was impaired in the ΔsrtA mutant, we performed conjugation assays in vitro. The therapeutic strain was severely impaired in its ability to transfer pPD1::ΔbacAB to the recipient strain (FIG. 2B), as desired. Two factors contribute to the impaired conjugation ability in this strain: first, although the mechanism is unclear, we previously found that pPD1::ΔbacAB is inherently unable to transfer by conjugation efficiently[9]; second, SrtA was previously shown to be important for cell-cell aggregation and conjugation[28].

Figure 1B:
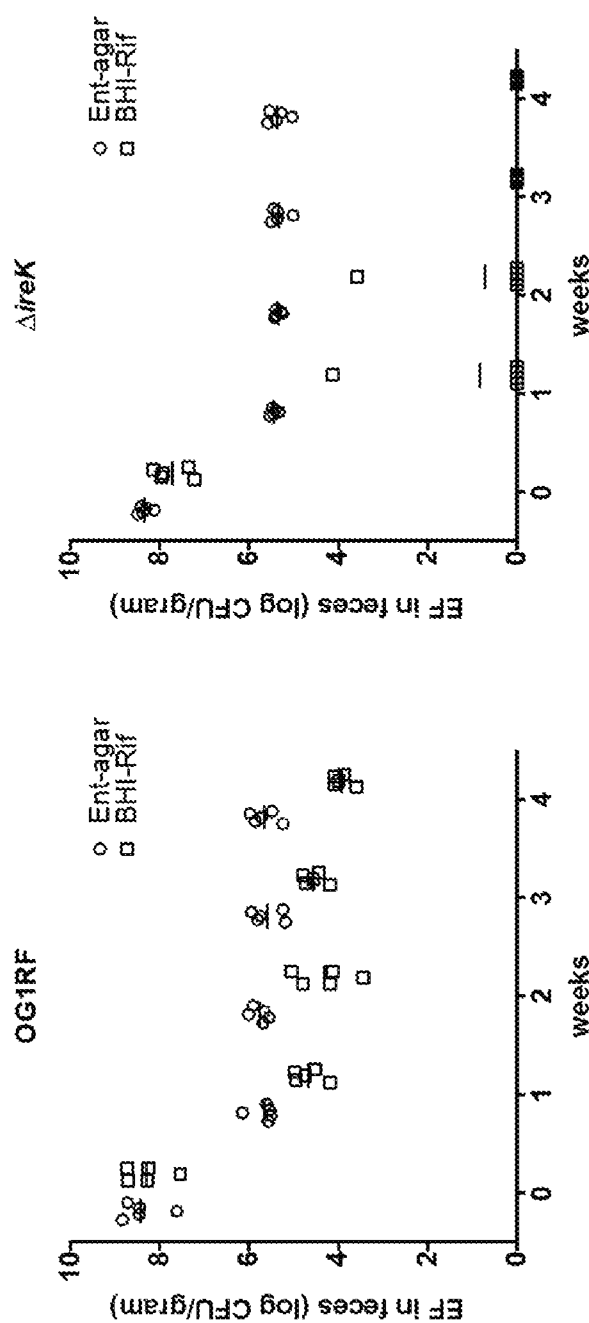
FIG. 1B is a graph evaluating mice colonized with EF. Mice (N=5 per group) were given rifampicin resistant EF (OG1RF;WT or ΔireK) for 14 days, at which time all mice were given sterile water (Week 0). After withdrawal of EF from drinking water, fecal samples were collected and abundance of enterococci was determined by enumeration on m-*Enterococcus* selective agar (Ent agar), and BHI agar with rifampicin (Rif). The results shown are representative of two independent experiments. Horizontal lines indicate geometric mean. Each symbol represents an individual animal. The limit of detection is 100 CFU per g feces.
Figure 1C:
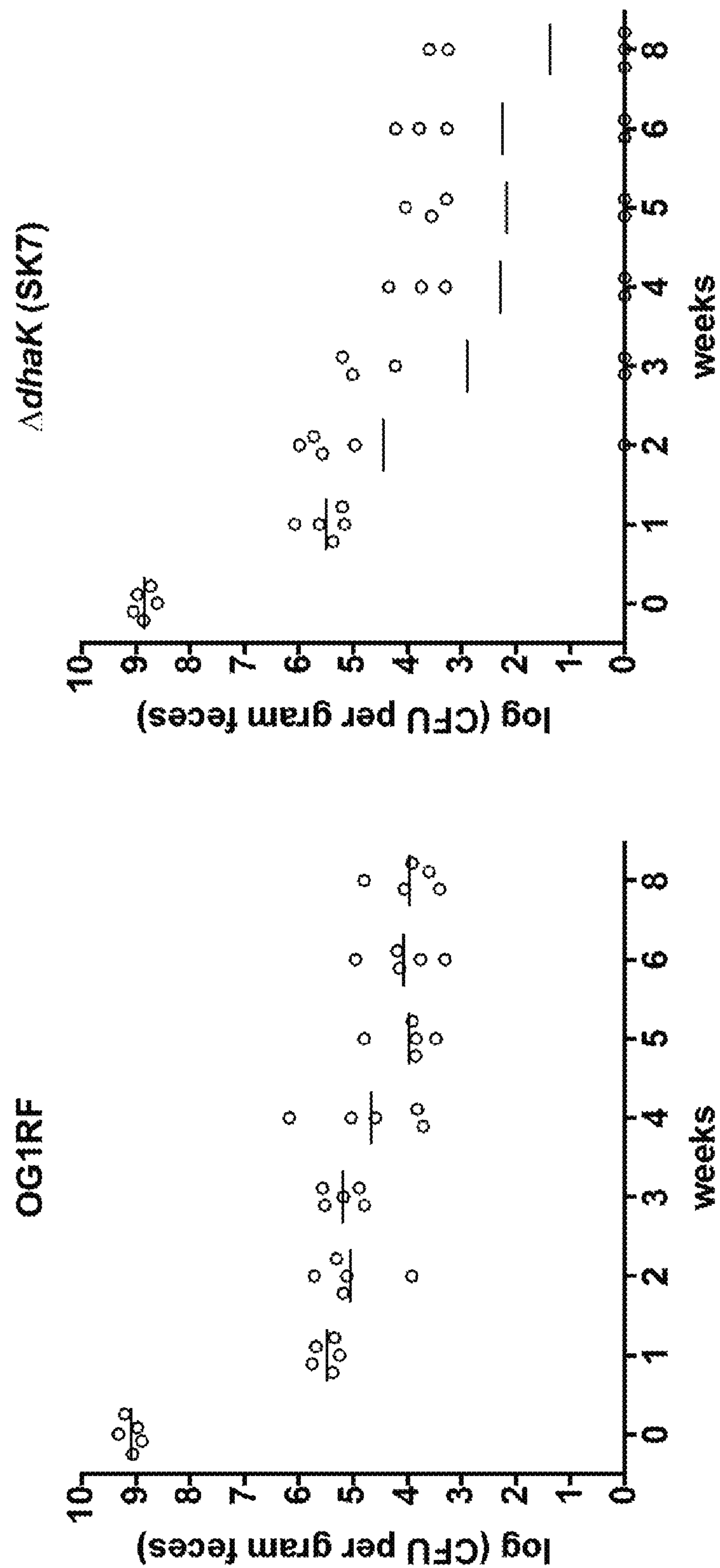
FIG. 1C is a graph evaluating mice colonized with EF. Mice (N=5 per group) were given rifampicin resistant EF (OG1RF; WT or ΔdhaK) for 14 days, at which time all mice were given sterile water (Week 0). After withdrawal of EF from drinking water, fecal samples were collected and abundance of enterococci was determined by enumeration on m-*Enterococcus* selective agar (Ent agar), and BHI agar with rifampicin. The results shown are representative of two independent experiments. Horizontal lines indicate geometric mean. Each symbol represents an individual animal. The limit of detection is 100 CFU per g feces.
Figure 3:
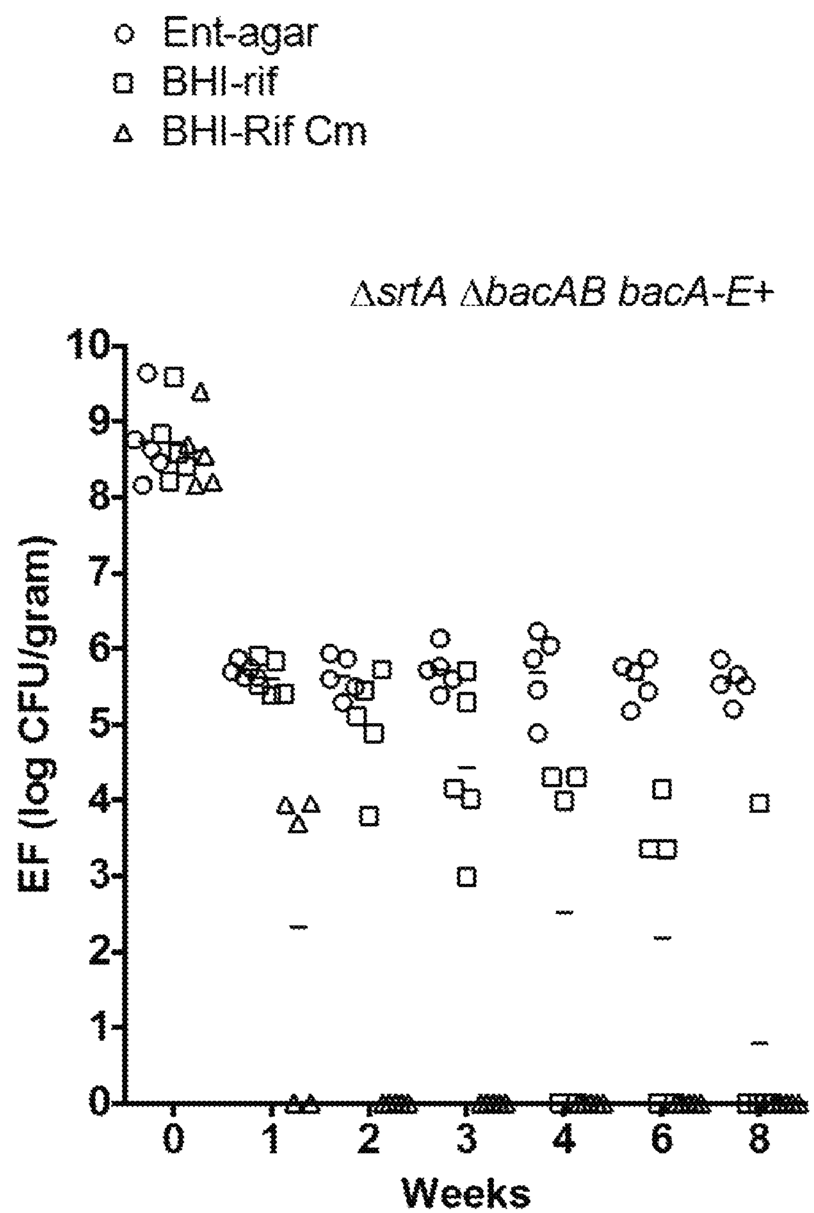
FIG. 3 is a graph demonstrating impaired ability of one embodiment of the modified strain of the present invention to establish GI colonization. Mice (N=5) were given $\Delta srtA_r$ (rifampicin resistant)+pPD1:: ΔbacAB bacA-E+ as described in the methods and abundance was determined by enumeration on m-*Enterococcus* (Ent) agar and BHI agar with rifampicin (BHI-Rif). The presence of pAM401A:: bacA-E+(complementing plasmid) was determined by enumerating CFU on BHI agar with rifampicin and chloramphenicol (BHI-Rif Cm). Fecal samples were obtained weekly after transition to sterile drinking water. Horizontal lines indicate geometric means. Each symbol represents an individual animal and data are representative of two biologically independent experiments. The limit of detection is 100 CFU per g feces.
Figures 4A, 4B:
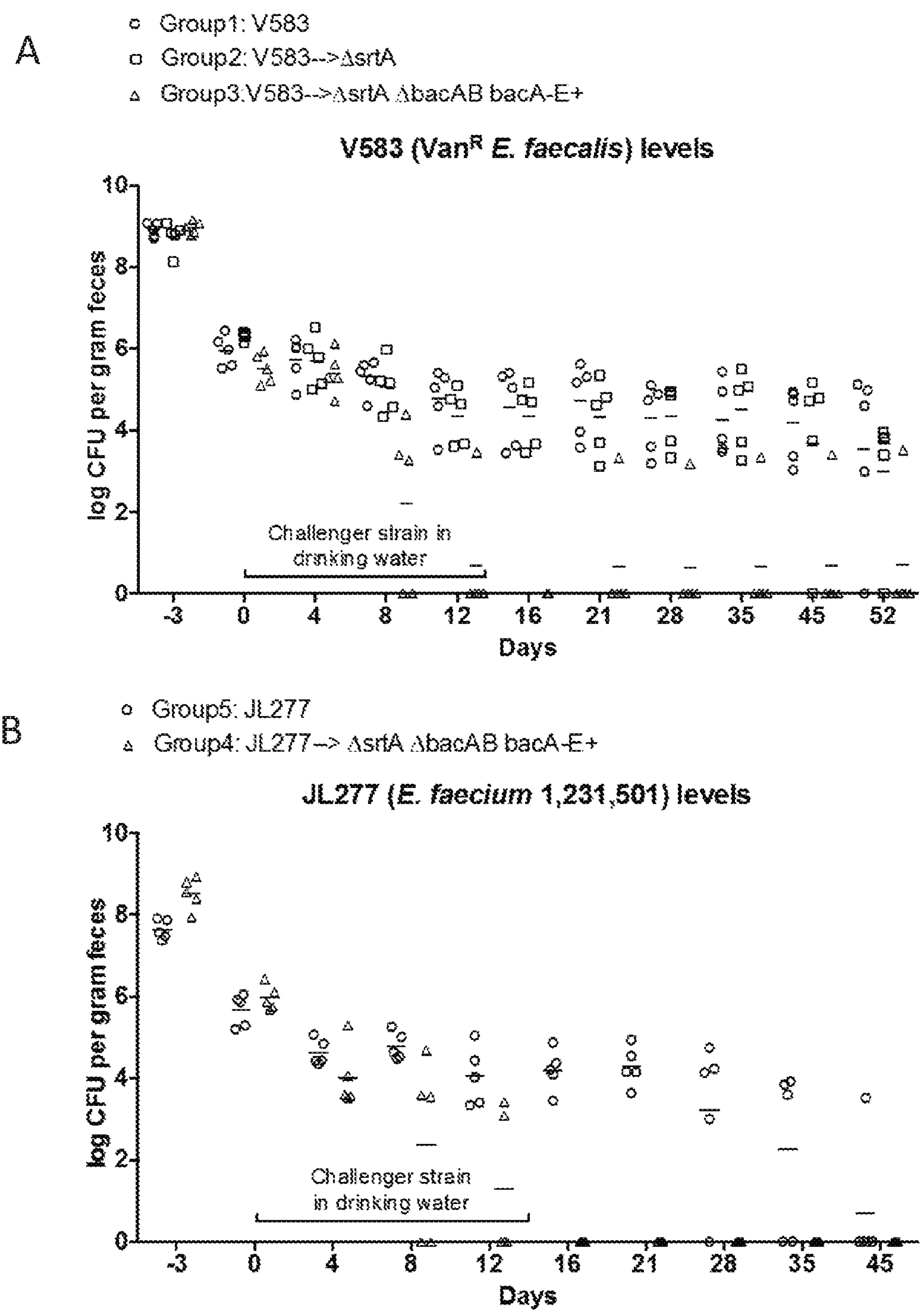
FIGS. 4A-4B are graphs graph showing an evaluation of mice that had been pre-colonized with vancomycin-resistant EF or with *E. faecium*. Mice (N=5 per group) were colonized with V583r (A) and JL277 (B; *E. faecium* 1,231,501). V583r and JL277 were removed from the drinking water of both groups two weeks before sampling (Day −3). Group 1 (A) and group 5 (B) received sterile water, whereas group 2 received ΔsrtAs (spectinomyicn resistant) (A). Group 3 (A); group 5 (B) received $\Delta srtA_s$+pPD1:: ΔbacAB bacA-E+ in their drinking water for two additional weeks, followed by sterile water at day 0. Fecal levels of V583r (A) and JL277 (B) were enumerated every few days. Each symbol represents an individual animal. The limit of detection is 100 CFU per g feces. The Challenger strain refers to $\Delta srtA_s$(group2) or $\Delta srtA_s$+pPD1:: ΔbacAB bacA-E+(Group3 and 4).

The improved "therapeutic" strain we developed (ΔsrtA+pPD1::ΔbacAB bacABCDE+) therefore exhibits multiple desirable properties: production of Bac21 (FIG. 2), impaired ability to conjugate (FIG. 2), and impaired ability to establish stable GI colonization (FIGS. 1, 3). To examine the ability of this strain to eliminate drug-resistant enterococci from the GI tract, we delivered it to mice that had been pre-colonized with vancomycin-resistant *E. faecalis* (V583) or a clinical isolate of *E. faecium* (JL277; 1,231,501) (FIG. 4). Compared to the control group, V583 and *E. faecium* levels in the challenged mice were below the detection limit in most of the animals after treatment with the improved therapeutic strain (FIG. 4). In addition to clearing the MDR-strains of enterococci, this therapeutic strain would eventually be lost due to its inability to persist longer (anticipated result; FIG. 4).

In this study, we expanded on our initial findings to develop an *E. faecalis* strain with the potential to be a useful therapeutic in humans and animals with the following traits: able to secrete Bac-21, unable to transfer bacteriocin-producing trait to other bacteria, and unable to maintain long-term colonization in the GI tract itself.

This invention can be extended to other mutants and derivatives of *E. faecalis* that exhibit similar or greater efficacy in delivering Bac-21 but maintain poor colonization ability. We envision that this product would be used in a prophylactic manner, to eliminate GI colonization by antibiotic-resistant enterococci in patients at risk of acquiring healthcare associated enterococcal infections. In such a scenario, live organisms of the therapeutic strain would be delivered to patients orally, potentially via suspension in a beverage or food product, or in the form of lyophilized organisms formulated in a pill. In addition, livestock, particularly chickens, are commonly colonized by enterococci. This therapeutic strategy also has the potential to be used to eliminate enterococcal colonization of food animals prior to harvest and processing to reduce the enterococcal burden in the animal GI tract and minimize the potential for transmission of antibiotic-resistant, animal-derived enterococci (or antibiotic-resistance genes harbored by these enterococci) to humans via contamination of uncooked food products.

Figure 5:
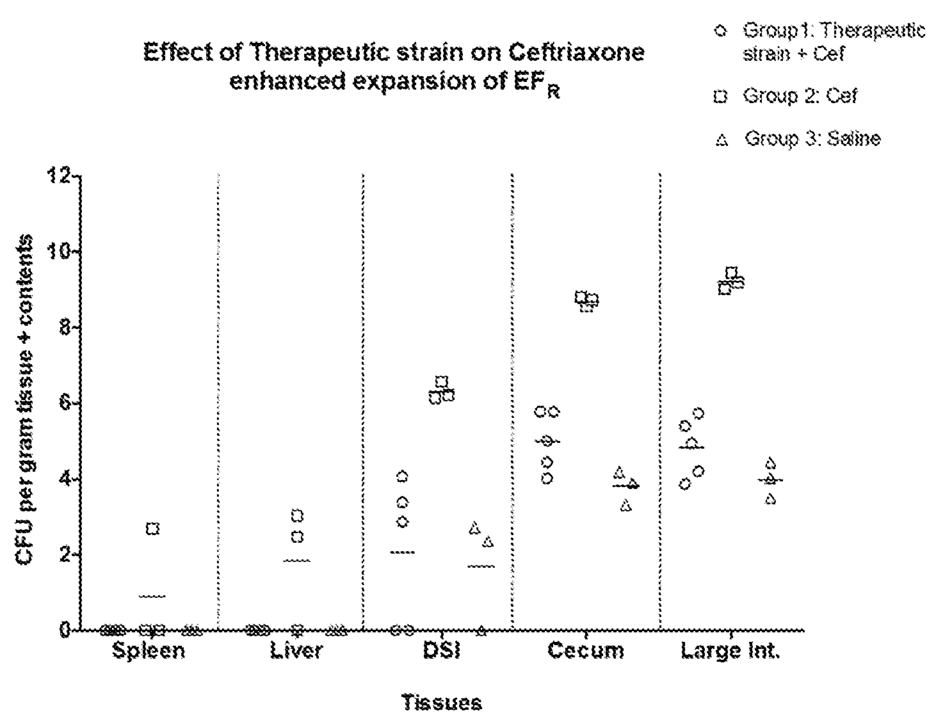
FIG. 5 diagrams the effect of the therapeutic strain on Ceftriaxone enhanced expansion of $EF_r$. Mice (N=3 for group 2 & 3; N=5 per group for 1) were colonized with $EF_r$. Group 1 & 2 received intraperitoneal injection of ceftriaxone for two consecutive days. Group 3 was administered saline (control). Group 2 & 3 were maintained on sterile water. Group 1 received $\Delta srtA_s$+pPD1:: ΔbacAB bacA-E+(therapeutic strain) in their drinking water 24 hours prior to ceftriaxone administration and continued to receive therapeutic strain until the end. Four days after the ceftriaxone treatment, animals were euthanized to determine the $EF_R$ levels in the tissues. Each symbol represents an individual animal. The limit of detection is 100 CFU per g feces.

Enterococci are intrinsically resistant to broad-spectrum cephalosporin antibiotics. They expand in the gut and disseminate systemically causing infections in immunocompromised individuals and hospitalized patients undergoing cephalosporin therapy. We examined the effect of this improved therapeutic strain on the antibiotic expansion of $EF_R$ (V583 and OG1RF). To the mice that were pre-colonized with $EF_R$, the therapeutic strain was delivered in drinking water 24 hours prior to the administration of ceftriaxone and continued until the end. As demonstrated in FIG. 5, the expansion of $EF_R$ was compared to the control groups that were not treated with therapeutic strain but, received ceftriaxone or saline respectively (group 2 and 3). $EF_R$ expansion was 4-fold lower in therapeutic treated—ceftriaxone-treated mice (group 1), compared to the group 2. In addition, dissemination of $EF_R$ and the therapeutic strain to the spleen and liver was not observed. This observation suggests that our modified therapeutic strain has the potential to minimize the antibiotic (ceftriaxone)-induced expansion of $EF_R$ and prevent the chance of translocation of enterococci across the GI barrier.

Figure 6:
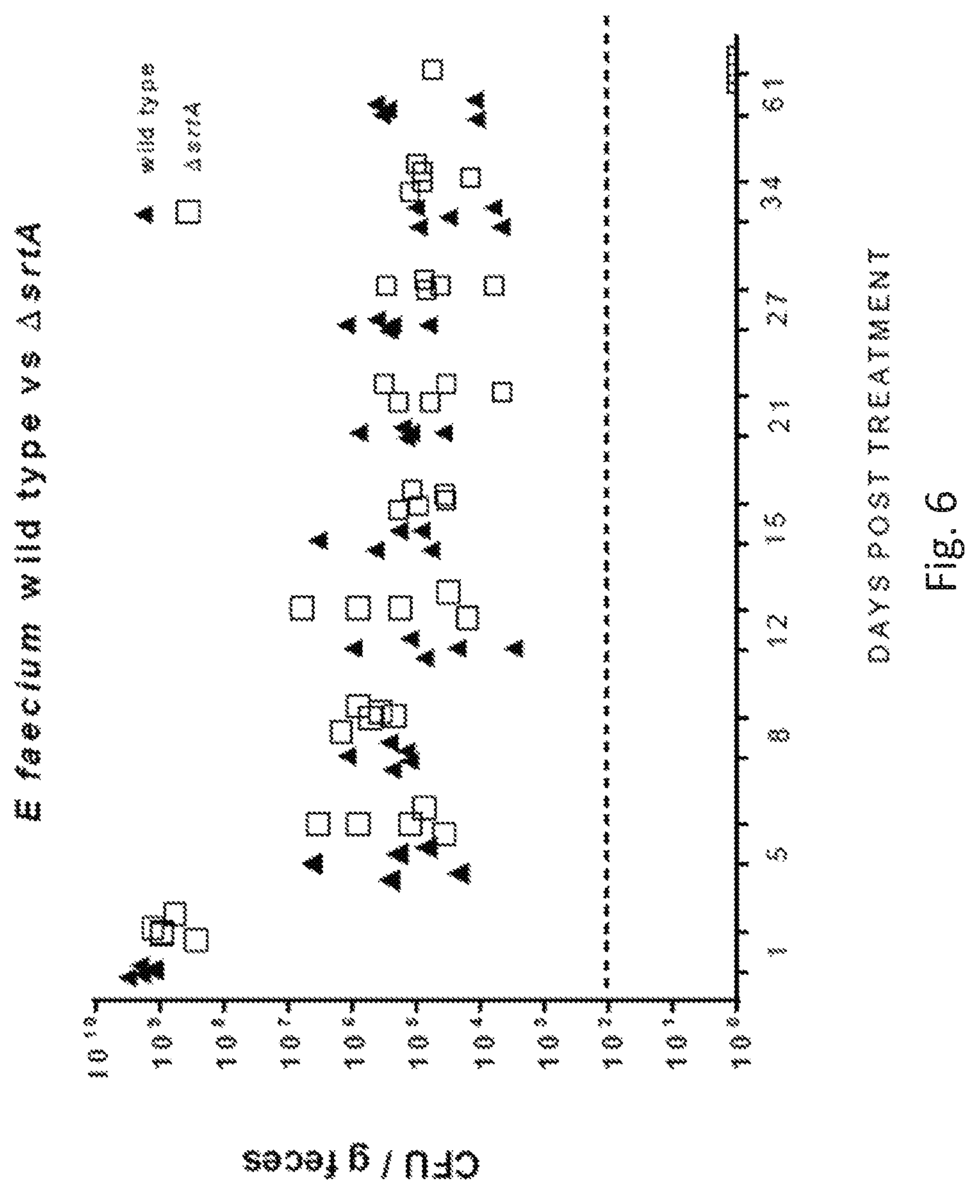
FIG. 6 demonstrates that an *E. faecium* ΔsrtA mutant is unable to establish stable colonization of the mouse gut. Each symbol represents an individual animal. The limit of detection is 100 CFU per g feces.

As demonstrated in FIG. 6, an *E. faecium* ΔsrtA mutant is unable to establish stable colonization of the mouse gut. Gut colonization was monitored in mice (N=5 per group). Fecal samples were collected and abundance of enterococci was determined by enumeration on BHI agar with rifampicin (the *E. faecium* strains were marked with rifampicin resistance). Each symbol represents an individual animal. The limit of detection is 100 CFU per g feces.

REFERENCES

1. Perez R H, Zendo T, Sonomoto K: Novel bacteriocins from lactic acid bacteria (LAB): various structures and applications. *Microbial cell factories* 2014, 13 Suppl 1:S3.
2. Cotter P D, Ross R P, Hill C: Bacteriocins—a viable alternative to antibiotics? *Nat Rev Microbiol* 2013, 11(2): 95-105.
3. Ahmad V, Khan M S, Jamal Q M, Alzohairy M A, Al Karaawi M A, Siddiqui M U: Antimicrobial potential of bacteriocins: in therapy, agriculture and food preservation. *Int J Antimicrob Agents* 2016.
4. Dobson A, Cotter P D, Ross R P, Hill C: Bacteriocin production: a probiotic trait?*Applied and environmental microbiology* 2012, 78(1):1-6.
5. Arthur T D, Cavera V L, Chikindas M L: On bacteriocin delivery systems and potential applications. *Future Microbiol* 2014, 9(2):235-248.
6. Jack R W, Tagg J R, Ray B: Bacteriocins of gram-positive bacteria. *Microbiol Rev* 1995, 59(2):171-200.
7. Hammami R, Fernandez B, Lacroix C, Fliss 1: Anti-infective properties of bacterocins: an update. *Cellular and molecular life sciences: CMLS* 2013, 70(16):2947-2967.
8. Zheng J, Ganzle M G, Lin X B, Ruan L, Sun M: Diversity and dynamics of bacterocins from human microbiome. *Environmental microbiology* 2015, 17(6):2133-2143.
9. Kommineni S, Bretl D J, Lam V, Chakraborty R, Hayward M, Simpson P, Cao Y, Bousounis P, Kristich C J, Salzman N H: Bacteriocin production augments niche competition by enterococci in the mammalian gastrointestinal tract. *Nature* 2015, 526(7575):719-722.
10. McBride S M, Fischetti V A, Leblanc D J, Moellering R C, Jr., Gilmore M S: Genetic diversity among *Enterococcus faecalis. PloS one* 2007, 2(7):e582.
11. Benyacoub J, Czarnecki-Maulden G L, Cavadini C, Sauthier T, Anderson R E, Schiffrin E J, von der Weid T: Supplementation of food with *Enterococcus faecium* (SF68) stimulates immune functions in young dogs. *J Nutr* 2003, 133(4):1158-1162.
12. Pieniz S, Andreazza R, Anghinoni T, Camargo F, Brandelli A: Probiotic potential, antimicrobial and antioxidant activities of *Enterococcus durans* strain LAB18s. *Food Control* 2014, 37:251-256.
13. Richards M I, Edwards J R, Culver D H, Gaynes R P: Nosocomial infections in combined medical-surgical intensive care units in the United States. *Infect Control Hosp Epidemiol* 2000, 21(8):510-515.
14. Fisher K, Phillips C: The ecology, epidemiology and virulence of *Enterococcus. Microbiology* 2009, 155(Pt 6):1749-1757.
15. Shepard B D, Gilmore M S: Antibiotic-resistant enterococci: the mechanisms and dynamics of drug introduction and resistance. *Microbes and Infection/Institut Pasteur* 2002, 4(2):215-224.
16. Broaders E, Gahan C G, Marchesi J R: Mobile genetic elements of the human gastrointestinal tract: potential for spread of antibiotic resistance genes. *Gut microbes* 2013, 4(4):271-280.
17. Hegstad K, Mikalsen T, Coque T M, Werner G, Sundsfjord A: Mobile genetic elements and their contribution to the emergence of antimicrobial resistant *Enterococcus faecalis* and *Enterococcus faecium. Clinical microbiology and infection: the official publication of the European Society of Clinical Microbiology and Infectious Diseases* 2010, 16(6):541-554.
18. Kommineni S, Kristich C I, Salzman N H: Harnessing bacterlocin biology as targeted therapy in the GI tract. *Gut microbes* 2016:0.
19. Paulsen I T, Banerjei L, Myers G S, Nelson K E, Seshadri R, Read T D, Fouts D E, Eisen J A, Gill S R, Heidelberg J F et al: Role of mobile DNA in the evolution of vancomycin-resistant *Enterococcus faecalis. Science* 2003, 299(5615):2071-2074.
20. Vesic D, Kristich C J: A Rex family transcriptional repressor influences H2O2 accumulation by *Enterococcus faecalis. Journal of bacteriology* 2013, 195(8):1815-1824.
21. Kristich Cj, Djoric D, Little J L: Genetic basis for vancomycin-enhanced cephalosporin susceptibility in vancomycin-resistant enterococci revealed using counter-selection with dominant-negative thymidylate synthase. *Antimicrobial agents and chemotherapy* 2014, 58(3): 1556-1564.
22. Gibson D G, Young L, Chuang R Y, Venter J C, Hutchison C A, Smith H O: Enzymatic assembly of DNA molecules up to several hundred kilobases. *Nat Methods* 2009, 6(5):343-U341.
23. Maricic N, Dawid S: Using the overlay assay to qualitatively measure bacterial production of and sensitivity to pneumococcal bacteriocins. *J Vis Exp* 2014(91):e51876.
24. Guiton P S, Hung C S, Kline K A, Roth R, Kau A L, Hayes E, Heuser J, Dodson K W, Caparon M G, Hultgren S J: Contribution of autolysin and Sortase a during *Enterococcus faecalis* DNA-dependent biofllm development. *Infection and immunity* 2009, 77(9):3626-3638.
25. Kemp K D, Singh K V, Nallapareddy S R, Murray B E: Relative contributions of *Enterococcus faecalis* OG1R F sortase-encoding genes, srtA and bps (srtC), to biofllm formation and a murine model of urinary tract infection. *Infection and immunity* 2007, 75(11):5399-5404.
26. Kristich C j, Wells C L, Dunny G M: A eukaryotic-type Ser/Thr kinase in *Enterococcus faecalis* mediates antimicrobial resistance and intestinal persistence. *Proc Natl Acad Sci USA* 2007, 104(9):3508-3513.
27. Lindenstrauss A G, Ehrmann M A, Behr J, Landstorfer R, Haller D, Sartor R B, Vogel R F: Transcriptome analysis of *Enterococcus faecalis* toward its adaption to surviving in the mouse intestinal tract. *Archives of microbiology* 2014, 196(6):423-433.
28. Kristich C J, Manias D A. Dunny G M: Development of a method for markerless genetic exchange in *Enterococcus faecalis* and its use in construction of a srtA mutant. *Applied and environmental microbiology* 2005, 71(10): 5837-5849.

We claim:

1. A modified *Enterococcal* strain, wherein the strain comprises:

a. a ΔsrtA mutation, b. a first plasmid encoding Bac 21, wherein the plasmid has a ΔbacAB mutation, and c. a second plasmid encoding a proximal part of bac-21 operon.

2. The modified strain on claim 1, wherein the strain is either *Enterococcus faecalis* or *Enterococcus faecium.*

3. The modified strain of claim 1, wherein the proximal segment is bacABCDE.

4. The modified strain of claim 1, wherein the strain is inefficient at establishing long-term colonization of the GI tract compared to its respective isogenic wild-type, but remains capable of delivering bacteriocin efficiently to decolonize antibiotic-resistant enterococci to the levels below the limit of detection (100 CFU $ml^{-1}$).

5. The modified strain of claim 1, wherein the strain comprises ΔsrtA mutation of SEQ ID NO:9.

6. The modified strain of claim 1, wherein the first plasmid comprises SEQ ID NO:1.

7. The modified strain of claim 1, wherein the second plasmid is SEQ ID NO:4.

8. A composition comprising the modified strain of claim 1 and a pharmaceutically acceptable carrier.

9. An animal feed composition comprising the modified strain of claim 1 and at least one animal feed product.

10. A method of creating a modified *Enterococcal* strain, comprising the steps of:

a. obtaining an *Enterococcal* strain with a ΔsrtA mutation, and b. introducing a first and a second plasmid into the strain, wherein the first plasmid encodes Bac21, wherein the first plasmid is a ΔbacAB mutant, and wherein the second plasmid encodes a segment proximal to the bacA promoter.

11. The method of claim 10, wherein the *Enterococcal* strain is either *Enterococcus faecalis* or *Enterococcus faecium.*

12. The method of claim 10, wherein the ΔsrtA mutation is r deletion of SEQ ID NO:8 from the open reading frame of srtA.

13. The method of claim 10, wherein the first plasmid comprises SEQ ID NO:1.

14. The method of claim 10, wherein the second plasmid comprises SEQ ID NO:4.

15. A modified enterococcal strain made by the method of claim 10.

16. A method of treating enterococci infections in a human patient in need thereof, the method comprising:

administering to the patient a therapeutically effective amount of the modified enterococcal strain of claim 1.

17. A method of inhibiting the GI colonization by antibiotic-resistant enterococci in human patient in need thereof or altering the microbial composition of the GI track of a human patient, the method comprising: administering to the patient a therapeutically effective amount of the modified enterococcal strain of claim 1.

18. A method of preventing GI track colonization of antibiotic resistant enterococci in a human patient, the method comprising administering to the patient a therapeutically effective amount of the modified enterococcal strain of claim 1.

19. The method of claim 16, the method first comprising detecting antibiotic resistant enterococcal bacteria in the GI track of the human patient.

20. A method of treating enterococci infections in a non-human animal, the method comprising administering to the non-human animal a therapeutically effective amount of the modified enterococcal strain of claim 1.

21. A method of preventing GI track colonization of antibiotic resistant enterococci in a non-human animal, the method comprising: administering to the non-human animal a therapeutically effective amount of the modified enterococcal strain of claim 1.

22. The method of claim 21, wherein the non-human animal is a poultry.

23. A method of reducing contamination of livestock food products with antibiotic-resistant enterococci, the method comprising administering to the livestock before slaughter an effective amount of the modified enterococcal strain of claim 1 in an amount effective to reduce the amount of antibiotic-resistant enterococci in the GI track of the livestock.

24. The method of claim 23, herein the livestock is a poultry.

25. The method of claim 16, wherein the modified enterococcal strain is administered orally.

26. The method of claim 20, wherein the modified enterococcal strain is administered in the animal food or water.

27. The method of claim 21, wherein the modified enterococcal strain is administered orally.

28. The method of claim 22, wherein is a chicken, turkey, quail or duck.

29. The method of claim 21, wherein the non-human animal is a livestock animal.

30. The method of claim 21, wherein the non-human animal is a domestic animal.

31. The method of claim 30, wherein the domestic animal is a cat, dog, pig, or bird.

32. The method of claim 24, wherein the poultry is a chicken.

33. The method of claim 23, wherein the modified enterococcal strain is administered orally.

* * * * *

UNITED STATES PATENT AND TRADEMARK OFFICE

CERTIFICATE OF CORRECTION

PATENT NO. : 10,920,290 B2
APPLICATION NO. : 16/485736
DATED : February 16, 2021
INVENTOR(S) : Nita Salzman et al.

It is certified that error appears in the above-identified patent and that said Letters Patent is hereby corrected as shown below:

In the Specification

Column 18, Line 13, “bacterlocin” should be --bacteriocin--.

Column 18, Line 40, “biofllm” should be --biofilm--.

Column 18, Line 44, “biofllm” should be --biofilm--.

In the Claims

Column 102, Line 58, Claim 12, “is r deletion” should be --is a deletion--.

Column 104, Line 8, Claim 24, “herein” should be --wherein--.

Column 104, Line 16, Claim 28, “wherein is” should be --wherein the poultry is--.

Signed and Sealed this
First Day of June, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 10

<210> SEQ ID NO 1
```

<211> LENGTH: 2817
<212> TYPE: DNA
<213> ORGANISM: Artificial Sequence
<220> FEATURE:
<223> OTHER INFORMATION: synthetic

<400> SEQUENCE: 1
ttccagagaa tcggatggta ttaattttaa agaacaatca gtattctgaa aaacaaataa 60
atgttctcga tcagttacaa aagttagatt ttaagattga ggaattagaa agtaccttac 120
agatagaaga tgagaggttc aatctggaag aatatcaaga agccatgatt gatgaaaatt 180
atctttatga tatagatatc gtagaagaaa acaaagaagt agttcaagcg tataaccagg 240
atagaatgaa agataagtca aatgaaaatg aacaatttga aggaattagt catgatattg 300
attgctaaga agtatctagt gacttttttc ttgattgaaa ctcaagatag atatgttatt 360
gcttgcatca aaataaacta catgggtata atagcaatga aatgcatttc cggacagatc 420
tcgacccgtg ctataattat actaatttta taaggaggaa aaaatatggg cattttttagt 480 atttttgtaa tcagcacagt tcattatcaa ccaaacaaaa aataagtggt tataatgaat 540
cgttaataag caaaattcat ataaccaaat taaagagggt tataatgaac gagaaaaata 600
taaaacacag tcaaaacttt attacttcaa aacataatat agataaaata atgacaaata 660
taagattaaa tgaacatgat aatatctttg aaatcggctc aggaaaaggc cattttaccc 720
ttgaattagt aaagaggtgt aatttcgtaa ctgccattga aatagaccat aaattatgca 780
aaactacaga aaataaactt gttgatcacg ataatttcca agttttaaac aaggatatat 840
tgcagtttaa atttcctaaa aaccaatcct ataaaatata tggtaatata ccttataaca 900
taagtacgga tataatacgc aaaattgttt ttgatagtat agctaatgag atttatttaa 960
tcgtggaata cgggtttgct aaaagattat taaatacaaa acgctcattg gcattacttt 1020
taatggcaga agttgatatt tctatattaa gtatggttcc aagagaatat tttcatccta 1080
aacctaaagt gaatagctca cttatcagat taagtagaaa aaaatcaaga atatcacaca 1140
aagataaaca aaagtataat tatttcgtta tgaaatgggt taacaaagaa tacaagaaaa 1200
tatttacaaa aaatcaattt aacaattcct taaaacatgc aggaattgac gatttaaaca 1260
atattagctt tgaacaattc ttatctcttt tcaatagcta taaattattt aataagtaat 1320
gttgtacatg cgattagata tcattaattt tgagaaatat ttgaaaattt ccttctatat 1380
atcaatattt atttttttc tgggagtgtt agcagggatt ataataggtc ctcatataaa 1440
taaattggac tattttggtc aggaagtttc attttatagt gttagtgtta ataatttaaa 1500
ggtctctttt tatttcctca ctataggaat ggtaacaggg gggatttatg catttttatt 1560
tatgggtata aatggttata taattggtaa gttgattcaa tatttataca ttaacaatga 1620
actaaatgtt ttgtataaag gtcttcttcc acattttttt atagagcttt taggattggc 1680
aacatttagt atgataagta ccattccaat atttgttatt ttggtttttt ttaaaacgcc 1740
tacacatgta gttcctatta aaaaaatcat aaagttaagt gtgtttttta ctgtacttgg 1800
aatagtttta ataataattg gaggatatat agaatctaat ataagctatg tagatatacg 1860
atagaagttg agatagaaaa ctaatctcaa aggaagatat ccgcctattt ccaaacgtta 1920
tacgaaagaa tttaaacaaa ccattgatca cgaatcaaaa atgctgaatt aaagatatac 1980
tcattaaagg aagagtgggc actattttaa atttatacaa ccaaggtaaa aattttcgtg 2040
aattatcttt ataataatat gtcggttact taaaattttt gaaattcaca ataaacatat 2100
aattaacagt gtgataattt atttgtctac aagtcaattg ggataggcaa ctctagttgc 2160
ataaaatatc tctcacaaaa agtgtttcat gtattactga atctgatcca tataagttct 2220
taagaaagga agataagttt gtacaagttt actttgaaaa aatacatcgg tattacttca 2280
ctattttttt tgttttcaaa tattctaatt gctgaagagt ttatttttgt agaaaaaaac 2340
ttgagttttt tccctaaatt agggataatt gtgcttgttt tttttatgag tgctcccgct 2400
tttgttgttg ttactttaat tttgacttgt ttagttgcat ttcttattag tttaattaac 2460
aaattttaca gtttcaaaag agtatactta tcgactttat ttgtaaatag tattcagtta 2520
ttcgtaaatt tagctttatt tagtgtattt ttacattaca atttaaattt gcgattgcta 2580
agtataatga gttttatgat taatattttt ttagtagtta tctatcgcaa tttattaatt 2640
aaatttgcga atgtaaacag tagggctgcg aatgtattat caattttcgg gattgcttta 2700
tctgtaattt atttggtggt aggagtaaag taatgaaaaa aataacaatt aacaacttga 2760
gtttttatta tgaatccaaa gatattatgg tgtttgacag gttatcttta gaatttt 2817

<210> SEQ ID NO 2
<211> LENGTH: 909
<212> TYPE: DNA
<213> ORGANISM: Artificial Sequence
<220> FEATURE:
<223> OTHER INFORMATION: synthetic - ermC gene insert

<400> SEQUENCE: 2
cggacagatc tcgacccgtg ctataattat actaatttta taaggaggaa aaaatatggg 60
catttttagt atttttgtaa tcagcacagt tcattatcaa ccaaacaaaa aataagtggt 120
tataatgaat cgttaataag caaaattcat ataaccaaat taaagagggt tataatgaac 180
gagaaaaata taaaacacag tcaaaacttt attacttcaa aacataatat agataaaata 240
atgacaaata taagattaaa tgaacatgat aatatctttg aaatcggctc aggaaaaggc 300
cattttaccc ttgaattagt aaagaggtgt aatttcgtaa ctgccattga aatagaccat 360
aaattatgca aaactacaga aaataaactt gttgatcacg ataatttcca agttttaaac 420
aaggatatat tgcagtttaa atttcctaaa aaccaatcct ataaaatata tggtaatata 480
ccttataaca taagtacgga tataatacgc aaaattgttt ttgatagtat agctaatgag 540
atttatttaa tcgtggaata cgggtttgct aaaagattat taaatacaaa acgctcattg 600
gcattacttt taatggcaga agttgatatt tctatattaa gtatggttcc aagagaatat 660
tttcatccta aacctaaagt gaatagctca cttatcagat taagtagaaa aaaatcaaga 720
atatcacaca aagataaaca aaagtataat tatttcgtta tgaaatgggt taacaaagaa 780
tacaagaaaa tatttacaaa aaatcaattt aacaattcct taaaacatgc aggaattgac 840
gatttaaaca atattagctt tgaacaattc ttatctcttt tcaatagcta taaattattt 900
aataagtaa 909

<210> SEQ ID NO 3
<211> LENGTH: 1908
<212> TYPE: DNA
<213> ORGANISM: Artificial Sequence
<220> FEATURE:
<223> OTHER INFORMATION: synthetic - PD1 backbone

<400> SEQUENCE: 3
ttccagagaa tcggatggta ttaattttaa agaacaatca gtattctgaa aaacaaataa 60
atgttctcga tcagttacaa aagttagatt ttaagattga ggaattagaa agtaccttac 120

```
agatagaaga tgagaggttc aatctggaag aatatcaaga agccatgatt gatgaaaatt    180

atctttatga tatagatatc gtagaagaaa acaaagaagt agttcaagcg tataaccagg    240

atagaatgaa agataagtca aatgaaaatg aacaatttga aggaattagt catgatattg    300

attgctaaga agtatctagt gacttttttc ttgattgaaa ctcaagatag atatgttatt    360

gcttgcatca aaataaacta catgggtata atagcaatga aatgcatttc tgttgtacat    420

gcgattagat atcattaatt ttgagaaata tttgaaaatt tccttctata tatcaatatt    480

tatttttttt ctgggagtgt tagcagggat tataataggt cctcatataa ataaattgga    540

ctattttggt caggaagttt cattttatag tgttagtgtt aataatttaa aggtctcttt    600

ttatttcctc actataggaa tggtaacagg ggggatttat gcatttttat ttatgggtat    660

aaatggttat ataattggta agttgattca atatttatac attaacaatg aactaaatgt    720

tttgtataaa ggtcttcttc cacatttttt tatagagctt ttaggattgg caacatttag    780

tatgataagt accattccaa tatttgttat tttggttttt tttaaaacgc ctacacatgt    840

agttcctatt aaaaaaatca taaagttaag tgtgtttttt actgtacttg gaatagtttt    900

aataataatt ggaggatata tagaatctaa tataagctat gtagatatac gatagaagtt    960

gagatagaaa actaatctca aaggaagata tccgcctatt tccaaacgtt atacgaaaga   1020

atttaaacaa accattgatc acgaatcaaa aatgctgaat taaagatata ctcattaaag   1080

gaagagtggg cactatttta aatttataca accaaggtaa aaattttcgt gaattatctt   1140

tataataata tgtcggttac ttaaaatttt tgaaattcac aataaacata taattaacag   1200

tgtgataatt tatttgtcta caagtcaatt gggataggca actctagttg cataaaatat   1260

ctctcacaaa aagtgtttca tgtattactg aatctgatcc atataagttc ttaagaaagg   1320

aagataagtt tgtacaagtt tactttgaaa aaatacatcg gtattacttc actatttttt   1380

ttgttttcaa atattctaat tgctgaagag tttatttttg tagaaaaaaa cttgagtttt   1440

ttccctaaat tagggataat tgtgcttgtt ttttttatga gtgctcccgc ttttgttgtt   1500

gttactttaa ttttgacttg tttagttgca tttcttatta gtttaattaa caaattttac   1560

agtttcaaaa gagtatactt atcgacttta tttgtaaata gtattcagtt attcgtaaat   1620

ttagctttat ttagtgtatt tttacattac aatttaaatt tgcgattgct aagtataatg   1680

agttttatga ttaatatttt tttagtagtt atctatcgca atttattaat taaatttgcg   1740

aatgtaaaca gtagggctgc gaatgtatta tcaattttcg ggattgcttt atctgtaatt   1800

tatttggtgg taggagtaaa gtaatgaaaa aaataacaat taacaacttg agtttttatt   1860

atgaatccaa agatattatg gtgtttgaca ggttatcttt agaatttt                1908
```

<210> SEQ ID NO 4
<211> LENGTH: 15314
<212> TYPE: DNA
<213> ORGANISM: Artificial Sequence
<220> FEATURE:
<223> OTHER INFORMATION: synthetic

<400> SEQUENCE: 4

```
agtttctttt tccgtgtgaa tatcaaaatc aataaagaag gtattgattt gtcttaaatt     60

gttttcagaa tgtcctttag tgtatgaacg gttttcgtct gcatacgtac cataacgata    120

aacgtttggt gtccaatgcg taaatgtatc ttgattttcg tgaatcgctt cttcggaagt    180

cagaacaacg ccacgtccgc caatcatgct ttttttgag cgatacgcaa aaatagcccc    240

tttactttta ctggcttggt agtgattgag cgaattttac tatttttaaa tttgtacttt    300
```

```
aacaagccgt catgaagcac agtttctaca acaaaaggga tattcattca gctgttctcc    360
tttcttacga aaattaatta gttagaagct acgatcaaag ttgaatcaca acaaaaaagg    420
caatcaacta agtttttctt aattgattgc ctggtatctt cttaaagact tgaaatcccc    480
tcaaaaaccc gatataatgg gtttacagat atttaagtat ctgattaata aagtaattaa    540
atactttacc aaattttggg tctcgacttc tttaattgat tggtggtaat caattaaggc    600
tcgcagttaa aatttctcag gctttaactg gtcgtggctc ttttttgta ttctttattc     660
agttcgttgt ttcgttatat ctagtatatc gctttttaaa aaaataagca atgatttcgt    720
gcattattca cacgaaatca ttgctttttt cttcttccat ttctaactcc aatgttactt    780
gttctgtttc tggttctggt tctgttggct catttgggat taaatccact actagcgttg    840
agttagttcc gtctctaata gccggttaag taatagccgg ttaagtggtc aaactttggg    900
aaaatctcaa cccgcattaa gttttgatgc catgacaatc gttggaaatt tgaacaaaac    960
taatgctaaa aagctatctg actttatgag tgtagagcca caaatacgac tttgggatat   1020
acttcaaaca aagtttaaag ctaaggcact tcaagaaaaa gtttatatcg aatatgacaa   1080
agtaaaagca gatacttggg atagacgtaa tatgcgtgtt gaatttaatc ccaataaact   1140
cacacatgaa gaaatgattt ggttaaaaca aaatattatc gactacatgg aagatgacgg   1200
ttttacaaga ttagacttag cttttgattt tgaagatgat ttgagcgatt actatgcaat   1260
gactgataaa gcagttaaga aaactgtttt ttatggtcgt aatggcaagc cagaaacaaa   1320
atattttggt gtccgtgata gtgatagatt tattagaatt tataataaaa aacaagaacg   1380
taaagataac gcagatgttg aagttgtgtt tgaacattta tggcgtgtag aagttgaatt   1440
aaaaagagat atggttgatt actggaatga ttgttttaat gatttacaca tctttgaaac   1500
ctgcgtgggc tactttagaa aaaattaatg agcaagctat ggtttatact ttgttgcatg   1560
aagaaagtat gtggggaaag ctaagtaaga atactaagac taaatttaaa aaattgatta   1620
gagaaatatc tccaattgat ttaacggaat taatgaaatc gactttaaaa gcgaacgaaa   1680
aacaattgca aaagcagatt gatttttggc aacgtgaatt taggttttgg aagtaaaata   1740
agttttattt gataaaaatt gctaattcag tataattaat atttacgagg tgacataacg   1800
tatgaaaaaa tcagaggatt attcctccta aatataaaaa tttaaaattt aggaggaagt   1860
tatatatgac ttttaatatt attgaattag aaaattggga tagaaaagaa tattttgaac   1920
actattttaa tcagcaaact acttatagca ttactaaaga aattgatatt actttgttta   1980
aagatatgat aaaaaagaaa ggatatgaaa tttatccctc tttaatttat gcaattatgg   2040
aagttgtaaa taaaaataaa gtgtttagaa caggaattaa tagtgagaat aaattaggtt   2100
attgggataa gttaaatcct ttgtatacag tttttaataa gcaaactgaa aaatttacta   2160
acatttggac tgaatctgat aaaaacttca tttcttttta taataattat aaaaatgact   2220
tgcttgaata taaagataaa gaagaaatgt ttcctaaaaa accgatacct gaaaacacca   2280
taccgatttc aatgattcct tggattgatt ttagttcatt taatttaaat attggtaaca   2340
atagcagctt tttattgcct attattacga taggtaaatt ttatagtgag aataataaaa   2400
tttatatacc agttgctctg caacttcatc attctgtatg tgatggttac catgcttcac   2460
tatttatgaa tgaatttcaa gatataattc atagggtaga tgattggatt tagtttttag   2520
attttgaaag tgaatttaat tttatacacg taagtgatca taaaatttat gaacgtataa   2580
caaccacatt ttttggttgc ttgtggtttt gattttgaat ttggttttga acttatggac   2640
```

-continued

```
tgatttattc agtccatttt ttgtgcttgc acaaaaacta gcctcgcaga gcacacgcat   2700
taatgactta tgaaacgtag taaataagtc tagtgtgtta tactttactt ggaagatgca   2760
ccgaataaaa aatattgaag aacaactagc aaaagatttt aaagagttat tttattttaa   2820
gtctttataa catgagtgaa gcgaattttt aaatttcgat agaaattttt acatcaaaaa   2880
gccccctgtc aaaattgacg aagggggttt tttggcgcac gcttttcgtt agaaatatac   2940
aagattgaaa atcgtgtata agtgcgccct ttgttttgaa cttagcacgt tacatcaatt   3000
ttttaaaatg atgtataagt gcgccctttt aaattttgag tgattatatt ttttgagtta   3060
gaaaaaggga ttgggaaaat ttcccaaaat aatttaaaaa ataagcaaaa attttcgata   3120
gagaatgtgc tatttttgt caaaggtgta taccttgact gtgcttgctg ttacattaag   3180
tttattttta agttattaaa aaagaaatag cttttaaagt ttggctcgct gtcgctttat   3240
aaagctgatt gacttttgat tgcaaactac ttaaagaaaa caaactcgga ctattcgttt   3300
tcttctcttt ggtttgaaca tcagcaatta tcccctcttg attgcctatt ttagcttgtt   3360
tagaagaaac aaaagctaaa agctcctctt gggttttaaa acgctgtgtg gggcttagaa   3420
cgcccttaaa cgacccttgg tttactttta tactagcttc cacctcgaaa aaaggttctt   3480
ttttaaaatt ctctatggct tcctggcgct gaaaaaataa ggtataaggt gggcgtttga   3540
acacgtccta gtgaaaatgt accttgtacg ccccttctgt tgtaaattta acgtatacaa   3600
agggcttgcg ttcatgccga tcaaccaatc ggcaatttgg cgtgtttgcg cttcttgata   3660
aaagggatag taattcattc caggttgcaa attttgaaaa ccgcttcgga ttacatcttt   3720
ttctaagcta ttgatccata gtcttttaaa tgttttatct tttgaaaagg catttgcttt   3780
atggataatc gaccaggcga tattttcacc ttctctgtcg ctatctgttg caacaataat   3840
tgtatttgcc tttttgagaa gttctgcaac aattttaaac tgctttccct tatcttttgc   3900
aacttcaaaa tcgtatcgat caggaaaaat cggcaaagat tcaagtttcc aattttgcca   3960
cttttcgtca taatgacctg gttctgctaa ttccactaaa tgcccaaaac caaaggtgat   4020
aaacgtttca tctgtaaata gtgggtcttt gatctcaaaa taaccgtctt ttttggtgct   4080
ttgttttaaa gcacttgcgt aggctaatgc ctggcttggt tttcagcta aaataaccgt   4140
actcattaac tatccctctt ttcattgttt tttctttgat cgactgtcac gttatatctt   4200
gctcgatacc ttctaaacgt tcggcgattg attccagttt gttcttcaac ttctttatcg   4260
gataaaccat tcaaaaacaa atcgaaagcc gagatgcgcc gcgtgcggct gctggagatg   4320
gcggacgcga tggatatgtt ctgccaaggg ttggtttgcg cattcacagt tctccgcaag   4380
aattgattgg ctccaattct tggagtggtg aatccgttag cgaggtgccg ccggcttcca   4440
ttcaggtcga ggtggcccgg ctccatgcac cgcgacgcaa cgcggggagg cagacaaggt   4500
atagggcggc gcctacaatc catgccaacc cgttccatgt gctcgccgag gcggcataaa   4560
tcgccgtgac gatcagcggt ccagtgatcg aagttaggct ggtaagagcc gcgagcgatc   4620
cttgaagctg tccctgatgg tcgtcatcta cctgcctgga cagcatggcc tgcaacgcgg   4680
gcatcccgat gccgccggaa gcgagaagaa tcataatggg gaaggccatc cagcctcgcg   4740
tcgcgaacgc cagcaagacg tagcccagcg cgtcggccgc catgccggcg ataatggcct   4800
gcttctcgcc gaaacgtttg gtggcgggac cagtgacgaa ggcttgagcg agggcgtgca   4860
agattccgaa taccgcaagc gacaggccga tcatcgtcgc gctccagcga aagcggtcct   4920
cgccgaaaat gacccagagc gctgccggca cctgtcctac gagttgcatg ataaagaaga   4980
cagtcataag tgcggcgacg atagtcatgc cccgcgccca ccggaaggag ctgactgggt   5040
```

```
tgaaggctct caagggcatc ggtcgacgct ctcccttatg cgactcctgc attaggaagc   5100
agcccagtag taggttgagg ccgttgagca ccgccgccgc aaggaatggt gcatgcaagg   5160
agatggcgcc caacagtccc ccggccacgg ggcctgccac catacccacg ccgaaacaag   5220
cgctcatgag cccgaagtgg cgagcccgat cttccccatc ggtgatgtcg gcgatatagg   5280
cgccagcaac cgcacctgtg gcgccggtga tgccggccac gatgcgtccg gcgtagagtt   5340
ccagagaatc ggatggtatt aattttaaag aacaatcagt attctgaaaa acaaataaat   5400
gttctcgatc agttacaaaa gttagatttt aagattgagg aattagaaag taccttacag   5460
atagaagatg agaggttcaa tctggaagaa tatcaagaag ccatgattga tgaaaattat   5520
ctttatgata tagatatcgt agagaaaaca aagaagtagt tcaagcgtat aaccaggata   5580
gaatgaaaga taagtcaaat gaaaatgaac aatttgaagg aattagtcat gatattgatt   5640
gctaagaagt atctagtgac tttttttcttg attgaaactc aagatagata tgttattgct   5700
tgcatcaaaa taaactacat gggtataata gcaatgaaat gcatttcaaa aatattttga   5760
ggaggagtat catggttaaa gaaaataaat tttctaagat ttttatttta atggctttga   5820
gtttttgggg gttagccttg tttagtgcaa gtcttcagtt tttgccgatt gcacatatgg   5880
ctaaagagtt cggtatacca gcagcagttg caggaactgt acttaatgta gttgaagctg   5940
gtggatgggt cactactatt gtatcaaatc ttactgctgt aggtagcgga ggtctttcct   6000
tactcgctgc agcaggaaga gagtcaatta aagcatacct taagaaagaa attaagaaaa   6060
aaggaaaaag agcagttatt gcttggtaat ttaacaatat gataaaaaaa caggatattt   6120
tctagagata ttctgttttt taattaaaaa aagggggggcg ctcatgaatc tctttggaat   6180
tctaatgaag ttaagaataa atcaagagag tagtttggtt aaaagagtac tttcctactt   6240
taacttaaaa ctatcgttaa agctctattt atttattaat atattctttg aattttcatt   6300
ggcatttgtt gttagtttgg gattaagact aactttaata aaatcagata taaatgtaaa   6360
tttatttttt ataatatttt ttattttagg aattgttcaa ggagcatcaa attgttatag   6420
aacgcacgtc tttccttttg aagaattaag gaaattagca acaatatctt ctagaaagat   6480
aagctttatt atgattgtta cagacttatt ctatattttt atgttttcat cttcaatact   6540
atatggatta ttgagtttaa tatatataag tagtaatgct tttatttttc aaaaaattag   6600
tctatctgta tttttttat ttatatacat ttgttcattt tattgtagta ataggatttt   6660
tggacagtat atctataata aaatagttaa ggctattgga ttaacacgat taatccttta   6720
tagcattgga gccgctttat ttacttattt tggtttttt atagtatcat tcgtatttag   6780
taacatagta tattttataa aaaaatattt tgttaacata gaaagtgtaa ataataaagt   6840
aatatgggag tcgttttcta aggatatagg aatgttttat gtaaatagcg ccagtaaatt   6900
ttatgagagt catgtatatt catttactta tatagatgtt tttttagtat cggctatgtt   6960
attaatttg gcaatattac tattagctat ggaaccaaaa ctctaccctt taaaaacaaa   7020
aatgctgcca aaaactaaaa tagacttatg caatttatat gtattttttt tgaataaagc   7080
attaaaaaaa aatatttttt ttaaatgcag cttgttaaag ttagctaata caagatggat   7140
tattgctaat aatttctttc aaaatataat tttgacatat gaatcattct tttacattgg   7200
agtaatgctt tcaataatac tattgaattc acaaaataga atgttgcaaa tacaactatt   7260
atttctttta aatatacttg taattggaaa tcagacattt gaaataagag aagaaatgta   7320
cccttatcta tcttttggat cagaaaggaa tcaatttacg cttctaagat cgtctccgaa   7380
```

-continued

```
tggtttgaat aaagttttta attcgaaact aacgatatac aggttatttt tattaattcc   7440
tttacttata ttaattatca taaatattgt agtttctgta tacattatga ttccggtaat   7500
ttttgctatc tttttgttta taacattttc tatgtctgtg tatgttttcc ctatgattca   7560
aatgtatatg attcctttag ctactaaact agattacact aatgatacag aaattggaag   7620
tgctaaagat gaaaaaattg ttttagagaa atttcaaaca gttccaagat actttttttaa   7680
tatcgttcct ttagtgctta catttatctt tccaattgta ggggaaagtt attcattaat   7740
aatatttttc ggagagttag tatatttctc tttagcaaca ataatatttg tgtttttcag   7800
taaaaaaatt attaggaaag gaatttttgt tgtacatgcg attagatatc attaattttg   7860
agaaatattt gaaaatttcc ttctatatat caatatttat ttttttctg ggagtgttag   7920
cagggattat aataggtcct catataaata aattggacta ttttggtcag gaagtttcat   7980
tttatagtgt tagtgttaat aatttaaagg tctcttttta tttcctcact ataggaatgg   8040
taacaggggg gatttatgca tttttattta tgggtataaa tggttatata attggtaagt   8100
tgattcaata tttatacatt aacaatgaac taaatgtttt gtataaaggt cttcttccac   8160
atttttttat agagctttta ggattggcaa catttagtat gataagtacc attccaatat   8220
ttgttatttt ggtttttttt aaaacgccta cacatgtagt tcctattaaa aaaatcataa   8280
agttaagtgt gtttttttact gtacttggaa tagttttaat aataattgga ggatatatag   8340
aatctaatat aagctatgta gatatacgat agaagttgag atagaaaact aatctcaaag   8400
gaagatatcc gcctatttcc aaacgttata cgaaagaatt taaacaaacc attgatcacg   8460
aatcaaaaat gctgaattaa agatatactc attaaaggaa gagtgggcac tattttaaat   8520
ttatacaacc aaggtaaaaa ttttcgtgaa ttatctttat aataatatgt cggttactta   8580
aaatttttga aattcacaat aaacatataa ttaacagtgt gataatttat ttgtctacaa   8640
gtcaattggg ataggcaact ctagttgcat aaaatatctc tcacaaaaag tgtttcatgt   8700
attactgaat ctgatccata taagttctta agaaaggaag ataagtttgt acaagtttac   8760
tttgaaaaaa tacatcggta ttacttcact attttttttg ttttcaaata ttctaattgc   8820
tgaagagttt atttttgtag aaaaaaactt gagtttttttc cctaaattag ggataattgt   8880
gcttgttttt tttatgagtg ctcccgcttt tgttgttgtt actttaattt tgacttgttt   8940
agttgcattt cttattagtt taattaacaa attttacagt ttcaaaagag tatacttatc   9000
gactttattt gtaaatagta ttcagttatt cgtaaattta gctttattta gtgtattttt   9060
acattacaat ttaaatttgc gattgctaag tataatgagt tttatgatta atatttttttt   9120
agtagttatc tatcgcaatt tattaattaa atttgcgaat gtaaacagta gggctgcgaa   9180
tgtattatca attttcggga ttgctttatc tgtaatttat ttggtggtag gagtaaagta   9240
atgaaaaaaa taacaattaa caacttgagt ttttattatg aatccaaaga tattatggtg   9300
tttgacaggt tatctttaga attttcttct gaaaaaagtt atgcactagt tggttctaat   9360
ggtgtaggaa aaacaacatt gttaaatatt ttatcaggta tatatcaacc cacaggggga   9420
acaatagaat atgacagcac tttgtataca gaaaaagtaa ctaaagaaaa agtagctttt   9480
ataccatata aaactaagct atatccttat cttgatgttt ttgatcatat aaagctaata   9540
gcagaattat ggggaattaa aacagactat ttagaatata aaagaaaagt actagaatat   9600
tgtagccgtc taaacttgga ctattataat aagaaagtag agtcttactc tacaggtatg   9660
gagtataaac tatacatttc tttaatgttg gcaagagatg tttctcttgt attattagat   9720
gaacctttta caatgttaga taaaaaaagt cgatatttag ctatggactt aatcaaagag   9780
```

```
aaaaaaataa taacaatatt ttcttcacat cagaaagata ttgtagaata tttgtcaaat   9840
gatattatta atcttgacaa actgaaggga gtaaacttgg aaaattatga aaagaattga   9900
ttacattatt attatagtct cactattagc aacaatagtc gcaatatttt taatagggat   9960
agattctatg ttaggcacag gacgggtgtg gtcgccatga tcgcgtagtc gatagtggct  10020
ccaagtagcg aagcgagcag gactgggcgg cggccaaagc ggtcggacag tgctccgaga  10080
acgggtgcgc atagaaattg catcaacgca tatagcgcta gcagcacgcc atagtgactg  10140
gcgatgctgt cggaatggac gatatcccgc aagaggcccg gcagtaccgg cataaccaag  10200
cctatgccta cagcatccag ggtgacggtg ccgaggatga cgatgagcgc attgttagat  10260
ttcatacacg gtgcctgact gcgttagcaa tttaactgtg ataaactacc gcattaaagc  10320
ttatcgatga taagctgtca aacatgagaa ttacaactta tatcgtatgg ggctgacttc  10380
aggtgctaca tttgaagaga taaattgcac tgaaatctag aaatatttta tctgattaat  10440
aagatgatct tcttgagatc gttttggtct gcgcgtaatc tcttgctctg aaaacgaaaa  10500
aaccgccttg cagggcggtt tttcgaaggt tctctgagct accaactctt tgaaccgagg  10560
taactggctt ggaggagcgc agtcaccaaa acttgtcctt tcagtttagc cttaaccggc  10620
gcatgacttc aagactaact cctctaaatc aattaccagt ggctgctgcc agtggtgctt  10680
ttgcatgtct ttccgggttg gactcaagac gatagttacc ggataaggcg cagcggtcgg  10740
actgaacggg gggttcgtgc atacagtcca gcttggagcg aactgcctac ccggaactga  10800
gtgtcaggcg tggaatgaga caaacgcggc cataacagcg gaatgacacc ggtaaaccga  10860
aaggcaggaa caggagagcg cacgagggag ccgccagggg gaaacgcctg gtatctttat  10920
agtcctgtcg ggtttcgcca ccactgattt gagcgtcaga tttcgtgatg cttgtcaggg  10980
gggcggagcc tatggaaaaa cggctttgcc gcggccctct cacttccctg ttaagtatct  11040
tcctggcatc ttccaggaaa tctccgcccc gttcgtaagc catttccgct cgccgcagtc  11100
gaacgaccga gcgtagcgag tcagtgagcg aggaagcgga atatatcctg tatcacatat  11160
tctgctgacg caccggtgca gccttttttc tcctgccaca tgaagcactt cactgacacc  11220
ctcatcagtg ccaacatagt aagccagtat acactccgct agcgctgatg tccggcggtg  11280
cttttgccgt tacgcaccac cccgtcagta gctgaacagg agggacagct gatagaaaca  11340
gaagccactg gagcacctca aaaacaccat catacactaa atcagtaagt tggcagcatc  11400
acccgacgca ctttgcgccg aataaatacc tgtgacggaa gatcacttcg cagaataaat  11460
aaatcctggt gtccctgttg ataccgggaa gccctgggcc aacttttggc gaaaatgaga  11520
cgttgatcgg cacgtaagag gttccaactt tcaccataat gaaataagat cactaccggg  11580
cgtatttttt gagttatcga gattttcagg agctaaggaa gctaaaatgg agaaaaaaat  11640
cactggatat accaccgttg atatatccca atggcatcgt aaagaacatt ttgaggcatt  11700
tcagtcagtt gctcaatgta cctataacca gaccgttcag ctggatatta cggccttttt  11760
aaagaccgta aagaaaaata agcacaagtt ttatccggcc tttattcaca ttcttgcccg  11820
cctgatgaat gctcatccgg aattccgtat ggcaatgaaa gacggtgagc tggtgatatg  11880
ggatagtgtt cacccttgtt acaccgtttt ccatgagcaa actgaaacgt tttcatcgct  11940
ctggagtgaa taccacgacg atttccggca gtttctacac atatattcgc aagatgtggc  12000
gtgttacggt gaaaacctgg cctatttccc taaagggttt attgagaata tgtttttcgt  12060
ctcagccaat ccctgggtga gtttcaccag ttttgattta aacgtggcca atatggacaa  12120
```

-continued

```
cttcttcgcc cccgttttca ccatgggcaa atattatacg caaggcgaca aggtgctgat  12180
gccgctggcg attcaggttc atcatgccgt ctgtgatggc ttccatgtcg gcagaatgct  12240
taatgaatta caacagtact gcgatgagtg gcagggcggg gcgtaatttt tttaaggcag  12300
ttattggtgc ccttaaacgc ctggtgctac gcctgaataa gtgataataa gcggatgaat  12360
ggcagaaatt cgaaagcaaa ttcgacccgg tcgtcggttc agggcagggt cgttaaatag  12420
ccgcttatgt ctattgctgg tttaccggtt tattgactac cggaagcagt gtgaccgtgt  12480
gcttctcaaa tgcctgaggc cagtttgctc aggctctccc cgtggaggta ataattgacg  12540
atatgatcat ttattctgcc tcccagagcc tgataaaaac ggttagcgct tcgttaatac  12600
agatgtaggt gttccacagg gtagccagca gcatcctgcg atgcagatcc ggaacataat  12660
ggtgcagggc gcttgtttcg gcgtgggtat ggtggcaggc cccgtggccg gggactgtt   12720
gggcgctgcc ggcacctgtc ctacgagttg catgataaag aagacagtca taagtgcggc  12780
gacgatagtc atgccccgcg cccaccggaa ggagctaccg gacagcggtg cggactgttg  12840
taactcagaa taagaaatga ggccgctcat ggcgttgact ctcagtcata gtatcgtggt  12900
atcaccggtt ggttccactc tctgttgcgg gcaacttcag cagcacgtag gggacttccg  12960
cgtttccaga ctttacgaaa cacggaaacc gaagaccatt catgttgttg ctcaggtcgc  13020
agacgttttg cagcagcagt cgcttcacgt tcgctcgcgt atcggtgatt cattctgcta  13080
accagtaagg caaccccgcc agcctagccg ggtcctcaac gacaggagca cgatcatgcg  13140
cacccgtggc caggacccaa cgctgcccga ctttaaacgt ggatcatttt ctttaaattt  13200
atgctgacga cctttgaatt tgcctttttt cttagcaatt tcgattcctt gtgcctgacg  13260
ttccttaatt ttttttcgtt ctgattctgc ttgatacttg tacaattcaa tgacaaggct  13320
attaatcaaa cgccttaaat tttcatcttc aataccattc attgagggta aatttaagac  13380
ttccagggtt gccccccttaa tttgaatttg attcatcaat tctgttaatt ctttattatt  13440
tcgtcctaat cgatctaatt cagtaacaat aacaatatcc ccttcacgaa tatagttaag  13500
catagcttgt aattgtgggc gttcgaccga ttgaccgctt aatttgtctg aaaagacctt  13560
agaaacgccc tgtaacgctt gtaattgccg atctaagttc tgttctttgc tactgacacg  13620
tgcataacca attttagcca ttttcaacca acctctaaaa ttctctcggt tgcaataacc  13680
aatcagcaat atctactttt tcaatttcaa attgcttatc agaaattgtc ttttcgtaag  13740
cgataaaatc ttgcgcatat tgttgctcat taaaaatagc caccacttcg tcattttcta  13800
aaactcgata aataaatttt ttcattttac tcctcctatt atgcccaact taaatgacct  13860
attcaccaag tcaattatac tgctaaaatc atattaggac aaataggtat actctattga  13920
cctataaatg atagcaactt aaaagatcaa gtgttcgctt cgctctcact gcccctcgac  13980
gttttagtag cctttccctc acttcgttca gtccaagcca actaaaagtt ttcgggctac  14040
tctctccttc tccccctaat aattaattaa aatcttactc tgtatatttc tgctaatcat  14100
tcactaaaca gcaaagaaaa acaaacacgt atcatagata taaatgtaat ggcatagtgc  14160
gggttttatt ttcagcctgt atcgtagcta aacaaatcga gttgtgggtc cgttttgggg  14220
cgttctgcca atttgtttag agtttcttga ataaatgtac gttctaaatt aaacgaagct  14280
gtcagcgcct ttatatagct ttctcgttct tcttttttta atttaatgat cgatagcaac  14340
aatgatttaa cactagcaag ttgaatgcca ccatttcttc ctggtttaat cttaaagaaa  14400
atttcctgat tcgccttcag taccttcagc aatttatcta atgtccgttc aggaatgcct  14460
agcacttctc taatctcttt tttggtcgtc gctaaataag gcttgtatac atcgcttttt  14520
```

```
tcgctaatat aagccattaa atcttctttc cattctgaca aatgaacacg ttgacgttcg  14580

cttctttttt tcttgaattt aaaccaccct tgacggacaa ataaatcttt actggttaaa  14640

tcacttgata cccaagcttt gcaaagaatg gtaatgtatt ccctattagc cccttgatag  14700

ttttctgaat aggcacttct aacaattttg attacttctt tttcttctaa gggttgatct  14760

aatcgattat taaactcaaa catattatat tcgcacgttt cgattgaata gcctgaacta  14820

aagtaggcta aagagagggt aaacataacg ctattgcgcc ctactaaacc cttttctcct  14880

gaaaatttcg tttcgtgcaa taagagatta aaccagggtt catctacttg ttttttgcct  14940

tctgtaccgc ttaaaaccgt tagacttgaa cgagtaaagc ccttattatc tgtttgtttg  15000

aaagaccaat cttgccattc tttgaaagaa taacggtaat tgggatcaaa aaattctaca  15060

ttgtccgttc ttggtatacg agcaatccca aaatgattgc acgttagatc aactggcaaa  15120

gactttccaa aatattctcg gatattttgc gagattattt tggctgcttt gacagattta  15180

aattctgatt ttgaagtcac atagactggc gtttctaaaa caaaatatgc ttgataacct  15240

ttatcagatt tgataattaa cgtaggcata aaacctaaat caatagctgt tgttaaaata  15300

tcgcttgctg aaat                                                    15314
```

<210> SEQ ID NO 5
<211> LENGTH: 10677
<212> TYPE: DNA
<213> ORGANISM: Artificial Sequence
<220> FEATURE:
<223> OTHER INFORMATION: synthetic

<400> SEQUENCE: 5

```
agtttctttt tccgtgtgaa tatcaaaatc aataaagaag gtattgattt gtcttaaatt     60

gttttcagaa tgtcctttag tgtatgaacg gttttcgtct gcatacgtac cataacgata    120

aacgtttggt gtccaatgcg taaatgtatc ttgattttcg tgaatcgctt cttcggaagt    180

cagaacaacg ccacgtccgc caatcatgct ttttttgag cgatacgcaa aaatagcccc    240

tttactttta ctggcttggt agtgattgag cgaattttac tatttttaaa tttgtacttt    300

aacaagccgt catgaagcac agtttctaca acaaaaggga tattcattca gctgttctcc    360

tttcttacga aaattaatta gttagaagct acgatcaaag ttgaatcaca acaaaaaagg    420

caatcaacta agtttttctt aattgattgc ctggtatctt cttaaagact tgaaatcccc    480

tcaaaaaccc gatataatgg gtttacagat atttaagtat ctgattaata aagtaattaa    540

atactttacc aaattttggg tctcgacttc tttaattgat tggtggtaat caattaaggc    600

tcgcagttaa aatttctcag gctttaactg gtcgtggctc ttttttgta ttctttattc    660

agttcgttgt ttcgttatat ctagtatatc gctttttaaa aaaataagca atgatttcgt    720

gcattattca cacgaaatca ttgctttttt cttcttccat ttctaactcc aatgttactt    780

gttctgtttc tggttctggt tctgttggct catttgggat taaatccact actagcgttg    840

agttagttcc gtctctaata gccggttaag taatagccgg ttaagtggtc aaactttggg    900

aaaatctcaa cccgcattaa gttttgatgc catgacaatc gttggaaatt tgaacaaaac    960

taatgctaaa aagctatctg actttatgag tgtagagcca caaatacgac tttgggatat   1020

acttcaaaca aagtttaaag ctaaggcact tcaagaaaaa gtttatatcg aatatgacaa   1080

agtaaaagca gatacttggg atagacgtaa tatgcgtgtt gaatttaatc ccaataaact   1140

cacacatgaa gaaatgattt ggttaaaaca aaatattatc gactacatgg aagatgacgg   1200
```

```
ttttacaaga ttagacttag cttttgattt tgaagatgat ttgagcgatt actatgcaat   1260
gactgataaa gcagttaaga aaactgtttt ttatggtcgt aatggcaagc cagaaacaaa   1320
atattttggt gtccgtgata gtgatagatt tattagaatt tataataaaa aacaagaacg   1380
taaagataac gcagatgttg aagttgtgtt tgaacattta tggcgtgtag aagttgaatt   1440
aaaaagagat atggttgatt actggaatga ttgttttaat gatttacaca tctttgaaac   1500
ctgcgtgggc tactttagaa aaaattaatg agcaagctat ggtttatact ttgttgcatg   1560
aagaaagtat gtggggaaag ctaagtaaga atactaagac taaatttaaa aaattgatta   1620
gagaaatatc tccaattgat ttaacggaat taatgaaatc gactttaaaa gcgaacgaaa   1680
aacaattgca aaagcagatt gatttttggc aacgtgaatt taggttttgg aagtaaaata   1740
agttttattt gataaaaatt gctaattcag tataattaat atttacgagg tgacataacg   1800
tatgaaaaaa tcagaggatt attcctccta aatataaaaa tttaaaattt aggaggaagt   1860
tatatatgac ttttaatatt attgaattag aaaattggga tagaaaagaa tattttgaac   1920
actattttaa tcagcaaact acttatagca ttactaaaga aattgatatt actttgttta   1980
aagatatgat aaaaaagaaa ggatatgaaa tttatccctc tttaatttat gcaattatgg   2040
aagttgtaaa taaaaataaa gtgtttagaa caggaattaa tagtgagaat aaattaggtt   2100
attgggataa gttaaatcct ttgtatacag tttttaataa gcaaactgaa aaatttacta   2160
acatttggac tgaatctgat aaaaacttca tttcttttta taataattat aaaaatgact   2220
tgcttgaata taaagataaa gaagaaatgt ttcctaaaaa accgatacct gaaaacacca   2280
taccgatttc aatgattcct tggattgatt ttagttcatt taatttaaat attggtaaca   2340
atagcagctt tttattgcct attattacga taggtaaatt ttatagtgag aataataaaa   2400
tttatatacc agttgctctg caacttcatc attctgtatg tgatggttac catgcttcac   2460
tatttatgaa tgaatttcaa gatataattc atagggtaga tgattggatt tagtttttag   2520
attttgaaag tgaatttaat tttatacacg taagtgatca taaaatttat gaacgtataa   2580
caaccacatt ttttggttgc ttgtggtttt gattttgaat ttggttttga acttatggac   2640
tgatttattc agtccatttt ttgtgcttgc acaaaaacta gcctcgcaga gcacacgcat   2700
taatgactta tgaaacgtag taaataagtc tagtgtgtta tactttactt ggaagatgca   2760
ccgaataaaa aatattgaag aacaactagc aaaagatttt aaagagttat tttattttaa   2820
gtctttataa catgagtgaa gcgaattttt aaatttcgat agaaattttt acatcaaaaa   2880
gccccctgtc aaaattgacg aaggggggttt tttggcgcac gcttttcgtt agaaatatac   2940
aagattgaaa atcgtgtata agtgcgccct ttgttttgaa cttagcacgt tacatcaatt   3000
ttttaaaatg atgtataagt gcgccctttt aaattttgag tgattatatt ttttgagtta   3060
gaaaaaggga ttgggaaaat ttcccaaaat aatttaaaaa ataagcaaaa attttcgata   3120
gagaatgtgc tattttttgt caaaggtgta taccttgact gtgcttgctg ttacattaag   3180
tttattttta agttattaaa aaagaaatag cttttaaagt ttggctcgct gtcgctttat   3240
aaagctgatt gacttttgat tgcaaactac ttaaagaaaa caaactcgga ctattcgttt   3300
tcttctcttt ggtttgaaca tcagcaatta tcccctcttg attgcctatt ttagcttgtt   3360
tagaagaaac aaaagctaaa agctcctctt gggttttaaa acgctgtgtg gggcttagaa   3420
cgccccttaaa cgaccccttgg tttactttta tactagcttc cacctcgaaa aaaggttctt   3480
ttttaaaatt ctctatggct tcctggcgct gaaaaaaataa ggtataaggt gggcgtttga   3540
acacgtccta gtgaaaatgt accttgtacg ccccttctgt tgtaaattta acgtatacaa   3600
```

```
agggcttgcg ttcatgccga tcaaccaatc ggcaatttgg cgtgtttgcg cttcttgata   3660
aaagggatag taattcattc caggttgcaa attttgaaaa ccgcttcgga ttacatcttt   3720
ttctaagcta ttgatccata gtcttttaaa tgttttatct tttgaaaagg catttgcttt   3780
atggataatc gaccaggcga tattttcacc ttctctgtcg ctatctgttg caacaataat   3840
tgtatttgcc tttttgagaa gttctgcaac aattttaaac tgctttccct tatcttttgc   3900
aacttcaaaa tcgtatcgat caggaaaaat cggcaaagat tcaagtttcc aattttgcca   3960
cttttcgtca taatgacctg gttctgctaa ttccactaaa tgcccaaaac caaaggtgat   4020
aaacgtttca tctgtaaata gtgggtcttt gatctcaaaa taaccgtctt ttttggtgct   4080
ttgttttaaa gcacttgcgt aggctaatgc ctggcttggt tttcagcta aaataaccgt    4140
actcattaac tatccctctt ttcattgttt tttctttgat cgactgtcac gttatatctt   4200
gctcgatacc ttctaaacgt tcggcgattg attccagttt gttcttcaac ttctttatcg   4260
gataaaccat tcaaaaacaa atcgaaagcc gagatgcgcc gcgtgcggct gctggagatg   4320
gcggacgcga tggatatgtt ctgccaaggg ttggtttgcg cattcacagt tctccgcaag   4380
aattgattgg ctccaattct tggagtggtg aatccgttag cgaggtgccg ccggcttcca   4440
ttcaggtcga ggtggcccgg ctccatgcac cgcgacgcaa cgcggggagg cagacaaggt   4500
atagggcggc gcctacaatc catgccaacc cgttccatgt gctcgccgag gcggcataaa   4560
tcgccgtgac gatcagcggt ccagtgatcg aagttaggct ggtaagagcc gcgagcgatc   4620
cttgaagctg tccctgatgg tcgtcatcta cctgcctgga cagcatggcc tgcaacgcgg   4680
gcatcccgat gccgccggaa gcgagaagaa tcataatggg gaaggccatc cagcctcgcg   4740
tcgcgaacgc cagcaagacg tagcccagcg cgtcggccgc catgccggcg ataatggcct   4800
gcttctcgcc gaaacgtttg gtggcgggac cagtgacgaa ggcttgagcg agggcgtgca   4860
agattccgaa taccgcaagc gacaggccga tcatcgtcgc gctccagcga aagcggtcct   4920
cgccgaaaat gacccagagc gctgccggca cctgtcctac gagttgcatg ataaagaaga   4980
cagtcataag tgcggcgacg atagtcatgc cccgcgccca ccggaaggag ctgactgggt   5040
tgaaggctct caagggcatc ggtcgacgct ctcccttatg cgactcctgc attaggaagc   5100
agcccagtag taggttgagg ccgttgagca ccgccgccgc aaggaatggt gcatgcaagg   5160
agatggcgcc caacagtccc ccggccacgg ggcctgccac catacccacg ccgaaacaag   5220
cgctcatgag cccgaagtgg cgagcccgat cttccccatc ggtgatgtcg gcgatatagg   5280
cgccagcaac cgcacctgtg gcgccggtga tgccggccac gatgcgtccg gcgtagagca   5340
caggacgggt gtggtcgcca tgatcgcgta gtcgatagtg gctccaagta gcgaagcgag   5400
caggactggg cggcggccaa agcggtcgga cagtgctccg agaacgggtg cgcatagaaa   5460
ttgcatcaac gcatatagcg ctagcagcac gccatagtga ctggcgatgc tgtcggaatg   5520
gacgatatcc cgcaagaggc ccggcagtac cggcataacc aagcctatgc ctacagcatc   5580
cagggtgacg gtgccgagga tgacgatgag cgcattgtta gatttcatac acggtgcctg   5640
actgcgttag caatttaact gtgataaact accgcattaa agcttatcga tgataagctg   5700
tcaaacatga gaattacaac ttatatcgta tggggctgac ttcaggtgct acatttgaag   5760
agataaattg cactgaaatc tagaaatatt ttatctgatt aataagatga tcttcttgag   5820
atcgttttgg tctgcgcgta atctcttgct ctgaaaacga aaaaaccgcc ttgcagggcg   5880
gtttttcgaa ggttctctga gctaccaact ctttgaaccg aggtaactgg cttggaggag   5940
```

```
cgcagtcacc aaaacttgtc ctttcagttt agccttaacc ggcgcatgac ttcaagacta   6000
actcctctaa atcaattacc agtggctgct gccagtggtg cttttgcatg tctttccggg   6060
ttggactcaa gacgatagtt accggataag gcgcagcggt cggactgaac ggggggttcg   6120
tgcatacagt ccagcttgga gcgaactgcc tacccggaac tgagtgtcag gcgtggaatg   6180
agacaaacgc ggccataaca gcggaatgac accggtaaac cgaaaggcag gaacaggaga   6240
gcgcacgagg gagccgccag gggaaacgc ctggtatctt tatagtcctg tcgggtttcg   6300
ccaccactga tttgagcgtc agatttcgtg atgcttgtca gggggcgga gcctatggaa   6360
aaacggcttt gccgcggccc tctcacttcc ctgttaagta tcttcctggc atcttccagg   6420
aaatctccgc cccgttcgta agccatttcc gctcgccgca gtcgaacgac cgagcgtagc   6480
gagtcagtga gcgaggaagc ggaatatatc ctgtatcaca tattctgctg acgcaccggt   6540
gcagcctttt ttctcctgcc acatgaagca cttcactgac accctcatca gtgccaacat   6600
agtaagccag tatacactcc gctagcgctg atgtccggcg gtgcttttgc cgttacgcac   6660
caccccgtca gtagctgaac aggagggaca gctgatagaa acagaagcca ctggagcacc   6720
tcaaaaacac catcatacac taaatcagta agttggcagc atcacccgac gcactttgcg   6780
ccgaataaat acctgtgacg gaagatcact tcgcagaata aataaatcct ggtgtccctg   6840
ttgataccgg gaagccctgg gccaactttt ggcgaaaatg agacgttgat cggcacgtaa   6900
gaggttccaa ctttcaccat aatgaaataa gatcactacc gggcgtattt tttgagttat   6960
cgagattttc aggagctaag gaagctaaaa tggagaaaaa aatcactgga tataccaccg   7020
ttgatatatc ccaatggcat cgtaaagaac attttgaggc atttcagtca gttgctcaat   7080
gtacctataa ccagaccgtt cagctggata ttacggcctt tttaaagacc gtaaagaaaa   7140
ataagcacaa gttttatccg gcctttattc acattcttgc ccgcctgatg aatgctcatc   7200
cggaattccg tatggcaatg aaagacggtg agctggtgat atgggatagt gttcaccctt   7260
gttacaccgt tttccatgag caaactgaaa cgttttcatc gctctggagt gaataccacg   7320
acgatttccg gcagtttcta cacatatatt cgcaagatgt ggcgtgttac ggtgaaaacc   7380
tggcctattt ccctaaaggg tttattgaga atatgttttt cgtctcagcc aatccctggg   7440
tgagtttcac cagttttgat ttaaacgtgg ccaatatgga caacttcttc gcccccgttt   7500
tcaccatggg caaatattat acgcaaggcg acaaggtgct gatgccgctg gcgattcagg   7560
ttcatcatgc cgtctgtgat ggcttccatg tcggcagaat gcttaatgaa ttacaacagt   7620
actgcgatga gtggcagggc ggggcgtaat ttttttaagg cagttattgg tgcccttaaa   7680
cgcctggtgc tacgcctgaa taagtgataa taagcggatg aatggcagaa attcgaaagc   7740
aaattcgacc cggtcgtcgg ttcagggcag ggtcgttaaa tagccgctta tgtctattgc   7800
tggtttaccg gtttattgac taccggaagc agtgtgaccg tgtgcttctc aaatgcctga   7860
ggccagtttg ctcaggctct ccccgtggag gtaataattg acgatatgat catttattct   7920
gcctcccaga gcctgataaa aacggttagc gcttcgttaa tacagatgta ggtgttccac   7980
agggtagcca gcagcatcct gcgatgcaga tccggaacat aatggtgcag ggcgcttgtt   8040
tcggcgtggg tatggtggca ggccccgtgg ccgggggact gttgggcgct gccggcacct   8100
gtcctacgag ttgcatgata aagaagacag tcataagtgc ggcgacgata gtcatgcccc   8160
gcgcccaccg gaaggagcta ccggacagcg gtgcggactg ttgtaactca gaataagaaa   8220
tgaggccgct catggcgttg actctcagtc atagtatcgt ggtatcaccg gttggttcca   8280
ctctctgttg cgggcaactt cagcagcacg taggggactt ccgcgtttcc agactttacg   8340
```

```
aaacacggaa accgaagacc attcatgttg ttgctcaggt cgcagacgtt ttgcagcagc   8400
agtcgcttca cgttcgctcg cgtatcggtg attcattctg ctaaccagta aggcaacccc   8460
gccagcctag ccgggtcctc aacgacagga gcacgatcat gcgcacccgt ggccaggacc   8520
caacgctgcc cgactttaaa cgtggatcat ttctctttaaa tttatgctga cgacctttga   8580
atttgccttt tttcttagca atttcgattc cttgtgcctg acgttcctta attttttttc   8640
gttctgattc tgcttgatac ttgtacaatt caatgacaag gctattaatc aaacgcctta   8700
aattttcatc ttcaatacca ttcattgagg gtaaatttaa gacttccagg gttgccccct   8760
taatttgaat ttgattcatc aattctgtta attctttatt atttcgtcct aatcgatcta   8820
attcagtaac aataacaata tccccttcac gaatatagtt aagcatagct tgtaattgtg   8880
ggcgttcgac cgattgaccg cttaatttgt ctgaaaagac cttagaaacg ccctgtaacg   8940
cttgtaattg ccgatctaag ttctgttctt tgctactgac acgtgcataa ccaattttag   9000
ccattttcaa ccaacctcta aaattctctc ggttgcaata accaatcagc aatatctact   9060
ttttcaattt caaattgctt atcagaaatt gtcttttcgt aagcgataaa atcttgcgca   9120
tattgttgct cattaaaaat agccaccact tcgtcatttt ctaaaactcg ataaataaat   9180
tttttcattt tactcctcct attatgccca acttaaatga cctattcacc aagtcaatta   9240
tactgctaaa atcatattag gacaaatagg tatactctat tgacctataa atgatagcaa   9300
cttaaaagat caagtgttcg cttcgctctc actgcccctc gacgttttag tagcctttcc   9360
ctcacttcgt tcagtccaag ccaactaaaa gttttcgggc tactctctcc ttctccccct   9420
aataattaat taaaatctta ctctgtatat ttctgctaat cattcactaa acagcaaaga   9480
aaaacaaaca cgtatcatag atataaatgt aatggcatag tgcgggtttt attttcagcc   9540
tgtatcgtag ctaaacaaat cgagttgtgg gtccgttttg gggcgttctg ccaatttgtt   9600
tagagtttct tgaataaatg tacgttctaa attaaacgaa gctgtcagcg cctttatata   9660
gctttctcgt tcttcttttt ttaatttaat gatcgatagc aacaatgatt taacactagc   9720
aagttgaatg ccaccatttc ttcctggttt aatcttaaag aaaatttcct gattcgcctt   9780
cagtaccttc agcaatttat ctaatgtccg ttcaggaatg cctagcactt ctctaatctc   9840
tttttggtc gtcgctaaat aaggcttgta tacatcgctt ttttcgctaa tataagccat   9900
taaatcttct ttccattctg acaaatgaac acgttgacgt tcgcttcttt ttttcttgaa   9960
tttaaaccac ccttgacgga caaataaatc tttactggtt aaatcacttg atacccaagc  10020
tttgcaaaga atggtaatgt attccctatt agccccttga tagttttctg aataggcact  10080
tctaacaatt ttgattactt ctttttcttc taagggttga tctaatcgat tattaaactc  10140
aaacatatta tattcgcacg tttcgattga atagcctgaa ctaaagtagg ctaaagagag  10200
ggtaaacata acgctattgc gccctactaa acccttttct cctgaaaatt tcgtttcgtg  10260
caataagaga ttaaaccagg gttcatctac ttgtttttg ccttctgtac cgcttaaaac  10320
cgttagactt gaacgagtaa agcccttatt atctgtttgt ttgaaagacc aatcttgcca  10380
ttctttgaaa gaataacggt aattgggatc aaaaaattct acattgtccg ttcttggtat  10440
acgagcaatc ccaaaatgat tgcacgttag atcaactggc aaagactttc caaaatattc  10500
tcggatattt tgcgagatta ttttggctgc tttgacagat ttaaattctg attttgaagt  10560
cacatagact ggcgtttcta aaacaaaata tgcttgataa cctttatcag atttgataat  10620
taacgtaggc ataaaaccta aatcaatagc tgttgttaaa atatcgcttg ctgaaat     10677
```

<210> SEQ ID NO 6
<211> LENGTH: 4637
<212> TYPE: DNA
<213> ORGANISM: Artificial Sequence
<220> FEATURE:
<223> OTHER INFORMATION: synthetic

<400> SEQUENCE: 6

```
ttccagagaa tcggatggta ttaattttaa agaacaatca gtattctgaa aaacaaataa     60
atgttctcga tcagttacaa aagttagatt ttaagattga ggaattagaa agtaccttac    120
agatagaaga tgagaggttc aatctggaag aatatcaaga agccatgatt gatgaaaatt    180
atctttatga tatagatatc gtagagaaaa caaagaagta gttcaagcgt ataaccagga    240
tagaatgaaa gataagtcaa atgaaaatga acaatttgaa ggaattagtc atgatattga    300
ttgctaagaa gtatctagtg actttttttct tgattgaaac tcaagataga tatgttattg    360
cttgcatcaa aataaactac atgggtataa tagcaatgaa atgcatttca aaaatatttt    420
gaggaggagt atcatggtta aagaaaataa attttctaag atttttattt taatggcttt    480
gagtttttttg gggttagcct tgtttagtgc aagtcttcag tttttgccga ttgcacatat    540
ggctaaagag ttcggtatac cagcagcagt tgcaggaact gtacttaatg tagttgaagc    600
tggtggatgg gtcactacta ttgtatcaaa tcttactgct gtaggtagcg gaggtctttc    660
cttactcgct gcagcaggaa gagagtcaat taaagcatac cttaagaaag aaattaagaa    720
aaaaggaaaa agagcagtta ttgcttggta atttaacaat atgataaaaa aacaggatat    780
tttctagaga tattctgttt tttaattaaa aaaagggggg cgctcatgaa tctctttgga    840
attctaatga agttaagaat aaatcaagag agtagtttgg ttaaaagagt actttcctac    900
tttaacttaa aactatcgtt aaagctctat ttatttatta atatattctt tgaattttca    960
ttggcatttg ttgttagttt gggattaaga ctaactttaa taaaatcaga tataaatgta   1020
aatttatttt ttataatatt ttttatttta ggaattgttc aaggagcatc aaattgttat   1080
agaacgcacg tctttccttt tgaagaatta aggaaattag caacaatatc ttctagaaag   1140
ataagcttta ttatgattgt tacagactta ttctatattt ttatgttttc atcttcaata   1200
ctatatggat tattgagttt aatatatata agtagtaatg cttttatttt tcaaaaaatt   1260
agtctatctg tattttttttt atttatatac atttgttcat tttattgtag taataggatt   1320
tttggacagt atatctataa taaaatagtt aaggctattg gattaacacg attaatcctt   1380
tatagcattg gagccgcttt atttacttat tttggttttt ttatagtatc attcgtattt   1440
agtaacatag tatattttat aaaaaaatat tttgttaaca tagaaagtgt aaataataaa   1500
gtaatatggg agtcgttttc taaggatata ggaatgtttt atgtaaatag cgccagtaaa   1560
ttttatgaga gtcatgtata ttcatttact tatatagatg ttttttttagt atcggctatg   1620
ttattaattt tggcaatatt actattagct atggaaccaa aactctaccc tttaaaaaca   1680
aaaatgctgc caaaaactaa aatagactta tgcaatttat atgtattttt tttgaataaa   1740
gcattaaaaa aaaatatttt ttttaaatgc agcttgttaa agttagctaa tacaagatgg   1800
attattgcta ataatttcttt tcaaaatata attttgacat atgaatcatt cttttacatt   1860
ggagtaatgc tttcaataat actattgaat tcacaaaata gaatgttgca aatacaacta   1920
ttatttcttt taaatatact tgtaattgga aatcagacat ttgaaataag agaagaaatg   1980
taccccttatc tatcttttgg atcagaaagg aatcaattta cgcttctaag atcgtctccg   2040
aatggtttga ataaagtttt taattcgaaa ctaacgatat acaggttatt tttattaatt   2100
```

```
cctttactta tattaattat cataaatatt gtagtttctg tatacattat gattccggta   2160
atttttgcta tctttttgtt tataacattt tctatgtctg tgtatgtttt ccctatgatt   2220
caaatgtata tgattccttt agctactaaa ctagattaca ctaatgatac agaaattgga   2280
agtgctaaag atgaaaaaat tgttttagag aaatttcaaa cagttccaag atactttttt   2340
aatatcgttc ctttagtgct tacatttatc tttccaattg taggggaaag ttattcatta   2400
ataatatttt tcggagagtt agtatatttc tctttagcaa caataatatt tgtgtttttc   2460
agtaaaaaaa ttattaggaa aggaattttt gttgtacatg cgattagata tcattaattt   2520
tgagaaatat ttgaaaattt ccttctatat atcaatattt atttttttc tgggagtgtt   2580
agcagggatt ataataggtc ctcatataaa taaattggac tattttggtc aggaagtttc   2640
attttatagt gttagtgtta ataatttaaa ggtctctttt tatttcctca ctataggaat   2700
ggtaacaggg ggatttatg catttttatt tatgggtata aatggttata taattggtaa   2760
gttgattcaa tatttataca ttaacaatga actaaatgtt ttgtataaag gtcttcttcc   2820
acattttttt atagagcttt taggattggc aacatttagt atgataagta ccattccaat   2880
atttgttatt ttggtttttt ttaaaacgcc tacacatgta gttcctatta aaaaaatcat   2940
aaagttaagt gtgtttttta ctgtacttgg aatagtttta ataataattg gaggatatat   3000
agaatctaat ataagctatg tagatatacg atagaagttg agatagaaaa ctaatctcaa   3060
aggaagatat ccgcctattt ccaaacgtta tacgaaagaa tttaaacaaa ccattgatca   3120
cgaatcaaaa atgctgaatt aaagatatac tcattaaagg aagagtgggc actattttaa   3180
atttatacaa ccaaggtaaa aattttcgtg aattatcttt ataataatat gtcggttact   3240
taaaattttt gaaattcaca ataaacatat aattaacagt gtgataattt atttgtctac   3300
aagtcaattg ggataggcaa ctctagttgc ataaaatatc tctcacaaaa agtgtttcat   3360
gtattactga atctgatcca tataagttct taagaaagga agataagttt gtacaagttt   3420
actttgaaaa aatacatcgg tattacttca ctattttttt tgttttcaaa tattctaatt   3480
gctgaagagt ttatttttgt agaaaaaaac ttgagttttt tccctaaatt agggataatt   3540
gtgcttgttt tttttatgag tgctcccgct tttgttgttg ttactttaat tttgacttgt   3600
ttagttgcat ttcttattag tttaattaac aaattttaca gtttcaaaag agtatactta   3660
tcgactttat ttgtaaatag tattcagtta ttcgtaaatt tagctttatt tagtgtattt   3720
ttacattaca atttaaattt gcgattgcta agtataatga gttttatgat taatattttt   3780
ttagtagtta tctatcgcaa tttattaatt aaatttgcga atgtaaacag tagggctgcg   3840
aatgtattat caattttcgg gattgcttta tctgtaattt atttggtggt aggagtaaag   3900
taatgaaaaa aataacaatt aacaacttga gtttttatta tgaatccaaa gatattatgg   3960
tgtttgacag gttatcttta gaattttctt ctgaaaaaag ttatgcacta gttggttcta   4020
atggtgtagg aaaaacaaca ttgttaaata ttttatcagg tatatatcaa cccacagggg   4080
gaacaataga atatgacagc actttgtata cagaaaaagt aactaaagaa aaagtagctt   4140
ttataccata taaaactaag ctatatcctt atcttgatgt ttttgatcat ataaagctaa   4200
tagcagaatt atggggaatt aaaacagact atttagaata taaaagaaaa gtactagaat   4260
attgtagccg tctaaacttg gactattata ataagaaagt agagtcttac tctacaggta   4320
tggagtataa actatacatt tctttaatgt tggcaagaga tgtttctctt gtattattag   4380
atgaaccttt tacaatgtta gataaaaaaa gtcgatattt agctatggac ttaatcaaag   4440
```

```
agaaaaaaat aataacaata ttttcttcac atcagaaaga tattgtagaa tatttgtcaa   4500

atgatattat taatcttgac aaactgaagg gagtaaactt ggaaaattat gaaaagaatt   4560

gattacatta ttattatagt ctcactatta gcaacaatag tcgcaatatt tttaataggg   4620

atagattcta tgttagg                                                  4637
```

<210> SEQ ID NO 7
<211> LENGTH: 735
<212> TYPE: DNA
<213> ORGANISM: Enterococcus faecalis

<400> SEQUENCE: 7

```
atgcgcccaa aagagaaaaa aagaggaaaa aattggttaa tcaacagttt attagtttta     60

ctatttatca ttggcttggc cttaattttt aacaatcaga tacgcagttg ggtggttcaa    120

caaaatagcc gctcgtacgc cgttagcaag ttgaaaccag ccgatgtgaa gaaaaatatg    180

gctcgtgaaa caacgtttga ctttgattca gttgagtcct tgagcacaga agcggtgatg    240

aaagcccaat ttgaaaacaa aaacttacct gtgattggtg ccattgcgat accaagtgtc    300

gaaattaatt tgcccatttt taaaggattg tcaaatgtcg ctttattaac tggtgccggg    360

accatgaaag aagatcaagt catggggaaa aacaattatg ccttggctag tcatcgaacg    420

gaagatggcg tttccttatt ttcaccttta gaaagaacca aaaaagacga actcatttat    480

atcactgatt tatctactgt ttatacatac aaaataactt ctgtagaaaa aatcgaacca    540

acccgtgttg agttaattga tgacgttcct ggtcaaaata tgattacctt aattacctgt    600

ggcgatttac aagcaacgac gcgaattgct gttcaaggaa cattagcagc aacgacgcct    660

attaaagacg ccaacgacga tatgttaaag gctttccaat tggagcaaaa aaccttagcc    720

gattgggtgg cttaa                                                    735
```

<210> SEQ ID NO 8
<211> LENGTH: 681
<212> TYPE: DNA
<213> ORGANISM: Artificial Sequence
<220> FEATURE:
<223> OTHER INFORMATION: synthetic

<400> SEQUENCE: 8

```
ccaaaagaga aaaaaagagg aaaaaattgg ttaatcaaca gtttattagt tttactattt     60

atcattggct tggccttaat ttttaacaat cagatacgca gttgggtggt tcaacaaaat    120

agccgctcgt acgccgttag caagttgaaa ccagccgatg tgaagaaaaa tatggctcgt    180

gaaacaacgt ttgactttga ttcagttgag tccttgagca cagaagcggt gatgaaagcc    240

caatttgaaa acaaaaactt acctgtgatt ggtgccattg cgataccaag tgtcgaaatt    300

aatttgccca tttttaaagg attgtcaaat gtcgctttat taactggtgc cgggaccatg    360

aaagaagatc aagtcatggg gaaaaacaat tatgccttgg ctagtcatcg aacggaagat    420

ggcgtttcct tattttcacc tttagaaaga accaaaaaag acgaactcat ttatatcact    480

gatttatcta ctgtttatac atacaaaata acttctgtag aaaaaatcga accaacccgt    540

gttgagttaa ttgatgacgt tcctggtcaa aatatgatta ccttaattac ctgtggcgat    600

ttacaagcaa cgacgcgaat tgctgttcaa ggaacattag cagcaacgac gcctattaaa    660

gacgccaacg acgatatgtt a                                              681
```

<210> SEQ ID NO 9
<211> LENGTH: 54

<212> TYPE: DNA
<213> ORGANISM: Artificial Sequence
<220> FEATURE:
<223> OTHER INFORMATION: synthetic

<400> SEQUENCE: 9
atgcgcaagg ctttccaatt ggagcaaaaa accttagccg attgggtggc ttaa 54

<210> SEQ ID NO 10
<211> LENGTH: 57732
<212> TYPE: DNA
<213> ORGANISM: Enterococcus faecium strain CK135 plasmid pPD1

<400> SEQUENCE: 10
tgatttgacg aagcaatgct tttgtgacac ccatttgagg aatttctcta tatttcttcc 60
agatcatttt cccatgttct aaaacctgaa ccgctagata aaatcgctcg ttttccaata 120
cataacaatt tcctgtcttt gtatgtatcc gatagacctt ttgtaaaatc attgtacccg 180
tcactttttg tttcattctt gaacaccagc cctttctaaa atttagcgat aaaaaccaaa 240
aaacggggaa catatacatg aactgtatac gttccccgtg tactgcaacc atcattccac 300
catacaaaac aatttattta aagtaatctt tttcctagac caataaagga gtttaaaaag 360
gtctggaaat tcacttaaaa aaatgttata atgtatgttg taacttatgt tgcagtgttc 420
gagaaccgag tatagttcat gggatcagca tgaattattt aactatcctc ttgggttggt 480
agcccaaaga tagtcggttc ttatttttag ttactttttt ctagtttcat ggtataattc 540
gtatgttgga cgaagtcata ctactagtgg tgtggctttt ttttaagaaa caagagttaa 600
tattagtgca aacaataatg cagctatatg ttttttttgt tgtttcatta aatttacctc 660
acttagtaac tattcattac agttactact atagcattaa agtttactca ttacaagtat 720
atgtatttta aaaaagacgt ttccgggaaa aataattcat tttttattta ttttcttttt 780
tttgccgatt ttcgtcatat tcagaataca tttataggag ttgaatatat gcatttaaat 840
gaattaatga aaatacaaag aaaaagcgag aaattatctc aagctaagtt ttatgaaggt 900
atttttcagc gtaattcagc aagccttttt gaaaaccata atgaacattt tttaaaaatt 960
gctgatttgc caattcttgc agatagaagt aatttaacaa tacctgaaat aattagaact 1020
tgtaatgaag attttaaaag tgtttttgat aaagatttag aaacatatta ttttgttctt 1080
tcaaaaattc aacaaaatcc tgattcagaa tacaatcaag aactctactc tctttatcaa 1140
aaatctatac atgaaaaatt tacttcgtta aaatacatga atttatattt acttataaaa 1200
ttgcaaacct ctagtttgat ttcagaaatt attcctgtgg ataaacaaga tttagctgat 1260
ataaaaaaga tgttttcatc aagcaaaaga tttgtattgt atcactataa aattctttct 1320
aatctatgca ctatattccc ttactctgat cttcagacat tgatagagca actatttcct 1380
ttacgtgaag atagtgacga gcagattaaa gatacagctt gtttatcctt gtctaatgca 1440
attgctctaa gtatatttac aaaggattac agttcttgct ttatacttct aaatcacttt 1500
gaaactttgt tatcaaatta cactagttat aaatataaat taagtttcat agcttcaaga 1560
aatatgcttc tatactttac ttctggagat atagagcata ttatgaaagt attctcgtat 1620
gttgaaatat tgaaacaagt ggaaagccct gaatatgttg agcaattcca taaaaactta 1680
caaacaatca tttctaaaag tgatgatgaa aaagcaaaac aaatatttgg tgttcttgac 1740
gatgatggac aagtattaga ccccaaaaat tttgaccaca aaaaaataga ttaacttaaa 1800
acccaaaaaa taagacatta aaaatcttat tttttgggtt ttcctatcct tacagttaaa 1860

```
ataaattctt aattatatct agtccaccta tgatatttcc aacagtacca ccaatacttg   1920

ctaaaataaa taccaaaaat attctcaata ccctattttt atatattttt tttattgata   1980

gcaaatcttc atccattgtt tgaaaatcat gaactttagg ttttctgatg gtagcttcta   2040

ctattgcaga aaatacacct attgatacca ttggtagtaa cgttgcaagt ggagcaagta   2100

ctaaagaagt aataaccgtc aatggattag caagtgctaa gacagtaaag agtgcagcta   2160

cgccgccatt ccatataccc catcgaatga tttgatttat acctatatcc attcctaaaa   2220

caaaagaata aatcaataaa ccaataatta ttaaaggtat aatactttct aaaaccctag   2280

ttgaccaaag tttgggtggt aatccgtcta attcctcaat atttgctttt cgattttcct   2340

ttatattttt ctcaactcca tttaagtgag cttgaccaat aacaacaact atttttctc    2400

cttcttcatt tagaattttt gtagacatat ataagtctct ctcaattaag aaagattccc   2460

acaattcagg gtatgtttgc tgtaattgtt caaatatagg ttcaaaattt tctgaattaa   2520

gaagtttctt catttcttct ttagaatctt ctgctccttc taaaacttta ccaaaagcat   2580

gtgggaaaag agcttttttt cttagaggta tcaaccgcca aaaacgttta aatgtaactt   2640

gtgaatctct atcgactaaa gctaatttag ccccaatttt ttctgcacta ttcactgctt   2700

ggaaaaattc tgctcctggc acagaatcat ttatttttgc caaatgtttt tgaattaaac   2760

tgtatattac acttgagatc aaaactatta attttttttg tttaattact tgaacaatat   2820

ctgtatctga ccattcatca ggattcatat atttattgta ccttgtttta tcccattcta   2880

aacaaacagt atctggactt tccttttcaa ttacctcttt taccaattct gcactctctt   2940

tagatatatg agaggttcca acaagtataa tttctcgttt atctaaaaaa attctacgta   3000

ctaattccat acttcctcct ctaattttgt accatcattt ttttgtaatc atatctagct   3060

ccaacagggt gaatcactaa gttccttatt gtattttttt gaagtcgagc tattcccact   3120

tgaaacacgg gtataacgcc cgcatcatct atcactatct tttctgcttt ttttaattcc   3180

tgccaacgtt tagaggaagt gtctttaatc aactcatcgt agtttttatt agaatatcca   3240

ccgtgattca atggactatt ggtttcaaag tttgctaaaa aactaatagg gtctgcataa   3300

tcagcttgcc atccgcttag acttatcgca aaatcttttt tagtcaaacg ttccataaat   3360

acattagcag gtactggtgt gatattaact ttcaaccctt ctaagttttc ttctaattga   3420

ccttgtaaaa attctcctgc tttttttca aactctccgt cacctactaa aatatctagt    3480

tctagttttt cagagacact atctttactt ttgacagttt cccaataagt tcttgcctgt   3540

tttttgttat actctactaa tttttcattg gcaaaatcct tttttgtttt tggattataa   3600

gccatctttt caggcacaac accaacagaa ggaatagatc cattatctaa taatttttcg   3660

actaagctat ctctatcaat tggatagcta atcgcttttc ggacattttt atttttttaaa  3720

agtttattct ctccagtttg gttcatttct aaaaacatcg tattcgccat taacgttgtt   3780

gaatattctt tatctttttt gtattgtttc gcatattctc ccgcaagtgg cgcatcgtcc   3840

agttgtccgt cattatacaa attaattcct gtattaattt ctttgacaac ttggaaatta   3900

attttatcca tagagacatc tttttatcc cagtactctt tatttttaga aatcgtccac    3960

ttatcagaag tgcctacccc ctctaaaatt gttaagttaa atgccccatt tgttacaatt   4020

gctttttttag aagtaccata gtctttcccg tactctttaa ttgctttctg ctgtactgga  4080

tagtaagcgg ttaaggataa cagatcagta aaataaggtg ttggttcaac taattcaatt   4140

tctaatgttt tctcaccaat acttttcact gctaaagtat cttttacttg ttttcctgaa   4200

gcaatttctt tggcattttt tatagcagaa aacagttcca catttggaga agctgtttta   4260
```

```
ggatctacaa ctctttgcca cgcggccaca aaatcactag cagttatttg tgtaccatca   4320

gaccacttag cgccatctct aatcacaatg gtataagttt tgccattatt cgatactttt   4380

ggttgaccag ctgcgatggc tggttgcggt tgattttttt catctaatcg atacaacccc   4440

tccatcacat tggctaataa agttatactc gtttgatcta cagcagttgc tgggtctaaa   4500

ctttggacag gtgtccctgc agtcaaagtc gctacctgtt ctactttttt ttcggttaca   4560

tcttgtgaat cttttgtggc agtatttata ccacaactgg ctaataccaa aggtaataac   4620

ccaataccta aaaaacaaaa cttcttgtac ttcttcattt ttatcaacct ccgtagttta   4680

aatttgctaa ctaattctag cgatatacaa ataaaataac caattaatag ctattatatt   4740

tacaatttta tcaaataaac tttaataggg atacaaaata cagaatgaaa tttatccaaa   4800

cgaatgaatc aattacttat tgttcaatcc aattatgcaa agttatctca gaacctttag   4860

acttattccc attatttata ttttcttttt ctaacgcaca tgcaacaaat aaattataaa   4920

acgacttgta gaataggcct tttggacttt ttacagtaga atctgtctta attttatgca   4980

tcacacgacg caaacatttg tcaatttctt cttgataatc ctctccaatc aaaacaatgt   5040

tgtattcttt ttctactttg gtttttgcac gtataattgt tcctacttgt tcatgggctt   5100

cttgaatagt atcagaaaaa gcagcaataa attttaagct atctttgctt aggaaagtgt   5160

tctcttgaac ttctgaaaac tgatcgagca ataattgttg ctgcaagact tctttttttag   5220

tatctaatgt atctaatgta tctaaataag aagtatagaa tagattgtct gcgattttcg   5280

caattacagg attttcgttg atatcattga ctttttctgt atttgcgatt ttcgcaatta   5340

caggattttc gttgatatca ctgacttttt ctgtacttgc gattttcgca attacaggat   5400

taacattgtt ttgttcctca ttgattttga aaacatcttc tgaagtaacg ttaggttttc   5460

cgagatatag caggttaggt gtagtttcta tttttccatt aattttcttt actctacctt   5520

ttttttgttt aagaagatta actgcttcaa gctctttttt tatttttgat acttttcctt   5580

ctctgcaatt tagcagagtc attaattcag caactgtgta gataaaataa acattgtctt   5640

cactatctac ccaattattt ttaacggaat tatcaaaccg atcttttaaa agcatgtatg   5700

caatttttgc atcattggat aatgatttgt aaacttcatt tgtgaaaaat acttttggca   5760

tttgatagta tttttctctg taaatttctt tagatttgta aaattgaaaa ttttccattt   5820

taaagctcct ttagaatgta agtgttatca atcgtccacg tattcttatc ttgtaaacta   5880

caggaataca attcgattgt aaagtaatat tttaacgcaa tatttacaca agtacacaaa   5940

tacacaagtg caaaaatgta tttgtgtaaa tatctaattt tgaatattat caggttaaac   6000

aaaattatgt gtacatttac acatttgtaa aaatacacat agcggaagac tttcattatt   6060

gattatatta ctaattacac aaataaaaat gtgtaaatgt gtaaaaaaac attgattatt   6120

taaattgcct attgtataat ttaagcatag atatttacac aaatgtaaat gtgtaaattt   6180

gaaaaattac acataaaaaa aggaggaact ttcatgatag agcttatagt agaagagttt   6240

gaacaactag ccaatctatt agaagaaagg tgcagagtaa ttagtatagg taaccaaaaa   6300

ggtggtgtag gtaaatcttc ccttgttcgt ttacttccgt ctgtgttagc tttttcaggt   6360

aaaaaagttt tactcataga tatggaccct caagcgaata caactaaaag tatgttcgta   6420

acccgaaaaa attattatga agacgaagtt gttgtattta aaaaaacatt aatggctggt   6480

atcgttgaag gtaatcttac tgatctagtt atcaacgttt tacctaattt agattttatt   6540

ccatcttcat cagatttaga aagtttccct acgtttctgt ctaaaaagtt tggattagtt   6600
```

```
gataaaacag accctgattt ttatgaagtg aaagacaaag cctatgaata tttcaattca   6660

ttgattgaat cattaaaaga caattatgat tatatattct ttgatacgcc gcctacggtt   6720

tctgattatg ttagagctgt atcatatgtt agtgattata tactaattgc atttcaaact   6780

cagagcgaca gtttagacgg tgcaaaagaa tttttagaag atactttaat acctttagta   6840

gaaaatacaa gagcagagtt tgaagttgta ggtattttgc ctaatcaaat gactaagaac   6900

ggtagtattg acacttcatc acttaatgat gcatatacaa tttttggaaa ggaaaatgta   6960

tttgagaata ttttgccttt taaaaaacca atacaaaaca tccctagaca tggcgttaca   7020

ttagaaggtt attggaatag taaaatgtac attgatacat taataccaat tactaaagaa   7080

cttgtcacaa gaattagttt aatagaagga gattagacca tgactgaaaa tagaaaacca   7140

tcactaatag gaaatagaaa taaaaatctt tatcaggaaa cacctagacc agaacaacct   7200

tacagtggag ctgaaaccat acctaaggat atcttagcta atgagagggg aacaatacgt   7260

gtgcctcttg atcaaaaaat agaatttgat gcattgttag cgacttctga atatcattat   7320

acttatgagt taatggctga acttgtatat gaagcagtca aaaacaagac taaggaagag   7380

aataaaaaat atcaagaaac gttagcaatg ttacgagaga aagaattgaa aaaaatagag   7440

agaaagaaaa tgaaaaaata aaaatattca catgtgtact tttgtaaatt tacacatgtg   7500

aatattttta ttatgaatca atatatagca agtaataatt agttaaaaaa ttacacaatt   7560

gtaaatgtcc acatttacaa aaatacacat atatatcaac gacagtaaaa ctccctaaat   7620

aatatagcta tctttcatca ataatttttt tagttcgtct gtgatgttct aagtgtagca   7680

aataatcgtc ttgcagtttt agaaggtctg aatagacctg atccatagtc ttgctggccg   7740

acaaagaaag agaataaata aatgagatag gaagtgtttc aatttttttg ttgcgagtaa   7800

tccaagaaga aacagttcct tgagagaaag catgtaattc acaaaattct tctacagtaa   7860

tccctagttg cttgataatg tatgcgttga tagggtgtgg atatacaaag gtttttctag   7920

gcatggtggg taagtttcct ttcttagatt attaatgcgt ttgcagtaat attgtactaa   7980

aaaacatgca ataagggaag ggcgtatctg cttctttttg gttgacctcc tttaaaaata   8040

tgttatacta aaggtgcgaa acgacattaa atcgtacaaa taacacaaaa agcaatccta   8100

cggcgaatag gattgctttt ttttacacta gttgcgactc ctagcgtgtg tgttgatagc   8160

agcttacttt cggttatcgt cttcctcgtc caacacacga gaaatcattt ccagaaccaa   8220

tcctacaaag atcggtgcga taaccaacga cattaaatct ttcacaaata acacacctcc   8280

aatcgaggcg agctgccgta ttaattatat catagattga aattctgcca attcaataat   8340

aaaaccttca acaatttatc tagctgttct atgatctttt ctaagcgtgt aaactcgttt   8400

acaccaggaa catttatact tgtttgagtc actcgtaact ctgcttgcta gacagccaca   8460

gctgcattct acataagcca cttggtggac gctgtctcct agaggaataa tggtaccatt   8520

ataatcatat gccttcatta cgaaaccccc aatcgctaaa atactcatct aactttttct   8580

gctctttttt tgacaaagta ggggagacta aaccttgaaa agggtttgaa tttactcttt   8640

cttcttgttt tattctacta gaatgacgat acatacacac aaagtcaact tcttctatac   8700

tataggaatc ttcaccaatt attattttgt tttcttccgc atatcctcta aaagttccta   8760

taactggtct aggaaaagga ttggtttctg aagacacaag taataaatat aatggcttat   8820

tttgtttgat tgagcgagaa aaataagaag aaaattcttt tctattttgc ttcatttggt   8880

tgtacctaag ccaacagttc cacctgcatg gccaccaaca aggcttgctc gtgaaattgc   8940

tgtggcgcct tccatcagtg aagaagcatg tatcagtgct ttaaacccaa atttctgacg   9000
```

```
aattttatca ataagaaaat acatatccgt ttcatgaatt tgctcctccg gaacagaaaa   9060
taaatccagc tgtaaatttt tgttccatac aagacggcca taggataccc ctaaatttcg   9120
tacgtcgacc cctggtgcgt aattctcttc aaaaagacgc agtacatgtt cagtcaagac   9180
ttttgtatta ttacttggtt ctactttcat ttgtctacgc cagccgtttt ggccgtattt   9240
gtctgtctga ccttttgagt agccaacaaa caaagagaca caggttgtct gacacgatgc   9300
catgcgtaag cgactagcga cctggtccga caattccttc aaaaccaatt ttatttgttc   9360
tttatttgca taatctttgg gtaaaacctg actattgcca aatgattttt ctgttggccg   9420
tcccgctttt tgccctaaaa aactacgatc tatgccccat gagtgcgcgt acagctgtag   9480
ccccatgata ccaaaacgct cttttaacat gtaaggttca atgtgcgcta ggtcataaat   9540
ggaccgaata cctagctttt ttaagcgagc agccatgcga tttcctatcc cacaaaattc   9600
tgtaagaggg gagattggcc aaactttttt tggcacatct tcatagcgcc attcagccac   9660
aaagcctggt gcattctttg cttcattatc caatgctaac ttggccagca acggattttc   9720
cccaattccg attgtcacat acaatcccat atggttataa atcacacgtt gaataatctt   9780
ggccagttta taggcggtgt cacacttaaa ataggtcagc gaagcagtca catcaagaaa   9840
cgattcatcg acactgaata cagaatgatc ttcatcagaa acaaagcgtt tatataaatt   9900
gttaatttct tgatttttct tcatgtataa tttcatgcgt ggagatacaa taattaagtt   9960
cgggtggtcc ggaacttcat ttttccttgt aacattggaa atgcctaata cttttttttgc  10020
catagggggaa gcagcgagta ccaagccacc cgaattttca gaattgctca tgaccacaag  10080
cattgtcttc aatggatcaa gtccacgttc tacgcattcc acgctggcat aaaaactttt  10140
tacgtcgata caaagcacat cacgactggg ttctttcgta taatcgaacg tcaaattcat  10200
ccaaaatccc ttctttctac taacccatta tacgaactaa tgttctcttt agcaactagt  10260
aaaattcagt tttccgtatt tttttacacc tgtaaacttt tggcatagtt ggactgaacg  10320
cagagaggga aactatacaa aacgttgaag gccagttgag caaagcgaaa ccaattattc  10380
gtcttttata ttccagctgt attcctggaa caaataatta ttcgtattta aaagggattt  10440
ttcccattat ttccgtctgc agtctatcat ttaacaatat aaatacgaac gttcaatata  10500
ttctttgcat aactaccgat caatattttt gaaaacggct tagaattgct ctctcatcac  10560
tataattatc attaataatt gaatatagaa taaccccccaa aaaaagattt tcaggggtgg  10620
ggttttattt acttactaat tttatcgatg caagctttcc cagtttcatc aagcaatggt  10680
gtaattcctc ctttaggagt ttctaaataa ttcacaccag taacagtatc aactacaatt  10740
ttatagccta atagagttaa agattcactt tctttttcaa caaaacgttt gtctttaaat  10800
acatgttcct tacatttatg tctgtctaat ggtacgttat ctgattgttc tatcaactca  10860
ctatttgaat tatccccggc aaccatcatg cctaaatttt tatcataata aatatattct  10920
ccacctagta ttaaggttaa tggcataaaa atcttccttt ctttaatttt cttaccgtcc  10980
tttttgttca ttttctacgc acaatcaatc gattaaacag attgcctctt attccaacaa  11040
gtaaatttca agtgcaaatc atcctatttt taaataggat ctgttgtcaa ctttttctta  11100
attctatcaa aaaccggaag atttgcttg caaaccaatt ccctttttact aaattaaaac  11160
aggtttttat ttagtatgaa acagaaacca acattgaagt aaatctcatt atccattaaa  11220
tttattgcaa agaccactaa aatatttaaa aaataactat gatttcattc ttattgatac  11280
accgcctgca atgggaatga tttcggcaaa cgtttttaat tctgttgacg atgttttaat  11340
```

```
tccatatcat cctgaagtat attctttcag aagtatggtt aagtcaataa aatcaattaa  11400
caattttaaa agaagtaaca aaaatttaaa tataaaagca gtgattccag ttaaaataag  11460
aaaagtcctg actcacgagg catttttaca gtctgcacaa gcattgtgtg aacaaaatag  11520
tatattaatg actaatacaa caattccaga atcaataaga tatgcggaat ctataggaaa  11580
atataaatta cctgtcacac ttattgatga aaagaataaa tccttaatag gatacaaaca  11640
aatttatgca aaattagcaa gggagttgac ctatattggc tagaactaag aaaatagatg  11700
gcttttcatt cgaagatatc gtcaacacta atatcaataa cgatattaat gataatgtta  11760
atgtcaatga taatggtaat gttaataatg atgttgatga taatttaaaa gacaaggaaa  11820
atttcttgga aaatttaaaa cctgaaaaag agaaaaaaat taaaacatta ctctatattg  11880
attctgatat tgccaatcat ttggacttct atggcgagaa actcggaaaa aaaatggtgg  11940
taaaagtaaa ttttgtaatg aattatttaa aaaattttta gaagataata gtttatggtc  12000
ggaaaaaatt gcttctaaaa aaagaaaata aaacaatagc cataaatgca catatattta  12060
tacgtatgtg tgtttcatgg ctattgtttt tatttcagga acttaagtga aaagtaacaa  12120
ccagttatga cggccagccg tcaaccatga catcaactaa tttattagcg tacgctacaa  12180
taaattgagc attttcttct gtctcaatgg gcacaagtgt gtcgccaata aattcataga  12240
gtggttgaga aataatttct ttcattaagt ctgtaggtaa aggaatcagc cctggggttt  12300
tatccatcag tctttttttct tcctcataaa aggcggtcat taaagaaagc tcatctgtaa  12360
cgggatctaa gcagccataa ctacaagaca acatccggtc cacaaccaca gcttcaggca  12420
aacctagtct caaagcgata tacgctctaa caaaatattt ttgatggata cttgccaaca  12480
ttgggcaggc atcctgccag tccaacacga tactctgttc ctcatcttct tcatccatga  12540
ggcctagtaa tacttctatg cccgattcta attcgtcttt ttcaaaaata cgctcaatag  12600
tcattgcttt taatcgtgga atagaagcta atatgttttc aattaatgct tcccaacgaa  12660
caagtttttc tttaaagcgt tttacttggg cttgttgttc taaagaaaga gacgtttgtt  12720
cccagaatga aatttggtct ttataagctg ggacaagctc tttttcagat aagtacaagc  12780
gctctgttct taagactgtc tgatcatcta attgataggg aaccttaaga gctggctgta  12840
aagaatcgta gagctcttca gcagattcta gttgacttga tagtagttga ttcatcaggg  12900
gaaaataatc aatcgtgtat aaattttgat tttctgtcat ttgtttctcc aattcttgga  12960
aatatttttt aagactttat tagaactgcc catgttcttc tttgatttca acgtactgtc  13020
ctaggttcat tttgtatttc cgatgacagg ttggacactc atagtaattt ttttgataaa  13080
cattctttgc tagctccccg caatcacatt ccacataaaa agcgatattt cgattaaaac  13140
tagctatttc aataccccaa cgatcataag attttcgctt cataaaaatt ttcctccttg  13200
tacattttac taacgattat aaataccgtt gccattcttt caactgttga ctaattaacg  13260
cataaaattc gacttctgat aaaatggtaa tctcatgacc taacgcaatc aagtcccgcg  13320
cggtttgttc ctttttttgta tagagagaat catcaaacaa cgacttagaa tactgaccac  13380
aaaccaggaa atttgttttt gaagtaacac ttgattgaca atggccgttt aaagagtgaa  13440
ccaaaccgat ggcttgggtt cgtgtcattt gctgcagcgt tccagtaaaa acgacccttt  13500
gatccgttaa gtccattttc aaactctccc ttcccgtcta atagctgcta tatctatcaa  13560
gaaaagtggt gcaaggtatt ttcatattct ttcactcgtc gataaaaggt atttcgtttc  13620
acgcccaatt gctccatagc atagactgca gttatctttc ctgctttcca gtcagaatag  13680
atcgcaggaa attcaggagg taaagcaatt ttctttctgc cgaattttac accctttcgt  13740
```

ttcgcagctt ctacgccttc tctttgccgg ctattaattc gtttccgttc gtcttcggcc 13800
atatagctca gtaattgcag aattaagtca gagataagcg tctctaatcc atctagttgc 13860
ttgtaactag cagtatctaa cagaggcatg tctaacacag aaatatcaat ctgcttttcc 13920
ttagttaatt cccgccattc ttctaaaatc atttgtttat ttctgcctag tcgatctaat 13980
gattgtagat agagtaaatc tccctttcga aacattcgtt tcattaattg atattcaggg 14040
cgtttaaaat ctttgccgct ggctttttca ataaaaatat attcttcagg gattcctaat 14100
tctttcgcag caattagttg tcgttcgatc gattgatcat aactactgac ccggatataa 14160
aaaaatttc tcatcattat tatctaccct tttttcacta aaatcgtttc aaaaaactta 14220
cattaaatca gaaacgtttc aaattgtatt atgtgattat tatgccatat ataaacaaag 14280
aaaatcaagg catttcaaaa agtatacttt ttgaaacaga tgaaaaaaat cagaggaaca 14340
aacaattatt ttgcctgttc ctctgatttt tattcatttc acttataaat aagattaatt 14400
ttcgctaagc attcttcgat tacttcttca ggggcttcct caacgaaatc aaaacctctt 14460
gaaacaatat caatacttct atgatgttcg agcaatattt cgcctgttat tttcatattt 14520
ttagtaagag gtacatgcag aggaaacgat tttattttac ttgtgatagg cgcaacagat 14580
accatatttt taagatatgg gaggcgcttt cctagaataa tacatgggcg ctttccctgc 14640
tgttcgtgtc ctttagttgg atttaaatta atatacacaa catcgccttg ctttaattca 14700
tttacacttt ttttcataat aactcttctc ctacaggact gccccaatca tactctgttt 14760
catttaaatc tccaccttta taatctgaaa ataattcttc tagcgtatta ggaaatgtcg 14820
ttttgggtgt aaggataatt tgaccttgtc taataaccat ttcaaatttg gctgtttggc 14880
cctttatacc tagctctgct aattcttctt tagataatcg aattccctta gaattacccc 14940
actttttag ctcaatttct ttaactaaca tatgatcacc tcttctcgtc cattatacca 15000
caaaaggata tacaagtata tacatttatg tttttcttt ttgcaacatt ccaacagtac 15060
tttcattatc ctattatgaa acgttagact tgcatgtttt taactttcac gacattatta 15120
tcggtaagtt tagtcattaa ttctttattc aaaaaagatt gtgaactttt taggtagtag 15180
aattcttata ttagtgcttc taattttta cgtataaaat ttgaacttga ccatccataa 15240
atatattttt aagcagttaa aatccttaaa aaaagcagac ctcaaggcct gcttttgaag 15300
aaactattta tccaattttt cttttacatc tccaacaaca tcttcgactt tgtctttcgc 15360
atcagaagcg acttctttta ctttaccaat agcttgatct aagaaacctt ctgcttttttg 15420
ttgatcatcg ccagtcacat ttcctgccac ttcttttgct tttcctttga ttttatctgt 15480
cgttccttta tctgtcataa tgaattcctc ctgatatttt attttttag ttgtttgtat 15540
ctgaagactc taattcttta ctagcacctt caatggcttt actagctttt gtttttcctt 15600
cttctacttt ttctttgcct ttttcaactg cttcattggc tttatctttc gcttcatcaa 15660
gcgcgctgct tccttttcc tttgcctctt ctactttaga agaagtagct gtagaattct 15720
ctgttttctt ttctttactt ccgccacacg cagctaatga gaatacagct actccggcag 15780
caattgtcaa tacaatcttt ttcaactttc ttcgacctcc gtatatcaat tttttatggt 15840
acatattaat tataaaacaa atacatcaaa aaatataatg gtctaaagtc tgattttta 15900
tcttaaacac taaaaaagtg ttgtgttgga aagttctcaa aaacaaaagt caagtccaat 15960
ttttatcctt taccttaata tatcgattaa atctttttt gctgcttctg atgcaggcat 16020
tacagagaaa actagaccaa taactgaaga gacgccaact gctaataaaa tagtaaatag 16080

```
atcaactgat acgtggacct ttatcaagga gccaatgcca taagcaaaaa tcattcctaa  16140
taaatagcca attatccctc cagaaatagt taaaattaac ccttctaaaa ggaattgtaa  16200
cataatcgat tttcgagtag ctcctaatgc tcttcttata ccaatttctt ttgttcgctc  16260
agatacagag atatacatca tattcatgac ccctacccct gcaataaaca atgatattcc  16320
tgctacagct gttataaaat aagtaattgt actgagaatc tgaccaattc ctttcgtcaa  16380
cattgctgta tctaatactt catattctcc tagatgtctt aaactccctt tctcttttaa  16440
ttgttttatt actttagacg tcactttatc gggtttaact ccttcttcta aagttaatgt  16500
taaagaggag gtattttttt ccgatttaaa ataatagcga tacgcatctt ttggaatttc  16560
aatatttgta tttgacaagg aaaacaaatt atcttgctct tctccaggaa aaactcctac  16620
cactctaaat aattcttgct caatttcaat tcctttaccc aatgctcgtt ctgatgtatt  16680
aaatagctct ttggctgtaa ctgaatcaat tgttgctact ttatttaata attcactatc  16740
ttgacctgtt aaattcctgc caatagaaac tttttttcct tcagaatcta taagtttaat  16800
ctgtttattt tttttatttc ctctaataga caaatctttg tagatttgct cttcatcaat  16860
tttagaatag tcagcttttt ttaccccttc tacatttctc actgtagata agtctacatc  16920
ttgaaagaat tttgtatttg tatcatataa ggacgtatca ctcggtgtaa aatttaattg  16980
aatttccaca tttttagaat cactcttagt aagatttttt acggtatctt tctcgaaccc  17040
tcttccaata gctaaaattg taataacaga cgatattcct ataataattc ctatcatggt  17100
taatacacta cgttttcgat tatttttaat tgctttccaa gcagaacgca tgtttacata  17160
aagattcatt gcaccaactc cttatcttca ataatcgcac cgtctctaat agtaatcaac  17220
cggtgacaat aaggaacgac ttcagggttg tgcgtaacca taataagcgt tacgtcatct  17280
tctttattta aagtagtaaa aagcttcata atctcctctg aggtgtgtgt atctaaagca  17340
cctgtcggtt catctgctat aataaactta gggtgattaa tcaatgctcg ggcaatggcc  17400
acccgctgct gttggccacc agacaactgc tttgggtatt tatattcttt tccttttaaa  17460
ccaactctat ccaatacgga aaaaactttt tccttcgttt taaaaggaga caacccatta  17520
taaagaagag gtagttctac attttcataa actgtgttac tctcaatcaa actaaagttt  17580
tggaaaataa aacctactgt ttgatttctt attttagaaa gaatgtcatc tgctgtatta  17640
accaaagatc tgccttcaaa caagtattct ccctcaaact tacgatcgat aaatcccaaa  17700
agattaatta atgtcgattt gccagatcct gaagggccca tgatcgctat catttcccct  17760
tttttgatgg ataaatgaat atcttttaat acatgaagtg actcctcttc atttgcatag  17820
tatttattta tcttattgag ttcaatcatt gtttcaccgt cactttttgg ccatctttca  17880
gactagtatc tgggttttca atgattgaat cattttcttt aagtccagtc tttactacgt  17940
atttatcatt atcttctttt acttctattt tctgtttaac gacttttcca tctctataaa  18000
taaaaacgaa tacctcatta ttattttctt taactgtatt ctttttagcc aactctaaat  18060
tattcattgg aacactgatt tggacattat aaccataatg aataggttct ttagggctaa  18120
ttataaagga gaatgttgaa attgtactat ttttagttga tgatgtattt tgtggactgg  18180
cagccatatc ttcaggcagt gcgttaattt cagtaattat tccgtctgtt gctttttctt  18240
cattgatttg actaatcgtt acaggttgac ccacttttac tttattataa tcatattctg  18300
tgacagaacc ttttataact gtctctggac tcacaatagt cgcatatggt actgttgcat  18360
ctactttccc tttatcgtta atatagacaa ttcctttgaa tggtgctgtt acggtagtgg  18420
taattttctt ttttgtttgt tcaatagtat tattggcact ggataaatca acattcgccg  18480
```

```
catctaacgc ttgttgtgct tgtaaaactg cctctttttg tgcatctaac gcttgttgta  18540
tagtttcaat tttattatca gcttcagctt tttcggcttt tttcatttca tcatccattt  18600
ttttatttat aatggtggtt tgttcatttt tagcaacagt taagcgattt tctaattctt  18660
gttgtttttg tgttgcatta tctaaattta tttgagcatt tgtaactgct agattcaact  18720
tttctagaga ttgggtttgt tcttccgctt gatcttcaac agttgtattt tgataagtag  18780
caactacatc attttcattg atttcttgac cattcttcac ggaaatagta ttaattttcc  18840
caagggattg atcaaaattt aaataattag ttgttttagg ttgaacaatt ccttttaaaa  18900
ccaagggatc actctttttt accttgataa ttttatagga ttcttcttct tttggttcac  18960
tggcgttcaa cttataaata atggtcgcgc caattaatag aactccaact atacagccta  19020
taatcgttaa agaaatttgt tgttttttag ttaacttttt caatatcatt ctcccctgta  19080
tttactttga ataggtaaac taaaaccata attaccggca gcttgaacac taatgtgaaa  19140
ataatagttg taattccgat aattagtcct atagattgcg tttctgaagt atttgtaaaa  19200
ctaggcgttg ttaacaaaga aaatataatg gacacgacag tccatcccaa atttaaataa  19260
tacggatatt ttagtggaat ctgatctttt tttatctttc tatgtgaaat aaaaaataaa  19320
atcacaaaag caattgaaaa aataacattt aaaactgtga acacttttac tggcatacta  19380
tttaattgat tataaatatc catcccatca gatcctatgc ttgtataaat cttttcgttt  19440
ggatttaatg cactaggcag gccaataatt gaaaaaattg ttccgattga aaccaacact  19500
agagcgatta aattccatat tttaatcttt tttacttctt ttttataatc attcataact  19560
tcaaatcctc tcttgtcata attaaagaat cctatctaaa aaaataaatt ttaactaagc  19620
ttcctaagat ttcataattc atatggtttc ctctagtaga tattgttaca taaataaaat  19680
tatttacata ccccctttgc cgatcagtct ataaaaatca acaaaaagta gtgtaattct  19740
attgtacagc ttcttatttt ttaattttta tttattaatt tatttatcca ttttaagaat  19800
ggggaagaaa aaaatccgag agaaatagct aaaaaaatct ttcctaacat agaatctatc  19860
cctattaaaa atattgcgac tattgttgct aatagtgaga ctataataat aatgtaatca  19920
attcttttca taattttcca agtttactcc cttcagtttg tcaagattaa taatatcatt  19980
tgacaaatat tctacaatat ctttctgatg tgaagaaaat attgttatta tttttttctc  20040
tttgattaag tccatagcta aatatcgact ttttttatct aacattgtaa aaggttcatc  20100
taataataca agagaaacat ctcttgccaa cattaaagaa atgtatagtt tatactccat  20160
acctgtagag taagactcta ctttcttatt ataatagtcc aagtttagac ggctacaata  20220
ttctagtact tttcttttat attctaaata gtctgtttta attccccata attctgctat  20280
tagctttata tgatcaaaaa catcaagata aggatatagc ttagttttat atggtataaa  20340
agctactttt tctttagtta ctttttctgt atacaaagtg ctgtcatatt ctattgttcc  20400
ccctgtgggt tgatatatac ctgataaaat atttaacaat gttgtttttc ctacaccatt  20460
agaaccaact agtgcataac ttttttcaga agaaaattct aaagataacc tgtcaaacac  20520
cataatatct ttggattcat aataaaaact caagttgtta attgttattt ttttcattac  20580
tttactccta ccactaaata aattacagat aaagcaatcc cgaaaattga taatacattc  20640
gcagccctac tgtttacatt cgcaaattta attaataaat tgcgatagat aactactaaa  20700
aaaatattaa tcataaaact cattatactt agcaatcgca aatttaaatt gtaatgtaaa  20760
aatacactaa ataaagctaa atttacgaat aactgaatac tatttacaaa taaagtcgat  20820
```

aagtatactc ttttgaaact gtaaaatttg ttaattaaac taataagaaa tgcaactaaa 20880
caagtcaaaa ttaaagtaac aacaacaaaa gcgggagcac tcataaaaaa aacaagcaca 20940
attatcccta atttagggaa aaaactcaag ttttttcta caaaaataaa ctcttcagca 21000
attagaatat ttgaaaacaa aaaaaatagt gaagtaatac cgatgtattt tttcaaagta 21060
aacttgtaca aacttatctt cctttcttaa gaacttatat ggatcagatt cagtaataca 21120
tgaaacactt tttgtgagag atattttatg caactagagt tgcctatccc aattgacttg 21180
tagacaaata aattatcaca ctgttaatta tatgtttatt gtgaatttca aaaattttaa 21240
gtaaccgaca tattattata aagataattc acgaaaattt ttaccttggt tgtataaatt 21300
taaaatagtg cccactcttc ctttaatgag tatatcttta attcagcatt tttgattcgt 21360
gatcaatggt ttgtttaaat tctttcgtat aacgtttgga aataggcgga tatcttcctt 21420
tgagattagt tttctatctc aacttctatc gtatatctac atagcttata ttagattcta 21480
tatatcctcc aattattatt aaaactattc caagtacagt aaaaaacaca cttaacttta 21540
tgattttttt aataggaact acatgtgtag gcgttttaaa aaaaaccaaa ataacaaata 21600
ttggaatggt acttatcata ctaaatgttg ccaatcctaa aagctctata aaaaaatgtg 21660
gaagaagacc tttatacaaa acatttagtt cattgttaat gtataaatat tgaatcaact 21720
taccaattat ataaccattt atacccataa ataaaaatgc ataaatcccc cctgttacca 21780
ttcctatagt gaggaaataa aaagaaacct ttaaattatt aacactaaca ctataaaatg 21840
aaacttcctg accaaaatag tccaatttat ttatatgagg acctattata atccctgcta 21900
acactcccag aaaaaaaata aatattgata tatagaagga aattttcaaa tatttctcaa 21960
aattaatgat atctaatcgc atgtacaaca aaaattcctt tcctaataat ttttttactg 22020
aaaaacacaa atattattgt tgctaaagag aaatatacta actctccgaa aaatattatt 22080
aatgaataac tttcccctac aattggaaag ataaatgtaa gcactaaagg aacgatatta 22140
aaaaagtatc ttggaactgt ttgaaatttc tctaaaacaa ttttttcatc tttagcactt 22200
ccaatttctg tatcattagt gtaatctagt ttagtagcta aaggaatcat atacatttga 22260
atcataggga aaacatacac agacatagaa aatgttataa acaaaaagat agcaaaaatt 22320
accggaatca taatgtatac agaaactaca atatttatga taattaatat aagtaaagga 22380
attaataaaa ataacctgta tatcgttagt ttcgaattaa aaactttatt caaaccattc 22440
ggagacgatc ttagaagcgt aaattgattc ctttctgatc caaaagatag ataagggtac 22500
atttcttctc ttatttcaaa tgtctgattt ccaattacaa gtatatttaa aagaaataat 22560
agttgtattt gcaacattct attttgtgaa ttcaatagta ttattgaaag cattactcca 22620
atgtaaaaga atgattcata tgtcaaaatt atattttgaa agaaattatt agcaataatc 22680
catcttgtat tagctaactt taacaagctg catttaaaaa aaatattttt ttttaatgct 22740
ttattcaaaa aaaatacata taaattgcat aagtctattt tagtttttgg cagcattttt 22800
gtttttaaag ggtagagttt tggttccata gctaatagta atattgccaa aattaataac 22860
atagccgata ctaaaaaaac atctatataa gtaaatgaat atacatgact ctcataaaat 22920
ttactggcgc tatttacata aaacattcct atatccttag aaaacgactc ccatattact 22980
ttattattta cactttctat gttaacaaaa tattttttta taaaatatac tatgttacta 23040
aatacgaatg atactataaa aaaaccaaaa taagtaaata aagcggctcc aatgctataa 23100
aagattaatc gtgttaatcc aatagcctta actattttat tatagatata ctgtccaaaa 23160
atcctattac tacaataaaa tgaacaaatg tatataaata aaaaaaatac agatagacta 23220 atttttttgaa aaataaaagc attactactt atatatatta aactcaataa tccatatagt 23280
attgaagatg aaaacataaa aatatagaat aagtctgtaa caatcataat aaagcttatc 23340
tttctagaag atattgttgc taattttctt aattcttcaa aaggaaagac gtgcgttcta 23400
taacaatttg atgctccttg aacaattcct aaaataaaaa atattataaa aaataaattt 23460
acatttatat ctgattttat taaagttagt cttaatccca aactaacaac aaatgccaat 23520
gaaaattcaa agaatatatt aataaataaa tagagcttta acgatagttt taagttaaag 23580
taggaaagta ctcttttaac caaactactc tcttgattta ttcttaactt cattagaatt 23640
ccaaagagat tcatgagcgc cccccttttt ttaattaaaa aacagaatat ctctagaaaa 23700
tatcctgttt ttttatcata ttgttaaatt accaagcaat aactgctctt tttccttttt 23760
tcttaatttc tttcttaagg tatgctttaa ttgactctct tcctgctgca gcgagtaagg 23820
aaagacctcc gctacctaca gcagtaagaa ttgatacaat agtagtgacc catccaccag 23880
cttcaactac attaagtaca gttcctgcaa ctgctgctgg tataccgaac tctttagcca 23940
tatgtgcaat cggcaaaaac tgaagacttg cactaaacaa ggctaacccc aaaaaactca 24000
aagccattaa aataaaaatc ttagaaaatt tattttcttt aaccatgata ctcctcctca 24060
aaatattttt gaaatgcatt tcattgctat tatacccatg tagtttattt tgatgcaagc 24120
aataacatat ctatcttgag tttcaatcaa gaaaaaagtc actagatact tcttagcaat 24180
caatatcatg actaattcct tcaaattgtt cattttcatt tgacttatct ttcattctat 24240
cctggttata cgcttgaact acttctttgt tttcttctac gatatctata tcataaagat 24300
aattttcatc aatcatggct tcttgatatt cttccagatt gaacctctca tcttctatct 24360
gtaaggtact ttctaattcc tcaatcttaa aatctaactt ttgtaactga tcgagaacat 24420
ttatttgttt ttcagaatac tgattgttct ttaaaattaa taccatccga ttctctggaa 24480
caacctgaat catttcttcc atcgtcatgg accaaaaatc agggtgataa cggtcaatag 24540
acggatcttt aaaaaacgct tcaattgttc cgtggtcaac atctcgaata cgaccatcgc 24600
caccctcaga ataaccactc cataaagaac catctttaaa aacataaatg gcttgttcta 24660
aattgtctgt tttttcgaat ccttcgtcaa taaaatcaga aaaatcaaat cttgaactcg 24720
tttctttcat cacgttttcc ccatttcttc tttttattat ttggtaaaca aaaagagcat 24780
aacgggtggt tatgctcttt tttttacgtc ttaaattgtt tgagaattat ttatttttaa 24840
atagacatgc tttgttctag ttcctggtaa actttttcat tcaagtatcg ctgcaagctt 24900
ccctgacaag ctttacgtaa atgacgcatc tgtttttctaa attgtacatc cgaatatttc 24960
tgtggatttt gcttaattga cactggtttt tttctcattg tgccacgtcg ttgctcaatt 25020
ttacgatcaa cattgcgaac tttttctggc agttcttctg tttgagaaat atcaaaaatt 25080
tcttttttct caaacgtaaa cgacccatct gcttcttttt ttagagacac aatttctatt 25140
gggttgtctt tttcttcttc ttttacttga cgattattga gttgccattg cttatcgcct 25200
aagagaaacg tcgcttgtgg attggtttgt aagatagctc gttgattgcc atttgaaaac 25260
acatgtaaat tcgtttttat tttcttgttg ttttcgtgta aggtgtgttg ttctgtgtaa 25320
tcactatctg taagaaggat ttcttttgct aatttgtcat gcataaaaat acttgcaggt 25380
tcagaatagg gtgacctttc cacttggcga atatgcatcc cacgtttttc tactttccta 25440
tttatttttg agagcgattc tttatgaaaa tattcttgat tccgtttgtc taatcgttct 25500
ttattttgat ggaaatactg ttgtaagcga tcaattgatt gttccatctt tgtatctatt 25560

```
tgttgttctt ttgatgagcg aatagacgag ctagtgcttg gcacttcttg tggcaacggc  25620
tccaaagata aatcagttgt ttcttccaca gctatttctg gtggaacggt agtatccaag  25680
gaaagaaatt cctctgcagg tttcgtgaac gcatcttctg atggctcagg tcgccagtcc  25740
aagtcacttt ctctaaatcc accagctccc ttcttttttt gacgtagttc tggatgattt  25800
tttgcttcct gtaaaattag attccctatt cttgaataga ggccattctt tccataaagt  25860
ttttgttcaa agtaggtagg ttcatttcga ggattgccgt aagcttcttc gtattcgttg  25920
gatatttttt ctagcttagg aagtatcttt gccattaatt cttgcccatc atattcaaga  25980
aaatgagtaa tcagttggtc tacttcttgt ttaaaatggt gtttctccgc aaagccgtat  26040
ttccagaagt attgattgtc aggcagttta tctagtaatg ccaaaaactt ttcttcataa  26100
ataccttgag agaattgttc cttacaagac tctgccattt ttttctgatg gttaagacat  26160
gtttctagca tcgctaactg ctctttattt tgcattaatt cattgacaaa tactcgctta  26220
gtcgcacgaa tatttttctg taaaaatttc cctttgaatt gccaaccgga tttactaggg  26280
tctttcgggt gtgtgtaatt gatccattct ctggtcggat ttttttctac atacccgaca  26340
tggatatgga tattgtccgt gttgtaatga atggcacctg tccactcccc tttgagacct  26400
tctttctttt ctaattcctc gatcgctaaa cgagtggctt gatacaattg ttctttattt  26460
aggtgattgg ttttttcatc taaatagcga tggtccacta accactcatt gcgaaaactg  26520
aacaccattt gccacaatgg agacttattt ttttgcgcct cctcaaagta gtttttcatt  26580
tcctgaacca catgatttgg tgctttatca tatgcttttg taaaaagcgc cgacgttttt  26640
tctggattag acatataatc gttgtaggtc gcaaacattg tctcgttccc accttcaatg  26700
gcggagacac tatccgactg attggttgga gaaaatgcat taaaggaatc aaagtgttcg  26760
tttctggttg cttcatttct ttccatataa tcaaggtatt cttgatacgt attggaacct  26820
ggcataacaa aggcacttgt taaaatgata ccagccgttt tcttactcat cgtctacgga  26880
ataattagaa tattttttttt gattcatggc cgcaatcatg ctcgcttctc gtttctttgc  26940
caggatttct tttgtttgtg taagggcaaa agagtcctcg ttatctcgca cagaaagttc  27000
cattgttttt gccagggcat tgaataaaat gttggttatt tcgacatgtt cttcaatcac  27060
agataataat tttttatttt gttttgtaag agacaatact tctctgtgcg ttgaatctat  27120
ttcattttca acgatgtcta acatatactc aatgcattct cctaattgat aatgtttttt  27180
tgcggcgaaa gtattcaatc gctctttcgt ttcttccgtc atataaatat tttttggctt  27240
ctttttattc atcgattttt gctcctctct ttgtcatttc taatgcaggt agaaagaact  27300
cacgcaccat caattccatt ccttgatgca tggtttcaat tgcttccatt gtgaaagctt  27360
tataacgtaa ttctgtctct aaatggaact cgtcataagc aatcaagcgc aacatttctc  27420
tgagcatttc gtccctacct gaatagcctt ttttcttagc taccgttact aatcttttgg  27480
caatttcttt atcaatattt ctgatagtta gtgtaattgt ttcatccatt ttatattcac  27540
tactccaatc gttttctact ttattctaag atattcgctt aattgcgcct tgtatttcgg  27600
aagagcataa gggggaatgg ggggcacaca aggtgccccg ccttgcagtg caaggcttcc  27660
cggtgtatta cacatttgac taccactagc ataatactag cacccgctag caggtttcta  27720
gcactcatac tagcacatta ctagcaccca ctagcagagt tttagcaccg actagcacat  27780
tgctagcact ttcgctagca ggtttttagc accagctagc acattactag cacccgctag  27840
cagaatttta gcacccaaac tagcacatta ctagcacccg ctagcaggtt tttagcaccg  27900
gctagcacat tgctagcatc tatttttctt gtttcataag gaaccttttt ttcttttccg  27960
```

```
caagtttttt tagtttttct gccatcaatt tttgttcatt ttttatctct tcactggctt  28020
tgtcgtactt ctcaatctct cgtttcaagc ggtcaacttc agcttgtgtt tcctcttttt  28080
ctttcccaac tttgtattgg atttcctcgg aatattgata aattttgtcg taaattttac  28140
ttagctcttc ttcaatttct ttttgactag tggctaattt tttctgtcta cccttagtct  28200
ctttttcttc ttctgatatg acataaataa gatagttctc tttgggtttt tccgttagtt  28260
tttcatttgt tttactcttt cgaacatccc aataaagtgt ggcttgctgt gaattatttt  28320
tggctgtttc ggcttgtttt tcatccactt ggttcacaga cgtgggtgct tttttctccg  28380
cattgtaccc aaaatcaatc gctaatagtt gccatttttc aggaatgttc gttagctgaa  28440
caaggtaata attttcaatt aatgggacta attttgcctt tactgtttgt tgttttgata  28500
cttcccctgc aaagacaaca tattctttat tgactaaatc ttttccatca tccacatgta  28560
aaaagatttc ggcataccct gtttttttcat tcacttctcg tgagagaaca gtgacttcac  28620
tagagccaat ttttgtgaca tttgcttgcc ctatcccact gtccttaagt ggactatcat  28680
cttcaaaaaa gtttcgggag aaagcaaaaa aacagtaccc aaccatcgtc aaaagcccta  28740
taaaaagata aagttttgac gaataatttt gccatctttt tttccatttg ttgctctttt  28800
tctcccctga ttgcacacga tctcgaaaat tttcaatccg ttcttttata gtgtttatct  28860
tctcgttcat gggcttcact ccggcataaa ataattattt ggtaggtctc taggggcaac  28920
ttgttccgta aaatctttga ttttccagtg gttattcttg tctttttcca atttgaatcg  28980
atcaatgtat ttcacatcaa acggagcacc attgccatgt tttgtggtga caaggataca  29040
accaatcatg accgcttttc ctgtgacgcc atttagcttc acgtaatatt gttcacttgc  29100
tgtttcttgg tcaattcgaa aatctgtttt gtaatcattc acccatgcgg ggcgaagttt  29160
ttttgataag ttaggcgtga caatctcttt taaagtagct aatttctttt ctgctgtgtc  29220
cgtatttatg tcataatagc cagcacgaaa ttgttcccca atcgctttca aatttttcata  29280
ttcttggtga gaataggaat gtttttcaat cggaatttct ttagaaggct gccctacttt  29340
ttgctttttc agttcttcca gttctttttc taattgggtt gtttttttctt gtgattgttg  29400
gacttgttca gcctgttttg gcaataatac tttttgtgca tatgtgacgg taccacctac  29460
gcccaagact aacccacaac agcctgtcac aagatatttt tgtatcattt tcaacagttt  29520
ttcctcctaa aattatttat ttttccgaac aatgcttcgg atttttgtaa tgtcataggt  29580
acgattgtat tttgcgacaa attccccttt ttcgccattt tgctcataag tagagaagtc  29640
ttgtccgcca ttagaaacac tacttataat gcccgtatgg ccataaattt gaggagttag  29700
aataccaccg gcataccaat ttactacgtc accaggttgt aattcagacg gtttcggctc  29760
gataatcacg gtccaaccaa aggccgacca gttataatca tcccctattt ttttctgcaaa  29820
ttctttgcca ctatttttca actttgggcc ccctaatttg tctacataat aggccgttaa  29880
aaagtaacat tggccattat caatctgagt attaacgacc gcttctaata gttgaacatt  29940
tcccccattg ccttgattta taccttgttg catcgtcgca acatattggt aaatcaattc  30000
cgcatagaac atatttccat ataaaaagcg ccagttccct cttgaattgg caatcggatt  30060
ggtgtagatt gttttagctc cgcctgcttg ctgactagca aattctgcgc ctgcttcaaa  30120
cgaatagggt cgatttttag cgtgcagcca ccctaaaaac ccgcctccgt aattgtaggc  30180
ctgtaatacc gccttatggt cttgaatgcc atattgtttg gctaaatcta aacaactttt  30240
ataatgggtc accccttgac gtatggattg ttccgggtca tttattgtat ttggtgctaa  30300
```

```
ccctgcactt tcactggatt gaaacggatc gcccccacgt cccccggatt ccaccatgat  30360
aatggccaat aaataaggga cttcatccgg aatccccagt tctttggcca ctcgttcaac  30420
gattggtttt aacgccatta cttcaggtgg gagccctata ttttcagcgg gagataagtt  30480
ggttttctct tgcgtttctt ctccaacaat agccaataac gttcgttgtg cttcttggac  30540
aatcgccaga caaacaagtc caatggagaa caccgttact agaaaaaggc caattttcca  30600
tttccatgcg tttttcatac tgatacctct tgttgtcgtt gggtttgttg ttctttcgtc  30660
cacaacgcct gggcttttgt ctgttctttt tgttttactt gccgactaac taatttgcct  30720
gtttttgtt tttccaagca ttcattccag tctccttgtt ccattggcgg taaccgtaaa  30780
gaaagatttg ctgtttcttt caacgtttct gactggcaat aggtttggtg tacttgcttt  30840
acaaaatctc ttccaggtaa atcgttatta accgctaaaa caatttctcc ttcttctgtc  30900
cctaatacag cagataaatc atggtaggtt tgccaaaggg tctcttcttt tagaccagac  30960
aatgaaagaa accatgtatt ggcaggtaga ttgtcttttt ctaactcata caacgacaaa  31020
gattcaatcg gtgcttctgt cacaaacaac gtcataggcg agcgaaaatc tacatttttt  31080
ccaaataaaa aaccacgatt tccgtggctg ttttctgcaa ttcctttaaa gtattttcgt  31140
ttcaattcca tcgtgccatc ggcagttgtt ttgattcttt tggctaaagg aatcgcataa  31200
gtaccttgaa tatctgcacc cacggggatc cctagctgcc ctttggcaat ttcagagaat  31260
ttaaacagaa tgttatggcg gttgtctgaa ctaacgagtt ttttatcgac aaactcttga  31320
atcgtttctt cggataaatg acgggatttt aagtagtccc ttccctgggc atcaaaggta  31380
cctgtatcgt aattgcccgc cttagacagt ttttctaacg taaaaggcgt tggcttttgg  31440
ataggtttag aaaaacgacg ttcttgatta gtggtcttgg tgcgttgttg tgaaaactga  31500
tactctaaca actctgttac gacctgttca tacggttctt ggtaaaagat catcacaaat  31560
tctatcgcat tattatagga atttattccc tgagaatacc aattcaccac gcctgttttt  31620
acattggctc gtagactatc atgcagcgta tgttgcataa attttgacga cactttttcg  31680
aaagtctctc ctcttgcttg taaatactcg tacatattgg tacgtctggc gacggctatt  31740
tgtttctttg aaaaaacagg aatttttggc atttatctgc acctcccaac ctatgaactg  31800
agaaacgata acagaagata aagaaaaaag accgctacta ccactaggta gagccgcctt  31860
gttcgaacac cttccttttt ttctgtgcca ccaaagatca ttcgtttcca attcctctgt  31920
atcttttgtc gtattgtttg ttttttaact ggtttgtctt gtttttccat ctttacaagc  31980
ctccatcaaa gattttcttt tctgtatcag ataagccata acgaaacttg atattctttg  32040
cccctttaat gtttaacaaa atgtctcgtt cttcaaagcc aataatatct gcaatatcat  32100
aggggcttaa ctgattccca aaaactttgc gtaacaactc ttccgacgat tcatcttgtt  32160
tgaataaaaa acgataggtg gtgagtttaa agagattgac cacgatttga gaaatttccc  32220
ccatcacccc attgttgtaa tctgggaacg catccgcaat atcatgaaag atataggttt  32280
gccctattag tagctttcgc ccttcccgat tgtagcggtc aagagctttt aataattctt  32340
tgttttgtgt acgaatcgga ttatgaaact cgtctgaagt aatattggag taaatcaact  32400
cgtccactcg tttctgccta cggtcaaaga gatacttttc gcgttgtccc actcgaacag  32460
cttcactgaa tgccgccgta tagagattat aatattgcgc attgtacgtg gatatatctg  32520
atttcactaa gttttccata ttgaacgtga ccagtttttt gtcaaaaaaa tcaaaagtag  32580
acttttgatt aaaaatagta ccagattctg tgataaacga ttctagctta tttatcaatt  32640
catacattga ttgttttgca aacgattctt tgagtttgtt gtattcttgt ttcgcatagt  32700
```

ctaaaatatc ggaataaaca gggtactgtt ctgccgcata ttgggttatt ttactttctt 32760
ctaagccgtg agaagccata tacgctcggt atccatcatt aaacactcgc ttggccgtcg 32820
tcattagtgg gctatcaaag gcaatgtttt cagctaaacc aaaaactaac cgcattttta 32880
ccagatttgt ttttaacgac tgggcttctt tggtcttttt tgtggcggca tctatatcgg 32940
aacgatagat ttgacaagga tttaagcgaa cttctcctgc gtcaaaatat tcgcctccta 33000
aagcttccgt taaacgtttg gtttcgtcac tgacataaaa tccatagtga atattattgt 33060
attcgattgc ttgttttaat tgtttttttgg ccgctgttgt tttcccaaac ccttgggcac 33120
cgataatgat actactatag gatttccgca agctatcttt atgtgtggtt gataaacaaa 33180
ctacgccaga accgtacagg ggaaagccac tatatggcgc atctgaatca atgtgattgg 33240
aataattaaa cgcatagctt cctgctaggg ctgttccttt tatttctttg ccttttcgtt 33300
taatcagtcg tccaccgtct ttaaaactga taaacgaggc tttaaattgt cgctcctgtt 33360
cgtctaagaa acaagcagct tggaattgat tttttcgtaa ttttcgatgg acttcttgtt 33420
ctctttcgtc taatgcttca atcgtaggct cacttaatac atatcggaca tgaatttctt 33480
ttaaaacgtc tgtcgcttct aaaatattct ctaccgtaga atccaatttt tcatactctt 33540
tgcgggcttt ttttcttgag atacggtctt ttgatgaata gactcggtct tcgtattccc 33600
ctaagctttt atttaagctt tgttcgacta atgggttggt tacatcgatg gtatggacag 33660
atacagtaga caacacatgt ttcatacaaa acacttgttc accccaaaaa tttgggttgt 33720
tctttgggcg ataaatggtt aaattcaacg ttcgaatata gccattgttt atttgtaact 33780
ctctcgaaga atgcgggcga atcccgccca tcggttgaat actgccgata aataacgggt 33840
cataaccttt tttctccacc attttttgtg ctttttctgg tctgccttgt tggtctgttc 33900
catgataagg aacccctgtt ggtaacggtg ccagcggatt gtagcgacgg aataaaaact 33960 tgatttttttg tgtgagtgtc atggtattaa tgcgaaaatc agcactttgt gcttggcgaa 34020
tttctcttcc tacttctagt agttcttctt catcggctgc aaacacttgt aaatagactg 34080
tatcaatcag tcgtgtgtta tctaggtttt ctaaaacagc taaggtgtgc cgttgctctt 34140
cccgtaccat cggacttaat gcacccattt taaaccgtcg ggttgcatac tcaatgtttt 34200
cagacatatc aagcggaaaa cttgtaaaaa taaatgtaat atctgagtga atggtcttta 34260
gaaaggttag aaaatcatcg atcgcagcct gcctctgctg aaggcttcct tctctggcgg 34320
aagaatcttc tattcggtaa aagttcgtca cgcctttttc tagggcaata cagtcctctg 34380
aaataattct tcgttcagcg acaaatgaca agactgattt ttcgaccttt ttaatcttgg 34440
gtttcttttt ttcttccgta gtatccacca atttcagtgg ttcttctaag agttcatcgg 34500
tattgatcac ttctttttca cttccttata caacaaaaac ccatcagcgt cgttcttcta 34560
ctgatgggtt tcctttttat tattattcaa tttgtgccat ttttttcgcc acttccaacg 34620
aagataatcg acgatttgtc tgcgctgtgt ggctttttta taatcgtgtt gcaaaaaacg 34680
taaggtttca aaaaaatgag ccattcctgg ttgttgccaa ttttctttcg ttagaaattg 34740
gccacgagta cgctttcttt gttgccctgg tcgacgatac acattcagaa tataggcaat 34800
ggtcataggg ggctcacttt ttttgcgata aggtttggta gggacattaa ttaagccacc 34860
cttcagtaat gccttccaat tatccggatg ttcattaata tacaaccgca ttggctcttg 34920
caagtctttt ggcaactgca ggcgctcctt ttccccatcc aaacgttcca catgaacata 34980
gacaaacaat ggtgtttctt cttgtgattc cataggaaca ctcaaaatgg taggtcgtcg 35040

```
tctgaaattt caatcggact gtttccttgc tcaaacgggt ccaatggatc aggtttatct  35100
gttggttgct tgtcaaaggt tgcttgtcct gcacctgtag attgtcctct gcgctgttcg  35160
tttacttctt ttgattctaa caattgaaag ttttctatga ctacttccgt cacatagacc  35220
cgttggcctt gttggttttc atagttccgt gtttgaatcc gtcctgtaag accaatgagt  35280
gtgccttttc tggcataatt ggcaagagat tccgctgctt ttcgccaaat aacacaattg  35340
ataaagtcgg cttcacggtc accattttga ttggtaaagt ttcgattgac agccaatata  35400
aactgtccga ctgccgtgcc actcttggta tatcgcaaat caacatcttt ggttaatcgt  35460
ccgactaaag tcaaattatt aatcattttt tcttcccttc cctcattgtc cttttcttcg  35520
ctcgttcagc aatcggttgg tcttgtaccc taagacctat ttctagttca cccattcttt  35580
tttgtacact atctctataa ttttctgttc gatttattat ttttttcatg gtttgtccct  35640
cgttcatttt ttttaggaag gtggtgatag tctaaccaat acgacagggt acacaaaaga  35700
aacgcccccc atccaaaaag agttagtttc ctttcatcat ctccgggggt gttaatccac  35760
tcaatacaaa aaaatagccc catgtataag aatcctaaga taccaattat ccttcccact  35820
ttttttaatc gcttcgcatt tttttcggta ataacagaaa agaagcataa actacgttgg  35880
agtaacaata aaaaagtggc taaaaaaatc aagaatagca tccattctac agcaaatagc  35940
ttccatcgat gttcaaaacc agcaacaaac atagtaaaca ctaaaaaacc aaggcaaagg  36000
ccagcaaata aagtcaaaag aacagtcaga cacttttcaa taaattggaa cagtcgatta  36060
tctatggtac attcactcct ttagtaagca agagtatcat tatttggttt ctttttcttg  36120
ctcttcctgc ctttttactt ccttaattga agagcgaatt agcattggta tagcgactat  36180
agctaataaa atcccggtcc accaaataat cgaatgcatt cgcatttgtc gaccaacatt  36240
taatagttgc ataaacagaa gaattgcaat ccaaaaattt aattgtttcc ccattttctt  36300
gagcatacgc ctatttatcc tctccattta ccgtttgcca gtacttaatt tggtctggct  36360
taaatcctga ccaatattct aattcctctt ctgtttcatc atcaatgatt tttattagtg  36420
gtaggctttg tataccatat tttgctttta ttttttctac tttttctcg ctccatgtcc  36480
gtttctgttc attgatacta ttgacttcaa ttgaatttgt ttcctctgaa ttcccataat  36540
acgtattttc atagggcaag cctacttcgt ccattacttt ggtgctcatt ttacactgca  36600
cacagtgggg ttttgtatat aaaactgcat gtactttatt aaccatcttc taattcctca  36660
actatcttat ttttagtttg tttgttgtta ttatatcaaa ccaagagaga gtttcacatt  36720
atttcatccg tcattgcttg gtcttcttcg gctaattccg attctgttgc catcaccatc  36780
gacaattctt cttcatcact aaaagacact tgggcaattg ggtgatacgt ttgccgattg  36840
ttggttaata caatccataa ccgctgataa tttcgcaacc gatagttgcc aatactgggt  36900
gctaaccaaa aaagcccaaa taaaatgaca aacaaaaaag catatgtccc taatgggcca  36960
tacgtttttt cctgtaaccc agtagccatt tgaaacaaaa taaatccaca gacagcgtct  37020
tttgttaaga ttttcccata aaactttgct tgtgtaaaaa tttcttcctg tatttcatgc  37080
atacgttcta cctatgctta gcctttctta tttttttgtc gtttatcttt tggtacttgt  37140
tgctgttttt gctttttttcg ttgttttagc cactcgttca cgtcttggcc aaattctttg  37200
tttcgtttgt atcggtctac ttgattgcca attggatttt tttgattctt ctggtgttta  37260
ttggtgttta tcatgttgtt tagtttcttc ttgaacggat tttccactga ttctgtcgga  37320
gattgctccg ttggtgaagc ttgttctcca cttgatacat ggtgttcttc ttgctgttcc  37380
gcttgacttt gctgttcaac tgcctctgta tttttaccag tagctaacga ttctggttct  37440
```

tggttctctc cagctgtgtg gttgttatct ttcggctgct ctagttggct agtctcttca 37500
tctgcttgat ttttctctgt ttctgtcggc aagtctatag tatgttgctc tttctttgtt 37560
ccatcccctt caacgctaga ttctgtgctc tcagaagcat cgttttgatt tttctcttga 37620
cttatttgcg gatcgttggg ctcttctaaa tcttttccac cagtaatggt cgtttcttct 37680
ggtacttcct gattttgctc cttttgttgc ttatctggct tgttatgttc ggtttctttt 37740
ccttcgtttc cttgtaattc attattcagt tcttccgcat tcgttgggtc attgtcccgg 37800
ttgtttagct gatttaagtt ggcgttttca tcgtttttcg tatcggaccc tcgtaaacca 37860
tccgcaaatc ctgctaaagc aactgttcca ctagttcccg caccagctgc tgttttcaca 37920
acactactca ttttatcaat cgctgttttt gcacccatgc ccattacaaa tgagcctgcc 37980
gttgataaac cggcatcaat acctagtgtc ttttgaataa tggatggccc atcgtaaata 38040
aaccaggcgc caccgattac cgcaaagagt ttggctaaca tggaagattg ttgtgcaaaa 38100
acaaacgcat tgtatttaat aaatacgtag tacatggaat aaatagatag aatcattacg 38160
aaccctccaa caatctccat taagaccgtc ttcgctcgtt tcgtatctcg aaagctaaaa 38220
aaaatcacaa gatttgccca aagattatta aacgcaagtt caatacccaa ccggccaact 38280
cgaacaagag aaataagcat ggagagggct aaaaccgata gagtgataat caatggcaac 38340
caattcactc gccagcgata atatttaggg gcaaacgtgg acttgattaa ccacccaaga 38400
acaccgcccc cgccttcatc aagctcctca acctctttcc cttcttcgct tttcttattg 38460
actagtttat atttgaggac ttccccattt ttgacatcgt cagggtcagt aatccgttca 38520
ttaatatcaa agcctttcct gtctgttaga ttgtttttta tttttggatc tgtggttttc 38580
cactcgccat ccgctagcaa ataaatatcc gttaagtttt ctttgaatgt tgaaaaccca 38640
atgctttctt gtttggtatc caaatctcca accgtcgcat tgatgatttt caacccatct 38700
cgcatgatat tgggtaacat taaggacatt aggagtaata acaagacatt cattggaatg 38760
tctcttgtct gattcgattt tcctaatatc aataccaatc cgacagcaag tattgctaga 38820
cctacgccaa aggctttaaa actgattaat gtgtctagca gactgccttt tccttgcata 38880
gaattgtcat tgtaaaagcc taaaaagtcc aacattgcac tcatcacacc cgttaagcca 38940
tcgacaatcc atagcaagaa agaaaccaga aggtctagta ccctccgacc tgcatctcgc 39000
ataaaatcag cgatgtgtaa ataatccgag aacatctcta aaatcttaag aatttcttcc 39060
gtcttcatcc agtcgcctcc agtccttcag ttgttggatc accacattta ctgcactttc 39120
gctgaaattt gataaaagac agctaaaata cgaaagcaat gtgcctgctt ctgcgatttt 39180
ttcgagttct gaaaacgtct gtgtgtcctt ttttccaacc atttttatgt ttgaaaacaa 39240
cacttgccgt tgcttttctg tcaagatttc ctttaccggt cgttctaact gcttgtgata 39300
cagctgttct aatatctttg cttgtttttg atattttttc gttgaaagtt gtgtttgttc 39360
ttctttcaat gctgctactt cttcaggcgt ggccactttg gtttcttgaa cccgtaccgc 39420 tggtttttttg taattaggaa tcggtggcac aaactctttc ggtcgctgtt gactactgtc 39480
tggttctaat agccaattca attcctctaa ttctacttcc ataaattgat tattcacagg 39540
gacttcttcc catgagactt tttccatttt ccgatactca taaaaaggaa tcaagtgggt 39600
atcattttca tacgtattaa gaataggta ttgataaatc ggatttcctt ctaagtcccg 39660
gtgtttatta attctcaaaa tgaccgattc cccttcacgt aagcgttcca attcgtacga 39720
tgccaataaa tcaatccgtt cagaactctc tgtttccgtt gacttcacag acaagggatc 39780

```
tttgtggcgt gtttttgagt aattggaccg ttcacctaat cgtccagcga tatatttatt  39840
ggttttatcc gagcctgtcc gaatataggc aagattcccc gtactcccta gaataatgtc  39900
tttggtatct tcatcatata acgacgaaag ctgttgaata tcttgtaaga ctaagtgtga  39960
aaacaagtga cgacttaacc ccgcggtcca tttacgagct aaatcgttga tggctacgcc  40020
tagatttcca ccttcttcat aaataaaatg cacatctcgg taacattgtg attcatcttc  40080
taagttacaa cgattgatca acacctggta aatctgttcc aaatacatca cacctagctg  40140
attgtttgag gtatccgcat cacttaaaac aataaacaca gctgtaggct gctctctgtc  40200
aaagccgatt ttttccatat caaagccatc atcaatggcc gtcattttag cgttcaatga  40260
cataagaaaa ggttgcaagt ccccgtcaaa gtgggtaatg atgtttccta aggtgacatg  40320
tgcaggcgct gaggccataa tcgcatcata aaaacgtttc gcagggtgtg ttcttggcaa  40380
ttccccgaaa aagacgtcca attcactctt tccatcatat tccgctaata accgttgcac  40440
ttcgtcaggc tcttctacat agcgtttcaa aaattcgtgt gagccttctt tgattcgtcg  40500
tttctgcatt tcattcacta ccgtataaat cgtgtacgga ttgactttgc tggtttcttc  40560
ttcctcatat tcttggtcag ctaatgccat acccacactc acaaatagat tccgacaggc  40620
ttttgtccag aatccaccgt ctttcccttc gttcacttcc cgaaaatacg aatgcgcaca  40680
ctgcgtaata attttttccg cattggctaa ctgtttttct gcttgaatac tgcaatttaa  40740
cgcttcactt ttcttcccag ccacttttaa gtcggcactt tcttgtttta agcgtttgta  40800
atgacgataa tagttgttga acacgcctag taccggaatt gggtcggaat agtattggtt  40860
gacagtattg acgacacgta tatgataccc acgacgtttt agggttttat accacttccg  40920
tggctcgtcg cctttggttg cggtcatgac aaaagacgca cgatttttca ttaatcgagc  40980
tctcgttaga atatcaataa acgggtccac aaagtagatt cctttccctt gtcgggttcc  41040
ggctaaagta atcgtatttg aatcagttgt atctacataa taagaaaata taccagcttc  41100
tttttctgca gctgtttgtg gtttcttgcc gattgggtag cctggttttc catcaaaata  41160
atcttctgtt tctgtaaaag agtgaacagc tgccaaggtg tactgtttgt ctaattcagt  41220
tgtttttttca aaatccatcg tcccttgtac atgttcttct tccaatgaac gaaacgaagt  41280
atataggcga taagcaagaa cactgaccga aacaaaacaa gccaaagcta agagaaaata  41340
aacaaatgga aattgcccca acgggtaaaa aaataaggtg tctttaaaag acacccattg  41400
tacatcaaat agtgagccgc tcgttaacga tagaaaattt tggattaccc aattgccaag  41460
catgaattct atcaagaagg tcaaactcat gcttgggagt aaaaatcgtt gatctgctaa  41520
aaaacgaaga ctattttgtt tggctttttc ataattttc tttttggttt tactactttc  41580
ttttttgcgc aacatcattc caccactctt tccatggctt ttctttgaaa aattgtcgaa  41640
cataaggaat ctccactaaa agacaaagaa tggccggcat tagtggaact gtgtatcgta  41700
gattttcttc taagaatgag gagtaggtaa aaacaagcac ggtgaacaca ctaaaaatca  41760
aaaagaaaaa gtggacaacc attgacattg cttctttatg aaatagcata cacccgcacg  41820
tccccactaa ataaaccaat aaaaaggcac tcaaaaaact attcactccc agccactcct  41880
ttcatgttcg ttactggtat ttcgtagtct atccttctcg gaacaatctc ttctaagtga  41940
atggataaag taaatggcgt atagcggaaa cggaacaaaa gttgcactga cgggattgta  42000
tacgctgtgt gccactttcc tttcactaac tcttccgtcg ttttacggca acgtttgttt  42060
tcttcacccg ctaaaacaac atagggttgc caatctccat ggattagcca ttcgttggct  42120
gtatacgctg ttttagatgg atataacgga aatatcccct gtttcaattg ttcgtcttta  42180
```

atcgaattaa atcggcgaat caacaagtat tgaaccagca tgatcaccaa tagcgagaaa 42240
tcctcgctat tggcggtctc gctaatccca attcctacga gtaaagcaat caagcctaac 42300
gaaccataat atcgactgat tcgttgaaca attcttttaa ccgttgccca ctcatcttgt 42360
gtttttagga catagtccat tactgcctgt aggataaaaa cgaggaataa aattggcacc 42420
aagttgtcat acgttgcccc aaaaggactc acttcagaca atcgtccctg gccatttttt 42480
gtggcgacat agactgtgtt cccaagtaac tgccatcctt tggtggctac ataaaaaaca 42540
ctcaacgccc atatgcccca cgaaaggaat cccatgattt tgcgtaggat caagaagcag 42600
tattctattc gtatcctttt tttcattctt tttcgcacca cccttctaag gttgcctttt 42660
ctctaggtga attttcacct aacccctgtt caacctttgg attacggccg ataccaaaaa 42720
ggaatatatt cttattttct tttgacccta tataaaaagg attcgggttc aaatctacct 42780
tttgaaaatt atgtttactt ttcttgattg gtaataggtg tctccaccat tttattcgtt 42840
ggttcatcta ttttcacttc cgtttcttct ttttgtgcag ttgtacctat cgttgaatca 42900
gagactgtct ctggttcttt tggttggtct ttgattggtt gtggtaagtg agtaaagtct 42960
ttttgtacgt ctgcaacggc ttgattttgc gtagttgcga tttccttcac ttcttttgcg 43020
gtatcttgta cctcacttaa tgtttcttgt gtttcttggc tctttgcgac aaccaattgt 43080
tgtgcaattt tttcttgatt gttttgtaca gcaacagcgg ctgcttctgc ttgtgcaact 43140
tctgtttgaa cattgacagc cacttctgta ttggtttgca cttcatcaat tgctgtacca 43200
accgtttctt ttgcctgttc tgcttgaggt tgcactgttt cttcgtagtt attttctagg 43260
ttttccaagt tttcatgcgt ttttgttgca ttagaaactt tgttttcaaa atcatttgtt 43320
gcctggttcg ctttttcttg ggcgttgtga acttcgacaa ctttttcttg tagttgttgg 43380
tatgtttggt tatacaaagt tgcattaatc tcttctacct cattgttctc acttactaag 43440
gttttaattt gttcagataa ctgattatat tcatcgacta aatgcactac ttctgaccaa 43500
taatttgttg tttcttcccc attcttactt aattcttcca cttgagtaag ttgcgctaac 43560
tttttctgca cgttttctag ttgatgatta atgttttgtg ctttttgtgt ggccgctact 43620
agttgacctt gtgatttttt aatcaattct gaaaccgttg gttttgttgg ttgttcgggt 43680
tcaactggtt gatctggttt tgatggttgc tctggaactt ctggtattac cggtaaattt 43740
ggctcattag gtactagcgg tttatccgga atcactggtt tttctggtaa aagtatttta 43800
tcggttgtat ctgttttccc tggtaatttt tccattggtt cacttggcgt tttctcatta 43860
gctaacgcaa gaattgtctc ccgctgtttt tctttttttgt tcgtttctcg aatcgcttcc 43920
ttacggtcct gttgaacaag cgcattcgct agttgtccta atagatcgct ttttatttct 43980
ggtatttcca caccaaagag ttttggtttt tcttcttttg tacgttcaaa accgctaact 44040
acttcagcta acgaatcttt cgtttgttga gactgcttac ttttttttgtc tttatccttg 44100
tttttttctt cattttccgt cactttccgt tcccaagggg actgtttact ttttgacgtt 44160
tgacgttctt ctttaggttt tggaccttgt tgctctgtct gtgcgtcctt cttttcgccc 44220
tggttgaatg cagcataagt cagcccgctt cctagtaatg cgacagaaca taacccaatt 44280
actaaatatt tttggtgttt tttagcggtt tctttttgat ttccgttcat ttctttcatt 44340
cctctcaatt gttgtgtaca aaaaaggagc tattcttttt agaacagccc tttttttgct 44400
tttttattta ctttctcgtt cgttatacgt ataatagaat atgaaaagag gacatgctcg 44460
aaacatgtcc ccttagagta aatgaccgat agaagatcgg cagcatatat tttgacgata 44520

```
caaaaaaaga ccgccgtaaa cccgctaaag tctaccgacg gtcttttttg ttgtcgtctt  44580
ttttgcctaa tttatagact tgtattaata gtgtaagtaa ggccaacact tctaatacag  44640
acacaactgc acaactcctt tgccagtttt tctgatttac tatgagtact ctcataggca  44700
ccagctcctt tgcggtggat ttatgctgcc gtcttcaact tccatttact ctctgtgatc  44760
ataccatatt tttactcttt tttatataat ctgtaaaagt agtcagtcgt ttgttgttcc  44820
aaatgctcta gttgatcttt tacttctgtt agctttcgat taatgtctct atactctttt  44880
tgtagatctt tatggtctct ttgtaggtct ctataatttt ggtgcccaaa cacaataagt  44940
atgagcgtaa aaagagttat gagtatcaac ataaaaatac ccagttgtaa cccattaatt  45000
gtcgtaagtt tattcataat ttgatttttc cctccgaatt aatgagcaga ctttccaatt  45060
tgttccaagt ttttcagcca tagctggtaa ttatcggcag cttcttttcg ctcttttttcc  45120
gataactctt tattttcctt atctttggcg tatttttcta acaagttatg aatacttttg  45180
gctactttaa ttgcttcgtc taattcatta tccttcagtc tttcgtttat tctctccgct  45240
tcaggtattt ttcgctctct aagaagttta taggcctgtt cgatttcttt acttttgatt  45300
tgttttgtta acgtaacgtt ttgaatttct ttattaataa gctttgcttc ttctatctta  45360
ccttgttcta aaaaagcata gcctaccatt gcctgaacgt cactctcctg tggtaacttg  45420
gaaagttctg ttgctttctg ccaatctttc tctaaaaacg caagatatag ctgagctaac  45480
tgtgtattag aatgttcagc tattattttc aaaccagctt tatcttcttt ttgaaacaac  45540
tcctcaatta gctctggttc tttctcagga tattttttta ctatttcagc gtacttttct  45600
ttattgacta actgctgata cgtaggctct gaactagttt tggccgtcga ttgacttccc  45660
gccataaatt tccaaccaat cacaattaag agtattccta tagcaaatac tcccaaaatt  45720
ttcagttgct tttgagaaag ttttattgga aagactactt gctttttcct tttaggattc  45780
cccacttttt ttgccttttt tatttttttc tctttttttga aaaagcctat ttccttctct  45840
ttgccagatc gagccttggc ttcctgtgga ttcttgaaag agagtttata gaacaaattt  45900
tcggcttgtt ctgcggtcat tttcttttgt ttgattagtt gattcagctt tttttgtatg  45960
tctctttcca acgtccatcc ttcagaaagt ttagtaaagg tgcctcgata aaagggatct  46020
ccattgactt ctaatagttg aaaagttact gtctcatcga tttccatgta ttgggtaatc  46080
tcaagaaaat ctaaaaatgg aagtaattcc aacgatggtt gtttagcgag aacctcgacg  46140
ttggaagaaa ggatttccac ttcgacagcc attttttatc ctccaatcca accccatact  46200
gtgtctttga tccatgtgaa gttaacgatt attgcggcac caataaaggc tccaaagacc  46260
catttctttg cccactgtgc tacatccatt cccaagaagc gtgcgccgcc ataaatcaat  46320
accgcaattc ctagtgcagg attggcaaac tttcgtagtt gatcgccaaa tccttcttct  46380
acacctctta ccgtactttc tacatctgct agtactggca tactcgtata gacttcaatt  46440
agtcctaatg cgacaatcaa ttgaaagact ccaagtgcgt attttacttt cttttctaca  46500
aaatttttca taaatagttt tcctccaaac agttttttat tgattgtgat tcccttgttt  46560
ttttcgttcc aattctttgg ctaataaacg gtcaatgatc tctgattttt ctaaaagata  46620
gttctggtgt tgctcattta gccattcttc ataggaagta ccatttaact tcattaaagc  46680
ttgtaccctt tttttggttg tgctatcaat tttagttgcc atacttgttc ctcctaaata  46740
attatttgtc gttcttttgg cgctacaagt tcaaacggaa tttctaattg tgctaagcgt  46800
tcacgctctc ttggaaaata tcttacggct actttttga tatatttctt cttaaatcca  46860
tagttttcgt aaatataacc aaaagaatca attgtttcgt tataacgctc cactggttta  46920
```

```
acggctatat aataatcaaa ataaaacaag cacgtgatag gcgtttccac actgacctca  46980
atttcactac ttagcgtcca taatagcgct ttttctgttt cagcaccttc ttgtgtctta  47040
tggcttttca cccatgcctg tcggcttttt aaccattgat aaccacgttt gcgtaacgct  47100
gctttgatag aaaaaccatt ctcaacaacg gtacaataaa gcgttccttg tgattcttct  47160
acccagctgt ccaagtcacc gtatagagcg atttcttctt ctaagaaacc tgtattcacc  47220
atgatttctt gctctttggg actcactttt ccttgtttta ttagttctgt taacaattct  47280
tttactattt tttccttggc ttcttcttcc tcaaattgtt cacgagtcac aacaatcaca  47340
tgtgtagcta ataaacgaag gagtgtcaat aaaatctccg ctggttcccg caaaagattg  47400
ctaacttcta ttacccgctc tacttctaaa taattcccaa tggttcgctt gcgctctttt  47460
ggaagtatac ggatataaaa atgcttatac gcttctgcgt tgagatacgt ctgatccaac  47520
agctgacaca accacttttt tatgtcttgt tcccgtacat tcattaagca tcaccgtctt  47580
tctctccttt ggcgttcttc ttcgaacaat tcttcaatga ttgttgcacc ctctttggtc  47640
gaatttttgc tcacttctgt aaaacgcatt aaaaacgcca tggcctcatc atgtgttgct  47700
ttgggaaacc gataaaaata ctctcgttgt aaatacgccc aaaattcgtc actgctcaca  47760
ctttttgaca tatccttcac tcccctgcct gtttttctgt tcgtttcgca gttctttctc  47820
tgataaaaaa taatcatgat aggcttctcg cttaattcgt gtttcaatgt aaaacattgg  47880
gacttcaaaa gtagagtttt gttcgaatcc aaacttgctt ctttcggtat ccactttcag  47940
cgttaatgtt tttccgttct ttagtaagtg gataacatcg atctcatgaa tattttcagg  48000
tgttacttgg ttatttgtta ataattcaaa ggtttttcct tttttaacct taatcatcaa  48060
taggcgacca cgaaatcctt gccaacgagt attgacttct ttttcctgaa tagctaactc  48120
tttcattgcg acacttcctg ttcgttcttt tatttttttcc atcattgtcc tttccaacaa  48180
aaaaagagaa gcacgcattt ggcttctctt tacctgtctt cattccttca ttatttttct  48240
gtttcttttc gtttcaatcc aaaccatgcc agtcctgcaa gcattcctgc ccctagtaca  48300
gaaagtaacg tattttcttt ctcgccagta tgcggcaatt ctggcaccac acttgccttt  48360
tctaccacta atggctctac tggtgcttgc ggtgtttttg gtgttggtgg tacaatcact  48420
gtttttttctg gtggcgtttg tggtttttct ggcgtatgtg tcactaccgt attcgtttta  48480
atcttctcat tgttgaaaga ttcttcgatt gtgttgtaaa cgtctcctgc cgcaattcgt  48540
tctacaccaa tgaacgcttt ccatgagtgt gcaacgtttt tgttttcttt tagattcatc  48600
gcatctaaaa aggcttgact ggccgtgatt ttcactaccc ctttgtcaaa ggtcatcgtg  48660
aatagtttcg aaatgtcatc ccctttattc actttggttc cgtctgctaa gacaaaatta  48720
gaattggcaa acacagacca ttggccacta aatttgtcat gtttgacgtc tagtttgtca  48780
ctaagcgacc attcttccac aacaccagcg tattctgcag gaatgtcact acttgtaaat  48840
tcatagaaga atttctcccc taatttgatt gtagcgccat tttgactttg tttgtcaccg  48900
actttaataa ccacgtcttt tttagggttc acttttggaa tatggttgac aacggtattc  48960
gttttaattc gttgaccaaa tgtattttgt tccgctgaat tataaacatc cccagaaaca  49020
tcagctttga cttttgtagg gagtgttaca cgcaattctt gcccaccatg cgctagaata  49080
aaggcttgtg ggtctttggc agagattgtc accgtgcctt tggcatcgtc ccaagagatc  49140
gtgaactggt tggtaatgtc taccccttta gaatctttga cacgaagtaa gtctttgatt  49200
ggtgtcactt tcgtttcgtc gtaatcatcg aagaaagaaa cgcctgtcgc aagatcgact  49260
```

```
gtgtcaaaag caaagtcttt atcgtaccct tttaagtccc aggtcatttc ataagaaaga  49320
acatcaccac gagccacttt tccatgatta atgtcttccc ctttcttgtt atgaacggct  49380
ttggttggtt ttggatcatc aggtgtatgc gtcaccaccg tattagaacg aacaagttct  49440
ttgttgtagt tttctgtttg cgtattttct acgtcacctg ttttgatccg ttcgacttcc  49500
agatacacag accaagcttg tttgcctact ttattgcttc cttcatttaa cgctgccaat  49560
aatgcttgat tcattgtaaa cgtcaagtct ttattgtctt tgttttctaa aagaatgtag  49620
gcagaaatat ctgttcctgc ttttaacgtt ttatccccta ctttaaggtc atagttcgta  49680
atagcgtgcc attttcctgt gaaacgatca tgggtcgtgt ccaagacatc attcatgccc  49740
cattcttctg tgattccgcc atagttggct ggacgttcgg aagatttcac ttcataataa  49800
atttttgttt gtaacggaat atctttatca tgtagagaaa cactgccaac tgtaccgttt  49860
ttatctgctt ttacatcttt ggaaggatta ctacctggca catggttaat cactgtattt  49920
gttaccgttt caccatcgtt tgtcagctga acagctgtat tttcaaaatc gccttctaca  49980
tttttcacta caaacggcaa gacaagtaaa tatttatacc ccattgctaa aacaacggag  50040
ccgtctgcgt tggttttcat cattgctgtg acggtgtttt ggtctaaatt aagatcataa  50100
gaagcggtca cgtctttggc ttttcctgaa ttaatcgctg cagcaacagc ttttaagtct  50160
ttctcgttta gacttgcgtc tgcttgataa actttcactt tggataaatc aatcgtcact  50220
ttttctgcat caaaggtatc tcgaatccct tgttttgtta ccgtttttgg atctacttta  50280
gcaagttctg tcgtatcccc tgtcacaatg tattgtaaag aatcgccacg cttcacattt  50340
aaatcattga tatttttctg accatcagtg acttctttat tcggaacaag aacaggaacc  50400
acattggctt tgtatcgatt gaattcaatt gttgcttttt ctggttcttt tggattccct  50460
ttcttttggt atggtctaat tgatttcgca tttaaattgg tactaaaggc aaaccattgc  50520
gcaccagata ggttgacttt tcctttggtt gtcatcccga aagagaaaga aatacgtcca  50580
ccctctctag ctagaccaac accagaacca tagtacgcat ttttatgacc tacagcatcc  50640
caatcactat tttttagtcc tgaaggacct gttccataat caaggtcttc ggttgagtag  50700
aattttccat ctgcttgttt ctttacgtag gaaccattaa tatacttgaa ggcatttttt  50760
gaaccaaagt ctgaaacaaa ttccgcatgt tctacactat aatttgttcc tagactagag  50820
tttaatgacg ataacgcata ggcaaaggca tggtctttct ctggtaaaac ttctttgcca  50880
ttagcatcat ataatttaat ggttaagcga acttttacgt ccttcccatt ggcattttta  50940
gtaccaacaa atgcagtaat aataggatcg tttgaaaata ctgcatttaa ggtgccgctt  51000
tgacttggtg cagattgaag ttcataaatg aattctgttt ttgtgatttt tcggtttaaa  51060
taactagcat ttaagcctgt atacgtgaca ttggccggtt tgtttttttc taaaagaacc  51120
gcgtagccgc ctttaggacc aaactcaaca gcagccactt ttgagctttg gaagttgcct  51180
gttgcttttc cattcatatc tttacttaat tttgtaaaaa tatctttaga ttgtccttgg  51240
tttactttgt taaattcgga ggctttaata aacttgccac ctgtaatctt gtctatttta  51300
gtatccttag tcacaatact tgaatcaaaa actaagtctt tgctgattgc ttcattaaca  51360
tagcctttgt cattcttatg tttgttgtat tccgccactt ctttttcata acgctctttt  51420
tccgctttgt tttttgccgc aatttctgca ttttctttgg caattttttc atttttggct  51480
tttaattcag ctgcttgttg ggcaatcttt ttcgcttgtt ctttttgtag ttggtctact  51540
tctttttctt tttcgactaa atctttagaa gaaacgttgc ctaaatcttc agttggtttt  51600
tcaacgacgg taatgtttgg atctttttttc gcctcatcaa ctgctttgtc aacgtctggt  51660
```

```
gtttcaaatt ctttaggaat agtcgttgat ttattcgctt cattttcagc tggtgcaact  51720
tctgttggct gccctagagg ttcattggtt gtttcagggc ttactactgg ttgttcttgt  51780
gctgattttt cagctcctac tgttggttgt tggacgtttg tggtatcatt tggggtagct  51840
gaactttgtt cagcagcaat tcctttcggc actacttctt ctgctgtggt tggttgagaa  51900
gtagtgtctt tttgtactgc cgattcttct gatactgccg ttttaggtgt ttcctttcct  51960
gactgcaggt cgggattatc gggttgcacc gtcgttgttc ctggttgcgt atctaattcc  52020
gcggcttgta cattatctgt agctaatcct acagctccta atacacctaa aaaaagaata  52080
ggggctacaa tccagtgttt ctttgcctta tacattttga agcgtttctt tacttctgtc  52140
tgttgattca tgtatcattc tcctcgattt tttatttttt gtttatagaa atagttcacg  52200
caacacaagg ggctcgttgc tttttcatca ttatttacat tcctcctcac aaaaagagaa  52260
ccgaaagttt ttcgattccc ttagcttttt tttgcgttaa aaacatttaa cgtgctatca  52320
taattgtgta aaaagtacaa atcacttctt tacaaatctt attcgtttag tcagtcggcg  52380
gaaaacggct gacttttttg ttgcctaaaa ttgcatagtc aggtactatt taagtgtctc  52440
catccgagac aatccattta tttttgttg accagcggaa actggttggc tcctaaattt  52500
ggtagattct tctgccttta atacgatcag ccaaccattt tggttggcta tttttattt  52560
ttcaatttat tccaatgatt aaaataaaaa ggagcgacat atttcgctcc tttgacttta  52620
ttatttaatt ttaaagatat tttttacttt cttctcgttt ctactaataa aacttataat  52680
acccgcagct ccaaacaaag caaatatcag accagctata gctaaccatt tattattttt  52740
ttctcctgta tgtggtaaag agtctggagc ttttgctacc tgtttcgtct tacgagattc  52800
tgaatgtgtt aatgcttgtg cttttggatg ttctttttgt ttacgccgat tgtaaaatta  52860
agctagacaa ataaaaaagt catttgtgct acactcaaga tagttcccgc aaaagaatta  52920
taaggagtga agacaaatga cctataccca tcttacatca aatgaacttg caatgataga  52980
ggcgtattat aataatcatc aatctgtagc caaaaccgca gtactattga atagatctag  53040
acaaacgatt cataaagttt accaattttt caaaacaggg cacaatgctc tagattattt  53100
caatcaatac aagaagaata aaactcgctg tggcagacgt cctattgtct tatcagatga  53160
acaaacagaa tatattcaaa agagggttgt tcaaggttgg acacctgatg tgattgttgg  53220
ccgtgcagag ttttctattt cttgttctat gcgtacactt tatcgtatgt ttaaacaagg  53280
cgtatttgaa gtgactcacc tacctatgaa aggaaaacgt aaagccaacg gacacaaaga  53340
aactcgggga aaacaatctt ttcgtcgatc acttcgtgac agaggaaatg attattctaa  53400
attcaatcaa gaatttggcc accttgaagg ggatactatt gtaggtaaaa agcacaaaag  53460
tgctgttatt accctcgttg agcgattatc taaagtaatc atcactcttc agccagaagg  53520
cagacgagct atagatattg aaaatcgttt gaaccaatgg atgcaatctg tacctaagca  53580
tctattcaaa tcaatgactt ttgattgtgg aaaggaattt tcaaattgga aatcaatcag  53640
taatatcaat gatattgata tctattttgc agatcctggt acaccatcac aaagaggttt  53700
aaatgaaaac tctaatggtt tattacgtaa agatggttta ccaaagcaaa tggacttcaa  53760
cgaagttgat gaatctttta tccaatctat tgcatcgaaa agaaataata tccctcgaaa  53820
atcattaaac tataaaacac caatagaagt attcttgagt cacatatgca aagaggaatt  53880
gtctaactta atttgacaat taatattaga aaaagataac tgttggagac caggtatttt  53940
gtctgctgaa gtagcaattg ctactaacat ttgttgttgc tttgcttctc gttcaagacg  54000
```

ttgttgttct tttgctactt gctcttgtaa cgcttcttgt cggcgctgtt cggattgttg 54060
tgcttctaag tctcttaata caccttggta ctgctgtagc tctaacttcg cattagaaag 54120
gtcttcttgt gcttgtgcat aagcaagtgt agcaacggct tgttgttctt taagttcttc 54180
caatgatttt agagaaatag tgtatgcttc ttctgcatga actaatgttt tttttgcttt 54240
ttctaaggct ttaaccgttt tttcataatt tggttgtgca ttttctaatc gagataacgc 54300
ttgttcactg acttttaatt gggcttgttt tttgccgagt gtttctttgg cgatagctaa 54360
gacttcttgc aagctcttca atgcttcttc ttccgcacgt tgtgcttctt gtttttcttt 54420
cagcacttta gcagtcgttt gttcaatcgc ttgtgcgtct gcaacttttg ttttcgcttt 54480
ttctaaaaca gcagctcgat tctgaattaa ctcattgatt gttgccaatt gatcttttgt 54540
ttgttgcagg ctttttttctg cagctgctgt ttgacggact ttttcttcgt ggttcgcttt 54600
acttttagct acaactgctt gtaacttagt caatttggcg ttattcactg acaattcttt 54660
ttcagcagta gcttgattgg ctttagtagt atttaagtct tgtaaactac tatttcgtgc 54720
attttgagct ttctgttcag catttttcgc atttgttagg ttgctttcat ttgttgcgat 54780
ttctttttgt acttgttctt ttgatttaaa gactggtatt tttccttctt caaatgttga 54840
ttcatcaagt aaacgttctt tgttgtatcc aataatatga attttacttg aaatatcatt 54900
taagtctcct gaaactgaaa cagcagtatt agtgtcctct gcacccaaca atgaatctag 54960
gtgtccataa cctgagctct gatcgtcaaa aagcatatca acaattgttt tacgcgcagc 55020
tttttcaaaa tctagcatag atatttttcc gtctacagtt tcataatacc caattgtcag 55080
attttcgtat cggttttctc ctggatatcc cttaaatcca ttctctttcg ctgctttatt 55140
aattgcatta acatcatgtc catattcttt aggattatcg tatttagcaa catcccaagc 55200
aaatttcatg gcttgattag aaatcttcaa cttttgtaat ccgaattttt cacgaacgtc 55260
gttgataagt cctacaacat aatcactcat ttgatgctta tgtttttctg taggattttt 55320
gacattgatc atttccgttg cttttgccgc atctgcttga ttttcaggga aaactttatt 55380
taatgctaat gcttcttttt ccattgcttg cttttcttgt tcagttaatt ttttgtaata 55440
atcaggtgtg aaattggcag acaagttaat ccctttatgt ccttttagct cttcttttga 55500
gctatctaaa gtattctgcg cttgctttgt tgctgtttgc ttgtctttca aagcattttc 55560
tttcgcagtt aactctgcct gtttcgcagc tgtatctgct tttgcgtctg ctactttttc 55620
ttgactagtt gtcacaacag tttgttggtc tgcaactgct tgatcgtcct tcgtcttttg 55680
atctttggct ttggcttctt ctttctgttt gttagccaat tctgcttctt ttgctgcttg 55740
ttctttttct gcctttactt tttccgcttc cgcatttttc gctaattctt caagcttgac 55800
ttgttcttgt tttgcagctg ttactgcttg ttgatcttta tcattttgca ctttagcagc 55860
agtcgtttct tttgcttttt catcaacaac agcttgttgt tggttaacgt ctgtttgagc 55920
ttgctctact actttttgtt ggtcatcaac agcctgtgta tcagtagcca cttgctcttt 55980
ggctttttca atggctgaag gtgttgcttc atccacgact tttttagctt cgtctacaac 56040
tgcttgttgg tcagtcactg cttgttgact ttgatccaat gcgtctttgt tttgatcgac 56100
cactgcttgt tggtctttaa cagattgatc aatggtgtct ttttcttttt tcgcagtgtc 56160
agcaacttgt tgtttttgat cgacaattgc ttgtttctct attacttgtt gctgtttttc 56220
agtaatggct tgctccgttg tttgtgtagc tttcactgtt ggttgttctg aagaagcatt 56280
ttcaggtgtt tttggttgcg tttgttctgc tgcctgtacc tcatttcccc caatacctgc 56340 taccccctgtt gcgactaaga tacttaaccc tgtacttgcg atctttttca ttttattttc 56400

-continued

```
ctcacttccg attttttttg ttgtaaatgg gatacccatt atcttcacgc cactgtttta  56460

atactttttc tgttacatga aatcgttgag caatttgttt gaattgcaag ccacttctct  56520

gatagctctc aaaagcttct ttagtaattt gtttgtaata ctgtcttaca tccgcagttt  56580

ctatttttc tgcgagctcc tgaacacgtt gaaaacgctc ggtgtgttct tttctatgcc  56640

aatcagggtc ttcattcatt aatcgtaaca tttctttacg ccatattttc tgttctcttt  56700

ttgtcatgct ctcacccctc gtaaattatc atagcaaaag ataactaccc tgaaaaataa  56760

taccctgtta tttcgtgaaa tatgtctcat aaggaaacac ctattgttta ctggtttcaa  56820

aaaatcaagt cttttcacag ggtttctagc aaccgttacc ctaaactcta ggtgagtcgg  56880

atattgctcg ctaccaataa ttggtaggtc gtggcaatct caccatgtac cgtagcacac  56940

caacttcaca atcattgtgt gggtctccgt tcatactgga gcttttagct tttctcctag  57000

cgtttaacga caccctgatg gcttctgtac ccttgcccct tcatagctac gctgataagc  57060

aaggcagcgg acttctcgct gactattcag ttgtaaaaaa gaaagagttc ttcttctcgt  57120

tatcagaaga tagaatgttt ctttttgtt tggcaacttt gctggaaacc agcaaacaat  57180

aggtgtttcc tgaatacttt ttttacactt cttcttcgtt taaataattc caaatagtag  57240

tgagtaactg atcaaatcgt tcgacaatga atacgtcaac atcattttct agtaaccaat  57300

ccactgttat ctcccaactc gcaccttttt gcgcagctcg atacagatgg ccttggaagt  57360

cttgcggaat gactagtttt ttcttgtccg agcaggcaac aacaagagct gtaaaagttg  57420

tttcatccat tccacaattt tgttcatagg aaaatactcg tatcacgtct ccgtgattta  57480

gttcttctgc atgggtaatt cgtttctttt ccatagagtc ctccttgttc tatttactca  57540

gttacacttc ctgtggtata ctattcttaa cattttattc attaattttt tctttcaatg  57600

atgcttgtca gctagcggaa actagttgac ttcttttttt attcactttt tttacaggaa  57660

caagggttaa cttggtggac ccttttttc gttcaatgat tttatttcca tctttgtcat  57720

aacaagaaat ga                                                      57732
```